(12) United States Patent
Kong et al.

(10) Patent No.: US 9,317,761 B2
(45) Date of Patent: Apr. 19, 2016

(54) METHOD AND AN APPARATUS FOR DETERMINING VEIN PATTERNS FROM A COLOUR IMAGE

(75) Inventors: Wai Kin Adams Kong, Singapore (SG); Chaoying Tang, Singapore (SG); Hengyi Zhang, Singapore (SG); Noah Ames Craft, Torrance, CA (US)

(73) Assignees: Nanyang Technological University, Singapore (SG); Los Angeles Biomedical Research Institute, Torrance, CA (US)

( * ) Notice: Subject to any disclaimer, the term of this patent is extended or adjusted under 35 U.S.C. 154(b) by 277 days.

(21) Appl. No.: 13/992,634

(22) PCT Filed: Dec. 8, 2011

(86) PCT No.: PCT/SG2011/000429
§ 371 (c)(1),
(2), (4) Date: Aug. 19, 2013

(87) PCT Pub. No.: WO2012/078114
PCT Pub. Date: Jun. 14, 2012

(65) Prior Publication Data
US 2014/0016832 A1    Jan. 16, 2014

Related U.S. Application Data

(60) Provisional application No. 61/421,450, filed on Dec. 9, 2010.

(51) Int. Cl.
*G06K 9/00* (2006.01)
*A61B 5/117* (2006.01)
*A61B 5/02* (2006.01)
(Continued)

(52) U.S. Cl.
CPC ........ *G06K 9/00885* (2013.01); *A61B 5/02007* (2013.01); *A61B 5/117* (2013.01); *A61B 5/1128* (2013.01); *A61B 5/489* (2013.01); *G06K 2009/00932* (2013.01)

(58) Field of Classification Search
None
See application file for complete search history.

(56) References Cited

U.S. PATENT DOCUMENTS 7,079,703 B2 * 7/2006 Kriss .................... H04N 19/176
                                                    358/3.26
7,352,448 B2    4/2008 Kono et al.
7,835,576 B2   11/2010 Kang et al.
(Continued)

FOREIGN PATENT DOCUMENTS

WO    WO 2008/054396    5/2008

OTHER PUBLICATIONS

Gnee. "A Study of Hand Vein, Neck Vein and Arm Vein Extraction for Authentication." 7th International Conference on Information, Communications and Signal Processing, Dec. 8, 2009, pp. 1-4.*

(Continued)

*Primary Examiner* — Jon Chang
(74) *Attorney, Agent, or Firm* — Schiff Hardin LLP

(57) ABSTRACT

The present invention is directed to a method of determining vein patterns from a color image for personal identification, the method comprising forming a counterpart of the color image by applying a functional relationship obtained from optimization on the color image, wherein the counterpart of the color image comprises the vein patterns. An apparatus for determining vein patterns from a color image is also disclosed.

20 Claims, 39 Drawing Sheets

(51) Int. Cl.
*A61B 5/11* (2006.01)
*A61B 5/00* (2006.01)

(56) References Cited

U.S. PATENT DOCUMENTS

| | | | |
|---|---|---|---|
| 2004/0024295 A1* | 2/2004 | Cook | A61B 5/0059 600/310 |
| 2005/0271258 A1 | 12/2005 | Rowe | |
| 2007/0043527 A1 | 2/2007 | Quan et al. | |
| 2009/0294667 A1* | 12/2009 | Gorian et al. | 250/330 |
| 2010/0215223 A1* | 8/2010 | Abe | A61B 5/0059 382/115 |

OTHER PUBLICATIONS

Watanabe et al. "Vein Authentication Using Color Information and Image Matching with High Performance on Natural Light." ICCAS-SICE, Aug. 2009, pp. 3625-2629.*
Kejun et al. "Gray-Scale Skeletonization of Near-infrared Vein Patterns Using the Improved Watershed Algorithm in Vein Pattern Biometrics." 4th IEEE Conference on Industrial Electronics and Applications, May 2009, pp. 241-245.*
Zhichao et al. "Two Modality-Based Bi-Finger Vein Verification System." IEEE 10th International Conference on Signal Processing, Oct. 24, 2010, pp. 1690-1693.*
M. Motivans and T. Kyckelhaln, "Federal Prosecution of Child Sex Exploitation Offenders, 2006", Bureau of Justice Statistics, Dec. 2007.
P. Kubelka, "New contribution to the optics of intensely light-scattering materials", JOSA, vol. 38, pp. 448-457, 1948.
R.R. Anderson and J. A. Parrish, "The Optics of Human Skin", J. Invest. Dermatol., vol. 77, No. 1, pp. 13-19, 1981.
S. Wan, R.R. Anderson, and J.A. Parrish, "Analytical modeling for the optical properties of the skin with in vitro and in vivo applications", Photochem. Photobiol., vol. 34, No. 4, pp. 493-499, 1981.
B. Diffey, "A Mathematical Model for Ultraviolet Optics in Skin", Phys. Med. Biol., vol. 28, No. 6, pp. 647-657, 1983.
M.J.C. Van Gemert, S.L. Jacques, H.J.C.M. Sterenborg, and W.M. Star, "Skin Optics", IEEE Trans. Biomed. Eng., vol. 36, No. 12, pp. 1146-1154, 1989.
S. Cotton and E. Claridge, "Developing a predictive model of skin colouring", In SPIE vol. 2708, Medical Imaging 1996, pp. 814-825, 1996.
E. Claridge, S. Cotton, P. Hallc, and M. Moncrieffd, "From Colour to Tissue Histology: Physics-Based Interpretation of Images of Pigmented Skin Lesions", Med. Image Anal., No. 7, pp. 489-502, 2003.
M. Doi and S. Tominaga, "Spectral Estimation of Human Skin Colour using the Kubelka-Munk Theory", In SPIE/IS&T Electronic Imaging, SPIE, vol. 5008, pp. 221-228, 2003.
M. Störring, "Computer Vision and Human Skin Color", PhD Thesis, Aalborg University, 2004.
N. Tsumura, H. Haneishi, and Y. Miyake, "Independent Component Analysis of Skin Color Image", Josa(A), vol. 16, No. 9, pp. 2169-2176, 1999.
N. Tsumura, H. Haneishi, and Y. Miyake, "Independent Component Analysis of Spectral Absorbance Image in Human Skin", Opt. Rev., vol. 7, No. 6, pp. 479-482, 2000.
S. L. Jacques, "Skin Optics", Oregon Medical Laser Center, http://omlc.ogi.edu/news/jan98/skinoptics.html, 1998.
C. Donner and H. W. Jensen, "A Spectral BSSRDF for Shading Human Skin", Proceedings of the Eurographics Symposium on Rendering, pp. 409-417, 2006.
Y. Luo and R. K. Ward, "Removing the blocking artifacts of block-based DCT compressed images", IEEE TIP, vol. 12, No. 7, pp. 838-842, 2003.
D. Sun and W. Chan, "Postprocessing of low bit-rate block DCT coded images based on a fields of experts prior", IEEE TIP, vol. 16. No. 11, pp. 2743-2751, 2007.
W. T. Freeman, T. R. Jones, and E. C. Pasztor, "Example-based super-resolution", Computer Graphics, vol. 22, No. 2, pp. 56-65, 2002.
W. T. Freeman, E. C. Pasztor, and O. T. Carmichael, "Learning low-level vision", IJCV, vol. 40, No. 1, pp. 25-47, 2000.
A. Foi, V. Katkovnik, and K. Egiazarian, "Pointwise shape-adaptive DCT for high-quality denoising and deblocking of grayscale and color images", IEEE TIP, vol. 16, No. 5, pp. 1395-1411, 2007.
J. Chou, M. Crouse, and K. Ramchandran, "A simple algorithm for removing blocking artifacts in block-transform coded images", IEEE Signal Processing Letters, vol. 5, No. 2, pp. 33-35, 1998.
Z. Wang and A. C. Bovik, "Mean squared error: Love it or leave it? A new look at signal fidelity measures", IEEE Signal Processing Magazine, vol. 26, No. 1, pp. 98-117, 2009.
Z. Wang, A. C. Bovik, H. R. Sheikh and E. P. Simoncelli, "Image quality assessment: from error visibility to structural similarity", IEEE TIP, vol. 13, No. 4, pp. 600-612, 2004.
Z. Wang, A. C. Bovik and L. Lu, "Why is image quality assessment so difficult?", Proceedings of the IEEE ICASSP, May 2002.
Lim C. L. et al., "Biometric Verification Using Thermal Images of Palm-Dorsa Vein Patterns", IEEE Transactions on Circuits and Systems for Video Technology, vol. 14 (2), pp. 199-213, 2004.

* cited by examiner

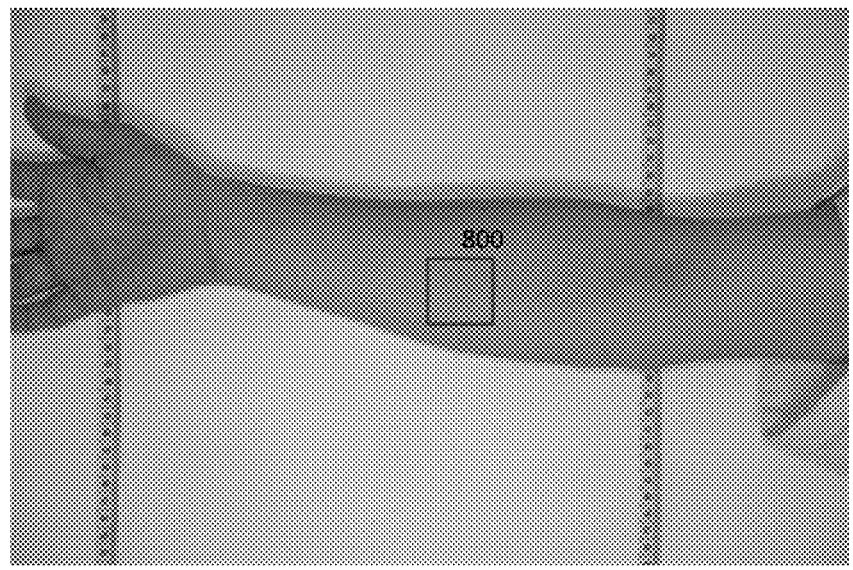
Figure 8(a)
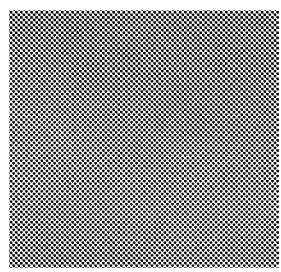 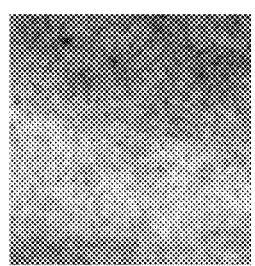 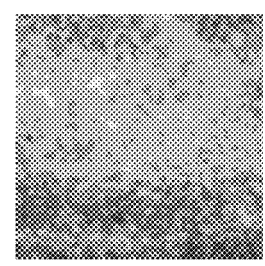 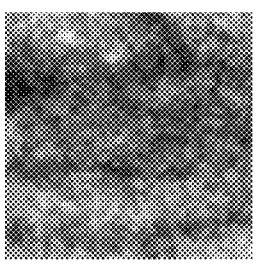
Figure 8(b)  Figure 8(c)  Figure 8(d)  Figure 8(e)
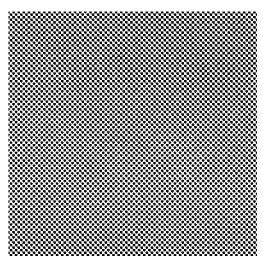 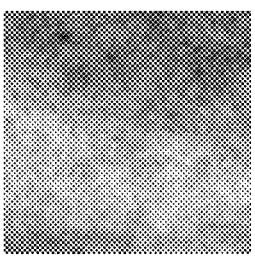 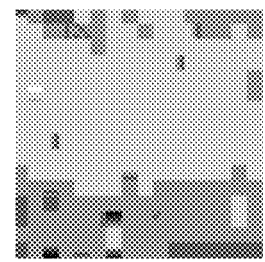 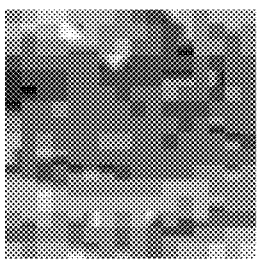
Figure 8(f)  Figure 8(g)  Figure 8(h)  Figure 8(i)

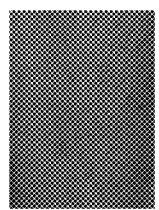
Figure 35(a)
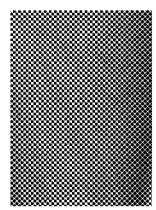
Figure 35(b)
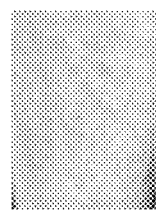
Figure 35(c)
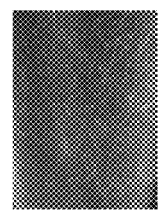
Figure 35(d)
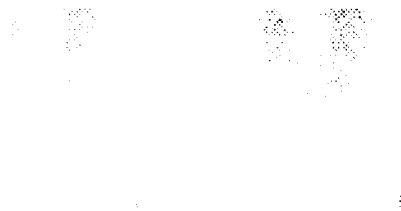
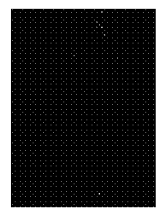
Figure 35(e)
Figure 35(f)
Figure 35(g)
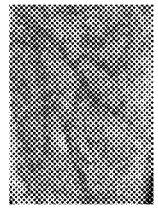
Figure 35(h)
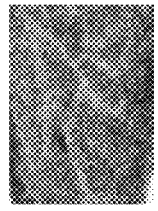
Figure 35(i)
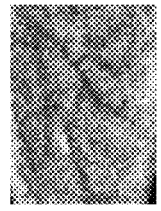
Figure 35(j)

METHOD AND AN APPARATUS FOR DETERMINING VEIN PATTERNS FROM A COLOUR IMAGE

CROSS-REFERENCE TO RELATED APPLICATION

This application makes reference to and claims the benefit of priority of an application for "Method and Apparatus for Extracting Blood Vessel Patterns in Colour Images" filed on Dec. 9, 2010 with the United States Patent and Trademark Office, and there duly assigned application No. 61/421,450. The content of said application filed on Dec. 9, 2010 is incorporated herein by reference for all purposes, including an incorporation of any element or part of the description, claims or drawings not contained herein and referred to in Rule 20.5(a) of the PCT, pursuant to Rule 4.18 of the PCT.

TECHNICAL FIELD

Various embodiments generally relate to the field of determining vein patterns from colour images, in particular determining vein patterns from colour images for personal identification.

BACKGROUND

Personal identification is a critical process in the forensic sciences. Law enforcement agents and forensic laboratories around the world use fingerprint, palmprint, facial recognition, deoxyribonucleic acid (DNA), and teeth regularly for criminal and victim identification. However, these biometric traits are not applicable to the legal cases when only evidence images are available. Recent technological advances have allowed for a proliferation of digital evidence images, which may be admissible as evidence in legal cases (e.g. child sexual abuse, child pornography and masked gunmen/terrorists). However, use of these images can be very challenging, because the faces of criminals or victims are more than often not visible.

For example, the United States Bureau of Justice Statistics has reported that child sex offenses are the fastest growing offenses of the Federal criminal caseload. Many individuals post child pornography on the Internet and anyone who possesses, makes, prints, publishes, distributes, sells or imports child pornography commits a criminal offense. Criminals are usually careful not to show their faces in child pornography for fear of identification. Due to the lack of effective identification technology, a huge amount of child pornography has been posted on the Internet. For example, in Canada alone, about 30,000 cases of child pornography have been reported. The U.S. Customs Service has estimated that about 100,000 websites offer child pornography. In addition to child pornography, personal identification based on evidence images or videos may be applicable to many other crimes such as rape, sexual assault, and masked gunmen.

Even though tattoos and large skin marks have been used, they are ineffective in some of these cases because the skin exposed in evidence images may have neither unique tattoos nor enough skin marks for personal identification. For example, some people, especially gang members, can have the same tattoo pattern, while many may not have tattoos. A similar problem may be faced when dealing with skin marks.

Vein recognition is a biometric technology that performs personal verification and identification based on the vast network of blood vessels under the skin surface. The blood vessel between the skin and the muscle covering most parts of the human body is a powerful biometric trait, because of its universality, permanence and distinctiveness. It is considered to be a unique and stable biometric trait that is nearly impossible to forge. The vast network of larger blood vessels is believed to be "hardwired" into the body at birth, and remains relatively unaffected by aging, except for predictable growth, as with fingerprints. In addition, as the blood vessels are hidden underneath the skin and are almost invisible, they are much harder to be duplicated compared with other biometric traits.

Vein biometrics has received considerable attention in the last decade for commercial applications. The current systems developed in laboratories and companies use infrared (IR) or laser imaging technologies to obtain high quality vein patterns from the hand (e.g. finger and palm) and the wrist for commercial applications. However, these approaches are inapplicable to forensic identification from colour images, where no infrared or laser images are available and vein patterns are not visible in these colour images.

Uncovering vein patterns from digital or colour images taken by consumer cameras is challenging because the veins lie underneath the skin surface and are almost invisible to the naked eye. Skin is an intricate layered material whose internal structures vary with individuals, body sites, and time. Additionally, the physical process of image formation may complicate the uncovering of vein patterns from the colour images. When the light from an illumination source hits the skin, some is absorbed while some is reflected and captured by the sensor in a camera. Currently there has been no report of any algorithm or software package especially designed for uncovering vein patterns from colour images taken by consumer cameras.

Thus, there is a need to provide a method and an apparatus seeking to address at least the problems mentioned such that vein patterns from the skin in colour images are uncovered for personal identification.

SUMMARY OF THE INVENTION

In a first aspect, the present invention relates to a method of determining vein patterns from a colour image for personal identification. The method comprises forming a counterpart of the colour image by applying a functional relationship obtained from optimization on the colour image, wherein the counterpart of the colour image comprises the vein patterns.

According to a second aspect, the present invention relates to a method of extracting vein patterns from an image comprising a plurality of pixels for personal identification. The method comprises generating an orientation map for the plurality of pixels of the image; and determining for each of the plurality of pixels whether a pixel represents a vein or a part thereof based on the orientation map.

According to a third aspect, the present invention relates to an apparatus for determining vein patterns from a colour image for personal identification. The apparatus comprises a determining unit configured to form a counterpart of the colour image by applying a functional relationship obtained from optimization on the colour image, wherein the counterpart of the colour image comprises the vein patterns.

In a fourth aspect, an apparatus for extracting vein patterns from an image comprising a plurality of pixels for personal identification is provided. The apparatus comprises a vein pattern extraction unit comprising a map generating unit configured to generate an orientation map for the plurality of pixels of the image; and a classifier configured to determine for each of the plurality of pixels whether a pixel represents a vein or a part thereof based on the orientation map.

In a fifth aspect, the method or the apparatus of the present invention for use in forensic identification is provided.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 1 shows a schematic block diagram of a method of determining vein patterns from a colour image, in accordance to various embodiments;

FIG. 8 shows (a) a raw image of the inner right forearm of a male subject, (b) the skin image cropped from the indicative rectangle 800 of (a), (c) the Y component of (b), (d) the U component of (b), (e) the V component of (b), (f) the JPEG compressed image of (b), (g) the Y component of (f), (h) the U component of (f), (i) the V component of (f), in accordance to various embodiments;

FIG. 35 shows (a) original digital photographic skin image (in colour) of the front side of the left leg of a male subject, (b) the corresponding NIR images, (c) the first components obtained from Tsumura et al.'s method, (d) the second components obtained from Tsumura et al.'s method, (e) the distribution maps of melanin obtained from Claridge et al.'s method, (f) the distribution maps of hemoglobin obtained from Claridge et al.'s method, (g) the distribution maps of depth of papillary dermis obtained from Claridge et al.'s method, (h) the distribution maps of melanin obtained from the vein uncovering algorithm in accordance with various embodiments of the invention, (i) the distribution maps of hemoglobin obtained from the vein uncovering algorithm in accordance with various embodiments of the invention and (j) the distribution maps of depth of dermis obtained from the vein uncovering algorithm in accordance with various embodiments of the invention;

Figure 46:
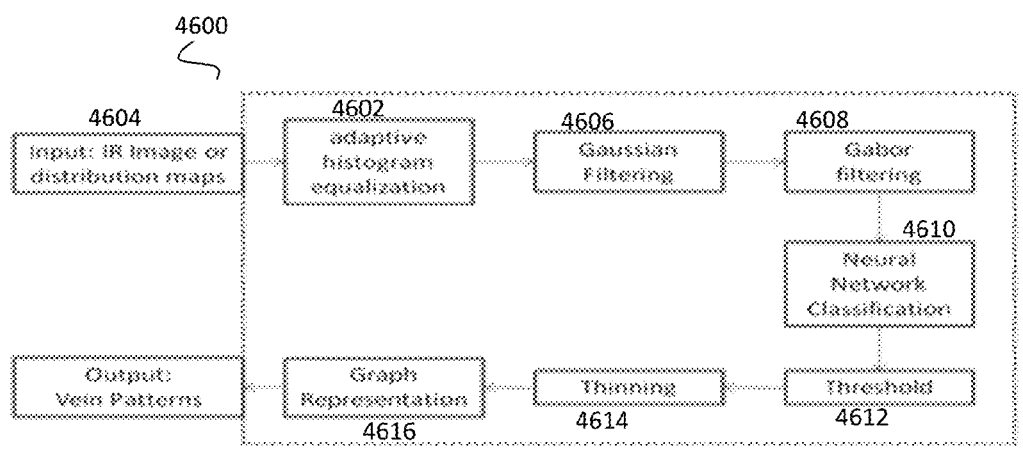
Figures 50A, 50B:
Figures 50C, 50D:
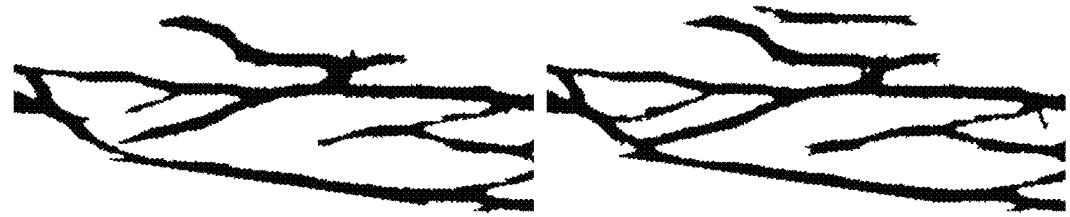
Figure 51:
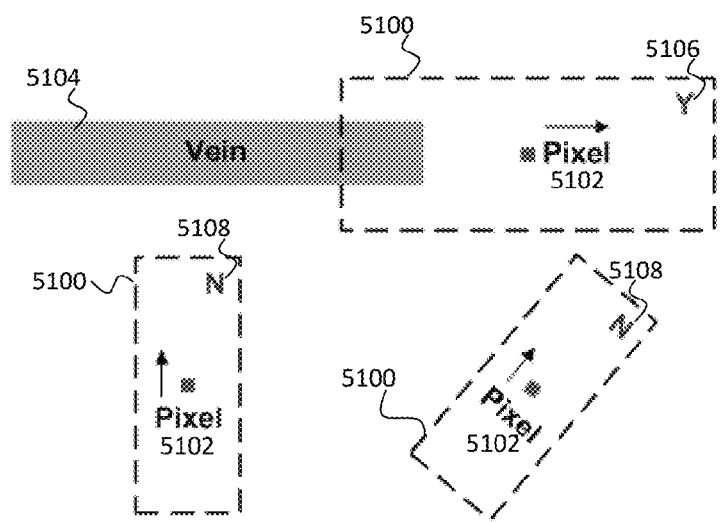

and (d) the sampled points from the vein patterns, in accordance to various embodiments;

FIG. 46 shows a schematic block diagram for a vein extraction algorithm, in accordance to various embodiments;

FIG. 47 shows (a) the image contrast of an example of an original image captured by an IR camera, and (b) the image contrast of an example of an output from adaptive histogram equalization, in accordance to various embodiments;

FIG. 48 shows outputs from (a) an adaptive histogram equalization, and (b) a low-pass (Gaussian) filter, in accordance to various embodiments;

FIG. 49 shows output examples from the Gabor filter: (a) a magnitude map, (b) a scale map, (c) an orientation map, and (d) an output example of the neural network classifier, in accordance to various embodiments;

FIG. 50(a) shows an exemplary illustration of binarized vein patterns, in accordance to various embodiments;

FIG. 50(b) shows an exemplary illustration of vein patterns with a threshold being applied around the vein patterns, in accordance to various embodiments;

FIG. 50(c) shows an exemplary illustration of vein patterns with a threshold being applied to elongate the vein patterns, in accordance to various embodiments;

FIG. 50(d) shows an exemplary illustration of vein patterns with morphologic operators being applied to refine the vein patterns, in accordance to various embodiments;

FIG. 51 shows a schematic representation of a vein elongation process, in accordance to various embodiments;

FIG. 52 shows (a) an initial graph of a vein pattern, (b) additional nodes being added to better represent the vein patterns of (a), (c) broken veins being connected for the vein patterns of (a), and (d) short veins being removed for the vein patterns of (a), in accordance to various embodiments.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

In order that the invention may be readily understood and put into practical effect, particular embodiments will now be described by way of examples and not limitations, and with reference to the figures.

In a first aspect, a method of determining vein patterns from a colour image for personal identification is provided as shown in FIG. 1. In FIG. 1, the method 100 comprises forming a counterpart of the colour image by applying a functional relationship obtained from optimization on the colour image 102, wherein the counterpart of the colour image comprises the vein patterns.

In the context of various embodiments, the term "determining" may refer but not limited to obtaining, selecting, extracting, uncovering, revealing, displaying, calculating, forming, or establishing. The term "determining" may also refer to a combination of actions, for example, calculating and selecting, or uncovering and extracting and displaying.

As used herein, the term "vein patterns" generally refers to a 'mesh' of blood carrying tubes. In this context, vein patterns may be referred to those of a human. Vein patterns may be from any part of the body, for example, limbs, palms, and wrists. Vein patterns may be found in various layers under a skin.

The term "colour image" may refer to a photographic image which may be taken by a digital camera or may be a scanned image of a photograph. For example, the colour image may be represented by a greyscale version. The term "colour image" may be interchangably referred to as a digital photographic image or a test image.

The term "counterpart" may refer to an associating or corresponding entity with respect to its origin, for example, the colour image. The counterpart of the colour image may be itself an image (e.g. a colour image) and closely resemble the colour image or may have the same functions and characteristics as the colour image. In other words, the counterpart may be a processed version of the colour image. For example, the counterpart of the colour image may be but is not limited to an infrared (IR) image, a near-infrared (NIR) image or a black-and-white image. The counterpart of the colour image may also be a different representation of the colour image. For example, the counterpart of the image may be a skin-characterizing representation, or an inversed colour component of the colour image, or a form of encoding of the colour image, or a map of the colour image to a different domain. In some embodiments, the counterpart of the colour image may be the colour image.

In the context of various embodiments, the term "functional relationship" generally refers to a function, typically a mathematical representation that associates, links, or relates the counterpart of the colour image to the colour image. For example, the functional relationship given pixel values of the counterpart of the colour image may depend on the pixel values of the colour image.

As used herein, the functional relationship is obtained from optimization. In the context of various embodiments, the term "optimization" may generally refer to the art and science of allocating limited resources to the best possible effect. Optimization may be effected mathematically to the functional relationship, for example, in a form of a factor or a variable depending on a particular criteria. In various embodiments, optimization may be used in training a network, a neural network or a classifier, in automatically adjusting image intensity, in determining optimal parameter ranges through colour, in model generation, in model selection and in adjustment of vein patterns from color images as described in the examples herein. For example, the functional relationship or more specifically the functional relationship obtained from optimization may be a support vector machine, or a decision tree, or a logistic regression. All regression techniques may also be considered to construct this functional relationship.

The term "personal identification" may refer to a process of identifying a subject via a biometric trait. For example, personal identification may comprise forensic identification. In various embodiments, the method 100 comprises identifying a subject based on the vein patterns or establishing the identity of a subject based on the vein patterns.

Figure 2A:
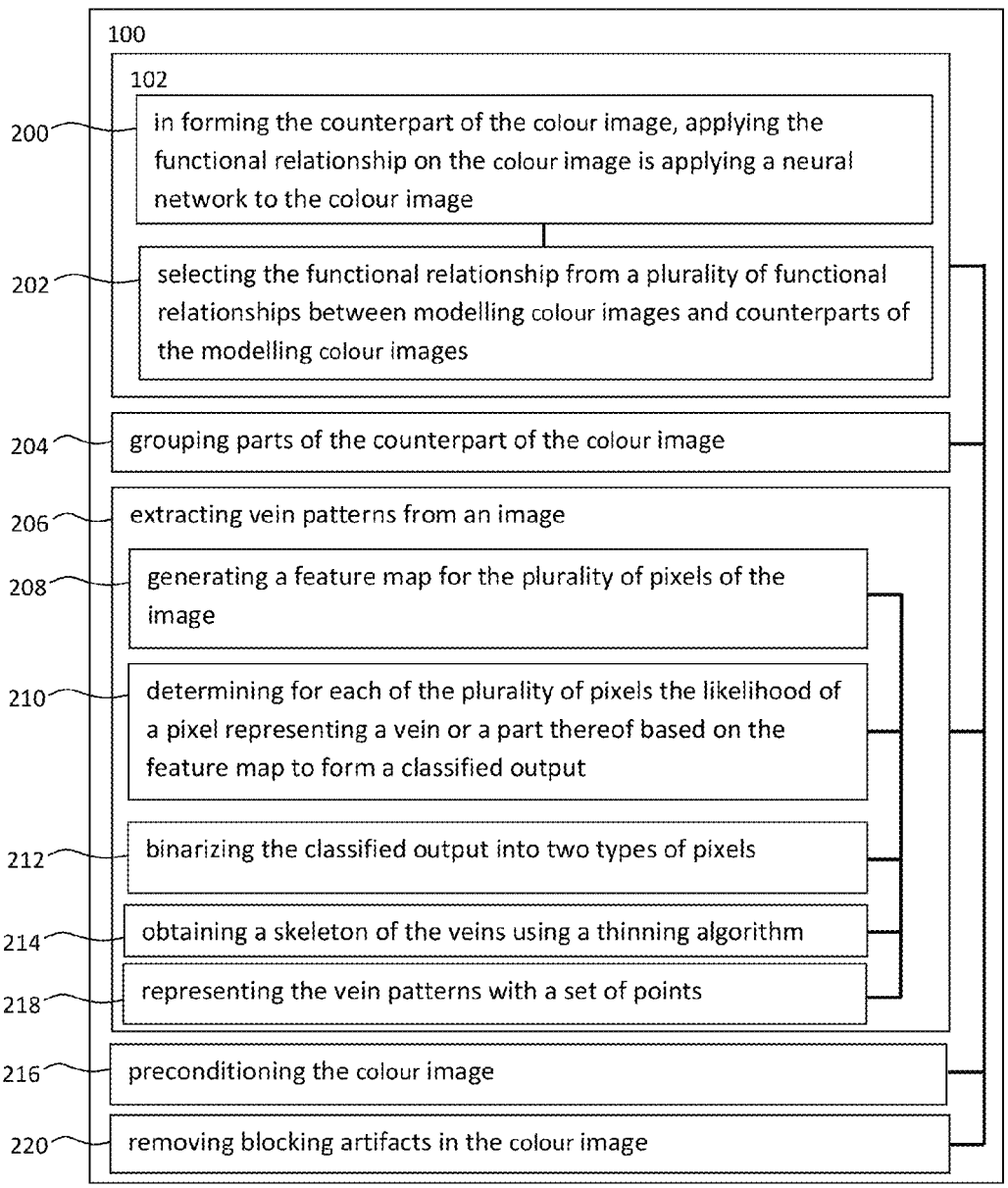
FIGS. 2(a) to 2(c), each shows a schematic block diagram of a method of determining vein patterns from a colour image, in accordance to various embodiments.

In various embodiments, in forming the counterpart of the digital image 102, applying the functional relationship on the colour image may be applying a neural network on the colour image 200, as illustrated in FIG. 2(a). The term "neural network" generally refers to a series of algorithms that attempt to identify underlying relationships in a set of data by using a process that mimics the way the human brain operates. Neural networks have the ability to adapt to changing input so that the network produces the best possible output without the need to redesign the output criteria.

In various embodiments, vein patterns may be determined from a colour image such as a photographic image. As the vein patterns may not be visible from the colour image, image processing methods and apparatus (or systems) may be required to determine the vein patterns. Vein patterns may need to be uncovered prior to extracting the vein patterns. In view of the complexity, neural networks may be employed to determine the vein patterns from the colour image. The neural network(s) may be trained to recognise vein patterns. The training of the neural network(s) may involve prior knowledge, for example, as provided by a database of information or records. The training of the neural network(s) may also be performed by inferencing from inputs to the network(s) so as to learn and increase knowledge. Because of the inference capability of neural networks, the output may be obtained more quickly and often more accurately as compared to some direct computational (including mathematical) solutions. Using the vein patterns, personal identification may be carried out.

According to various embodiment, the functional relationship may be formulated using a modelling colour image and a counterpart of the modelling colour image, wherein the counterpart of the modelling colour image comprises modelling vein patterns.

As used herein, the term "modelling" generally refers to a reference used for formulating the functional relationship. In this context, for example, the modelling colour image may be a digital image (in colour) of a particular skin area and the counterpart of the modelling colour image may be an IR image of the same skin area. The modelling colour image may also be referred to as a training image, which may generally refer to an image used for training the neural network. As the vein patterns may be observed from the IR image, the IR image of the particular skin area can be considered as the output of the functional relationship to be formulated while the colour image of that skin area can be considered as the input of the functional relationship. Having both the input and the output known, the functional relationship may be evaluated. The term "counterpart" defined for the colour image above may be similarly applicable to the term "counterpart" used for the modelling colour image.

In some examples, the modelling colour image may also be the colour image from which the vein patterns are determined by the method 100 in accordance to various embodiments.

In various embodiments, the functional relationship obtained from optimization may be formulated using an approximate regression comprising a least-squares-error function with an optimal weight. The term "optimal weight" may refer to the best possible factor for the least-squares-error function such that errors are minimized between the output of the least-squares-error function and the actual (original) vein patterns in this case.

According to various embodiments, forming the counterpart of the colour image 102 may further comprise selecting the functional relationship from a plurality of functional relationships between modelling colour images and counterparts of the modelling colour images 202. For example, a plurality of modelling colour images may have a plurality of counterparts of the modelling colour images, from which, a plurality of functional relationships may have been evaluated. The plurality of functional relationships may be stored and made accessible for selecting the functional relationship 202.

In various embodiments, the method 100 may further comprise grouping parts of the counterpart of the colour image 204. As used herein, the term "parts" may refer to portions or areas or more specifically, some pixels of the image.

In some embodiments, the counterpart of the modelling colour image may comprise an infrared (IR) image or a near-infrared (NIR) image. The functional relationship may comprise a plurality of functional relationships between modelling colour images and IR images of the modelling colour images, wherein each modelling colour image and the respective IR image thereof forms an image pair; and wherein for at least one of the modelling colour images, an IR image of the at least one of the modelling colour images is captured simultaneously by a camera.

Forming the counterpart of the colour image 102 may further comprises training with a set of image pairs formed by the modelling colour images and the IR images thereof. The functional relationship may comprise a parametric vector for predicating the IR image from the colour image. The parametric vector may be a mathematical vector or function containing a set of control parameters for predicating the IR image from the colour image. For example, the parametric vector may contain parameters such as lighting being set at predetermined values. In these embodiments, grouping parts of the counterpart of the colour image 204 may comprise assigning pixels in the IR image having substantially the same colour to a same group.

In other embodiments, the colour image may comprise colour components, the counterpart of the colour image may comprise skin-characterizing variables, and forming a counterpart of the colour image 102 may comprise determining distributions of the skin-characterizing variables to form the vein patterns. For example, determining distributions of the skin-characterizing variables may comprise applying an inverse of the functional relationship on the colour components obtained from the colour image. In one embodiment, the colour components may comprise a red (R) component, a green (G) component, and a blue (B) component. The skin-characterizing variables may comprise a volume fraction of an epidermis occupied by melanosomes, a volume fraction of a dermis occupied by blood and a depth of the dermis. In these embodiments, forming the counterpart of the colour image 102 may further comprise training the neural network by back-propagation. Simply, back-propagation is a common method of training a neural net or network in which the initial system output is compared to the desired output, and the system is adjusted until the difference between the two is minimized.

In various embodiments, the functional relationship may be formulated using at least a reflectance and a transmittance of a skin. The reflectance and the transmittance of the skin may be dependent on reflectances and transmittances of a plurality of layers of the skin. Each of the plurality of layers of the skin may be selected from the group consisting of a stratum corneum, an epidermis and a dermis.

In some embodiments, the functional relationship may be formulated further using a spectral response function of a camera used for capturing the modelling colour image or the colour image. For example, the spectral response function may be the R, G, or B spectral response function of the camera.

In other embodiments, the functional relationship may be formulated further using a measure of an illuminant, the illuminant corresponding to a type of light source used in capturing the modelling colour image or the colour image. For example, the illuminant may be D65, A and F, which are standard illuminants established by The International Commission on Illumination. The characteristics of the illuminant and the camera may play an important role on the skin colour formation in an image.

According to various embodiments, the method 100 may further comprise extracting vein patterns from an image 206, wherein the image comprises a plurality of pixels. The image may be selected from the group consisting of an infrared (IR) image, a colour image, a black-and-white image and a greyscale image.

Extracting vein patterns 206 may comprise generating a feature map for the plurality of pixels of the image 208, determining for each of the plurality of pixels the likelihood of a pixel representing a vein or a part thereof based on the feature map to form a classified output 210, and binarizing the classified output into two types of pixels 212 such that one type of pixels represents the veins while the other type of pixels represents the skin.

As used herein, the term "extracting" may refer to taking out the required parts. For example, "extracting" may further include removing undesired parts to retain the required parts. The term "extracting" may also be interchangably used with the term "determining", as defined above.

The term "feature map" may refer to a map or data representing a particular feature or parameter or characteristic of the image. The feature map may be graphically or mathematically represented. The feature map may be a form of simplified or alternative representation of, in this case, an image. For example, the feature map may comprise a scale map, or an orientation map, or a response map. The scale map may comprise the ratio of a length or distance on the image to the corresponding length or distance on the actual surface such as the skin surface. The orientation map may contain information or data representing the direction with respect to a reference in the acutal surface. In this context, the orientation map may represent the orientation or the direction of the veins. For example, in the orientation map, connected pixels with the same orientation may be considered to form a group. The response map may comprise a relationship between a spectral response of the image and a reflectance and transmittance of light exposed on the actual surface.

In various embodiments, generating the feature map 208 may further comprise grouping the plurality of pixels; and determining the likelihood of a pixel representing a vein or a part thereof 210 may comprise determining for each of the groups, the likelihood of a pixel therein representing a vein or a part thereof and to subsequently apply the likelihood outcome of that pixel to all pixels in that group. The plurality of pixels may be grouped based on the scale map and the orientation map. In various embodiments, the plurality of pixels may be grouped based on the orientation map. In other embodiments, the plurality of pixies may be grouped based on a combination of different feature maps.

Figure 2B:
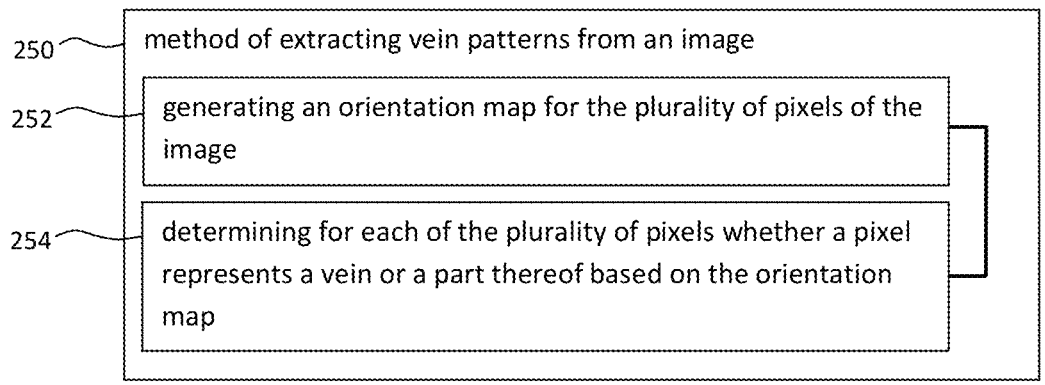

In a second aspect, a method of extracting vein patterns from an image comprising a plurality of pixels for personal identification is provided as shown in FIG. 2(b). The method 250 comprises generating an orientation map for the plurality of pixels of the image 252; and determining for each of the plurality of pixels whether a pixel represents a vein or a part thereof based on the orientation map 254. In various embodiments, the terms "image" and "orientation map" may be as defined above.

According to these embodiments, binarizing the classified output 212 may comprise utilizing a threshold applicable to a skin area of the image to determine the veins. In some embodiments, the skin area of the image may comprise the skin area represented as a feature map.

In the context of various embodiments, the term "threshold" may generally refer to a predetermined value which is used for comparison purpose with other measured values. The threshold may refer to a dynamic value such that different images may have different thresholds as the value may be computed based on statistic or characteristics of the input colour image or a feature map.

For example, binarizing the classified output 212 may comprise utilizing a second threshold applicable to areas around the veins determined by the first threshold to elongate the determined veins.

the term "elongate" may refer to extending, interpolating, or approximating.

Figure 2C:
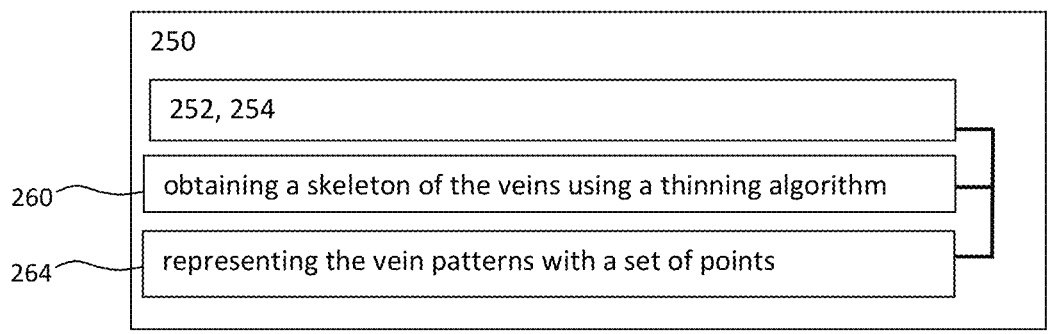

In various embodiments, extracting vein patterns 206, 250 may further comprise obtaining a skeleton of the veins using a thinning algorithm 214, 260 (as illustrated in FIG. 2(c)). The thinning algorithm may allow representation in a form of a single line.

The method 100 may further comprise prior to generating the feature map or the orientation map 208, 252, preconditioning the colour image 216. Preconditioning the colour image 216 may comprises adaptively mapping a part of the colour image to a desired distribution such that the vein patterns become optimally visible and image contrast of the colour image is increased; and capturing local information from the colour image such that veins are detectable from the colour image. As used herein, the term "optimally visable" may refer to forming an optimal function to visualize the veins. The optimal function may allow for the clearest possible distinction between veins and other parts. The term "desired distribution" may refer to a targetted map for a histogram or an adaptive histogram of the colour image. For example, preconditioning the colour image 216 may comprise increasing image contrast of the colour image, and at least minimizing or removing high frequency noise in the colour image. In another example, preconditioning the colour image 216 may comprise exploring a searching space formed by images (for example, feature maps) generated from the colour images. The term "exploring" may refer to going through or scanning through and the term "searching space" may refer to a space or an area containing pixels to which an algorithm may be applied. Preconditioning the colour image 216 may further comprise capturing local information from the colour image such that veins are detectable from the colour image.

Preconditioning the colour image 216 may further comprise forming an objective function for the colour image.

As used herein, the term "objective function" may refer to in nonlinear programming, the function, expressing given conditions for a system, which one seeks to minimize subject to given constraints. "Objective function" may be associated with optimization.

In various embodiments, extracting vein patterns 206, 250 may further comprise representing the vein patterns with a set of points 218, 264.

In the context of various embodiments, the term "points" may refer to a pixel or a collection of pixels substantially forming a dot or a patch. The size of a point may be 1, 2 or more pixels. The shape of a point may be regular, for example, a circle, an ellipse, a rectangle, a square, or a polygon. In some embodiments, the shape of the point may be irregular.

For example, extracting vein patterns 206, 250 may comprise representing the vein patterns as a graph by detecting intersections and end points of the vein patterns as nodes of the graph, and linking the nodes to form the graph. In this example, representing the vein patterns as the graph may comprise including additional nodes if it is determined that a curvature of a vein segment is larger than a threshold. In another example, representing the vein patterns as the graph may comprise combining vein patterns from different selected functional relationships obtained from IR images.

In various embodiments, determining the likelihood of a pixel representing a vein or a part thereof 210, 254 comprises allowing for manual correction of the digital image.

According to various embodiments, the method 100 may further comprise removing blocking artifacts in the digital image 220, wherein the digital image is a compressed digital image. Removing blocking artifacts 220 may comprise using a knowledge-based approach or a one-pass algorithm.

Figure 3:
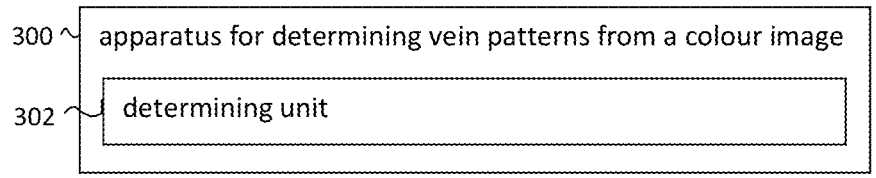
FIG. 3 shows a schematic block diagram of an apparatus for determining vein patterns from a colour image, in accordance to various embodiments.

In a third aspect, an apparatus for determining vein patterns from a colour image for personal identification is provided as shown in FIG. 3. In FIG. 3, the apparatus 300 comprises a determining unit 302 configured to form a counterpart of the colour image by applying a functional relationship obtained from optimization on the colour image, wherein the counterpart of the colour image comprises the vein patterns. In various embodiments, the determining unit 302 configured to form the counterpart of the colour image by applying the functional relationship on the colour image may be configured to form the counterpart of the colour image by applying a neural network on the colour image. The term "functional relationship" may be as defined above.

In various embodiments, the apparatus 300 may comprise an identification unit configured to identify a subject based on the vein patterns or to establish the identity of a subject based on the vein patterns.

In some embodiments, the functional relationship may comprise a plurality of functional relationships between modelling colour images and counterparts of the modelling colour images.

Figure 4A:
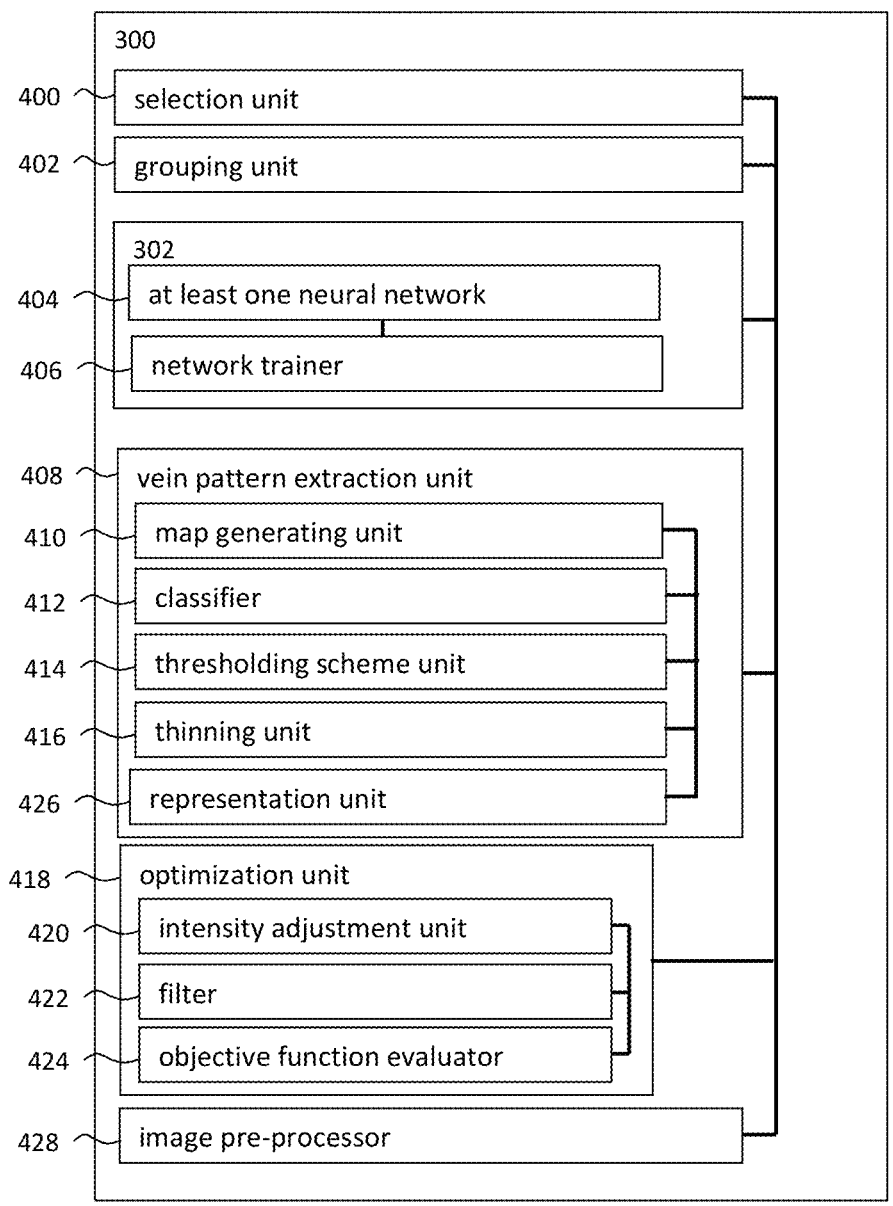
FIGS. 4(a) to 4(c), each shows a schematic block diagram of an apparatus for determining vein patterns from a colour image, in accordance to various embodiments.

In various embodiments, the apparatus 300 may further comprise a selection unit 400, as illustrated in FIG. 4(a), configured to select a functional relationship from the plurality of functional relationships such that the determining unit 302 may be configured to apply the selected functional relationship on the colour image to form the counterpart of the colour image. The apparatus 300 may further comprise a grouping unit 402 configured to group parts of the counterpart of the colour image. The colour image, the counterpart of the modelling colour image and the functional relationship may be defined as above.

In various embodiments, the determining unit 302 may be configured to be trained with a set of image pairs formed by the modelling colour images and the respective IR images thereof. The determining unit 302 may apply the functional relationship comprising a parametric vector for predicating the IR image from the colour image. The grouping unit 402 may be configured to assign pixels in the IR image having substantially the same colour to a same group.

In various embodiments, the colour image may comprise colour components, the counterpart of the colour image may comprise skin-characterizing variables and the determining unit 302 may be configured to determine distributions of the skin-characterizing variables to form the vein patterns. The determining unit 302 may be configured to apply an inverse of the functional relationship on the colour components obtained from the colour image. The colour components and the skin-characterizing variables may be as defined above.

In various embodiments, the determining unit 302 may comprise at least one neural network 404. For example, the at least one neural network 404 may comprise a feed-forward neural network. The feed-forward neural network may comprise a three-layered feed-forward neural network.

In some embodiments, the determining unit 302 may comprise a network trainer 406 configured to train the at least one neural network 404 by back-propagation. The network trainer 406 may use an infrared (IR) image for training the at least one neural network 404.

In various embodiments, the at least one neural network 404 may be dependent on spectral response functions of a camera used for capturing the colour image. In some embodiments, the at least one neural network 404 may be dependent on a measure of an illuminant corresponding to a type of light source used in capturing the colour image. In other embodiments, the at least one neural network 404 may comprise different neural networks dependent on different spectral response functions and different illuminants.

The functional relationship may be formulated as defined above. The functional relationship may be formulated further using a spectral response function of a camera used for capturing the modelling colour image or the colour image. For example, the spectral response function of the camera may comprise a plurality of spectral response functions of the camera comprising a R spectral response function, a G spectral response function, and a B spectral response function. The functional relationship may be formulated further using a measure of an illuminant, the illuminant corresponding to a type of light source used in capturing the modelling colour image or the colour image. For example, the type of light source may be selected from the group consisting of daylight, an incandescent lamp and a fluorescent lamp. The illuminant may be selected from the group consisting of an illuminant D65, an illuminant A and an illuminant F.

In various embodiments, the apparatus 300 may further comprise a vein pattern extraction unit 408 configured to extract vein patterns from an image, the image comprising a plurality of pixels. The image may be defined as above.

In various embodiments, the vein pattern extraction unit 408 may comprise a map generating unit 410 configured to generate a feature map for the plurality of pixels of the image, a classifier 412 configured to determine for each of the plurality of pixels the likelihood of a pixel representing a vein or a part thereof based on the feature map to form a classified output, and a thresholding scheme unit 414 configured to binarize the classified output into two types of pixels such that one type of pixels represents the veins while the other type of pixels represents the skin. For example, the map generating unit 410 may comprise a multi-scale directional filter. The feature map may be defined as above. For example, the classifier 412 may be but not limited to a neural network classifier. The classifier 412 may also be any other standard or known classifier.

In various embodiments, the map generating unit 410 may be further configured to group the plurality of pixels, and the classifier 412 may be configured to determine for each of the groups, the likelihood of a pixel therein representing a vein or a part thereof and to subsequently apply the likelihood outcome of that pixel to all pixels in that group. The plurality of pixels may be grouped as defined above.

Figure 4B:
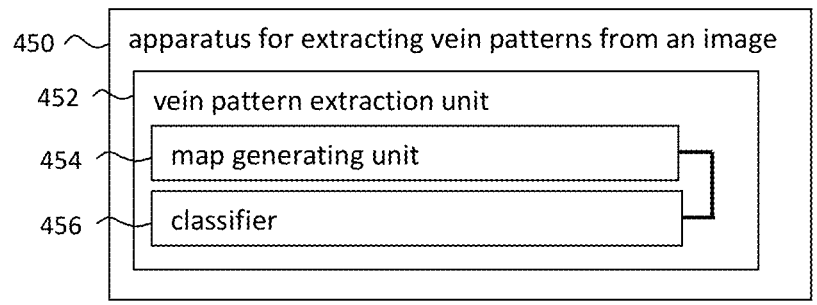

In a fourth aspect, an apparatus for extracting vein patterns from an image comprising a plurality of pixels for personal identification is provided as illustrated in FIG. 4(b). The apparatus 450 comprises a vein pattern extraction unit 452 comprising a map generating unit 454 configured to generate an orientation map for the plurality of pixels of the image; and a classifier 456 configured to determine for each of the plurality of pixels whether a pixel represents a vein or a part thereof based on the orientation map. In various embodiments, the term "image" may be as defined above.

In these embodiments, the thresholding scheme unit 414 may utilize a threshold applicable to a skin area of the image to determine the veins. The skin area of the image may be the skin area represented by a feature map. For example, the thresholding scheme unit 414 may utilize a second threshold applicable to areas around the veins determined by the first threshold to elongate the determined veins.

Figure 4C:
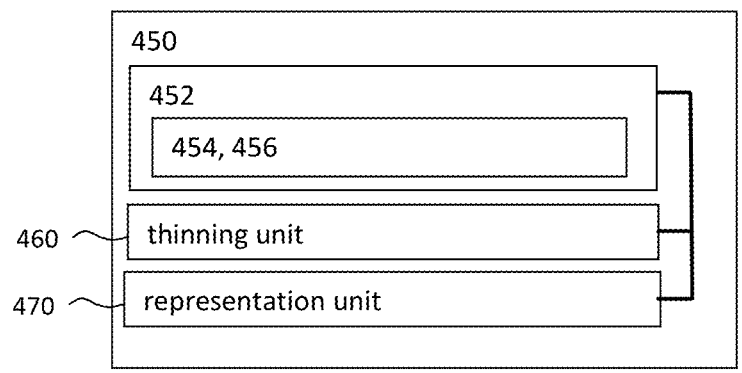

In various embodiments, the vein pattern extraction unit 408, 452 may further comprise a thinning unit 416, 460 (as shown in FIG. 4(c)) configured to obtain a skeleton of the veins using a thinning algorithm.

The apparatus 300 may further comprise an optimization unit 418 configured to precondition the colour image for the map generating unit 410, 454. For example, the optimization unit 418 may comprise an intensity adjustment unit 420 configured to explore a searching space formed by images generated from colour images, and a filter 422 configured to capture local information from the colour image such that veins are detectable from the colour image. The filter 422 may be a plurality of filters. The term "searching space" and "images" in this context may be as defined above. The intensity adjustment unit 420 may be configured to generate a new image with vein patterns from an initial image.

In some embodiments, the optimization unit 418 may further comprise an objective function evaluator 424 configured to form an objective function for the colour image.

According to various embodiments, the vein pattern extraction unit 408, 452 may further comprise a representation unit 426, 470 configured to represent the vein patterns with a set of points. The term "points" may be as defined above. In some examples, the representation unit 426, 470 may be configured to represent the vein patterns as a graph by detecting intersections and end points of the vein patterns as nodes of the graph, and links the nodes to form the graph. The representation unit 426, 470 may include additional nodes if it is determined that a curvature of a vein segment is larger than a threshold. The representation unit 426, 470 may combine vein patterns from different selected functional relationships obtained from IR images.

In various embodiments, an output of the classifier 412, 456 may allow for manual correction of the colour image. The classifier 412, 456 may be as defined above. As the classifier 412, 456 may impose errors on its output, especially in low quality images, manual correction of the output may be allowed.

In various embodiments, the apparatus 300 may further comprise an image pre-processor 428 configured to remove blocking artifacts in the colour image, wherein the colour image is a compressed colour image. The image pre-processor 428 may use a knowledge-based approach or a one-pass algorithm. The image pre-processor 428 may comprise an indexing mechanism. In a fifth aspect, the method 100, 250 or the apparatus 300, 450 in accordance to various embodiments for use in forensic identification is provided.

Figure 5A:
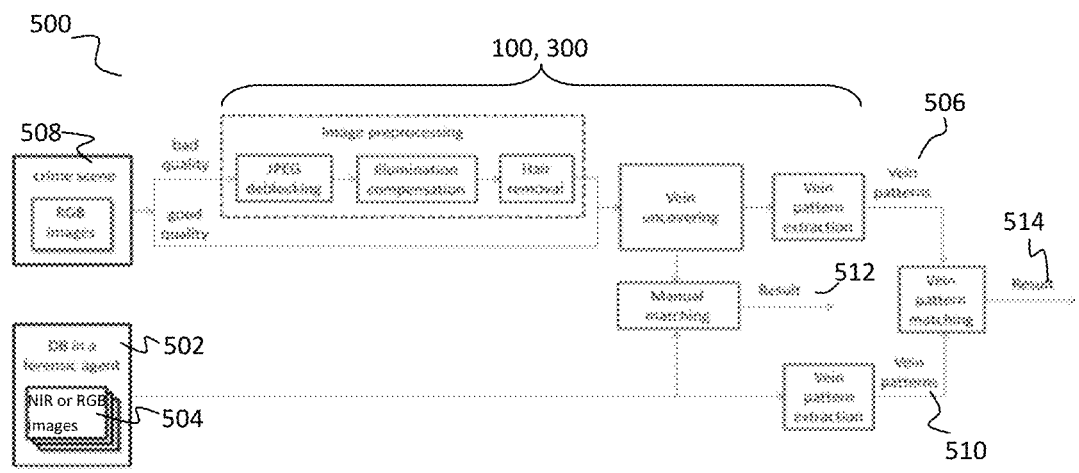
FIG. 5 shows examples of two application scenarios: (a) colour images matched with infrared images or RGB images, and (b) colour images matched with colour images, in accordance to various embodiments.

Examples of various embodiments may be applied to two scenarios illustrated in FIG. 5. The first scenario 500 as illustrated in FIG. 5(a) assumes that a database 502 containing infrared images or colour images 504 collected from persons with known identities such as previous inmates or suspects was available. In this scenario 500, vein patterns 506 extracted from digital images or evidence images 508, for example photographic images or RGB images, using the method 100 or the apparatus 300 matched with those 510 from the infrared images 504. The matching results (or matching outputs) 512, 514 may be used in two ways. RGB images may herein be interchangably referred to as colour images or black-and-white versions or greyscale versions. One, as with automatic fingerprint identification systems, was to retrieve a group of persons for further investigation. The other was to uniquely identify a person. It should be emphasized that these matchings may be performed either automatically 512 or manually 514.

Figure 5B:
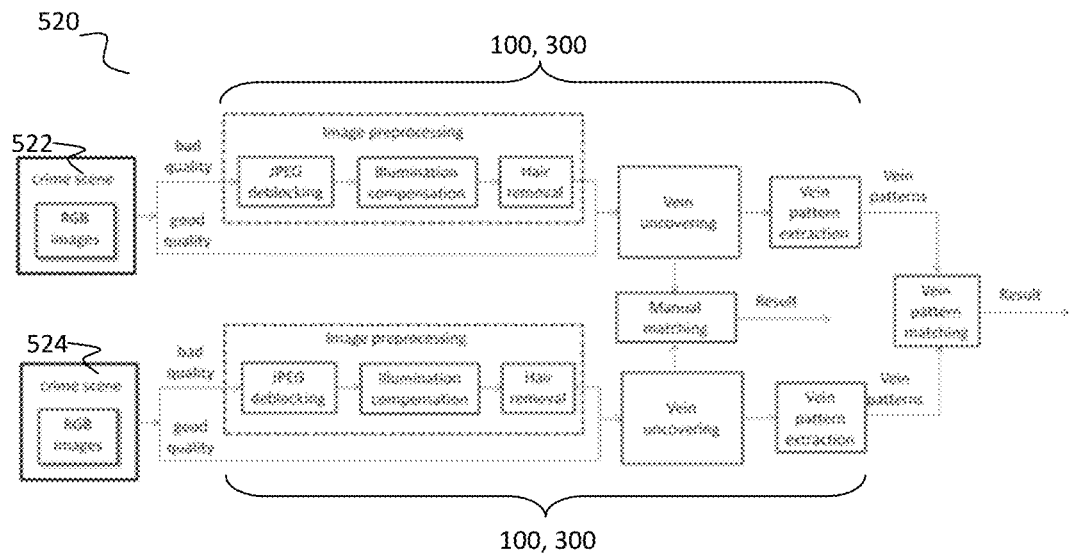
Figure 6A:
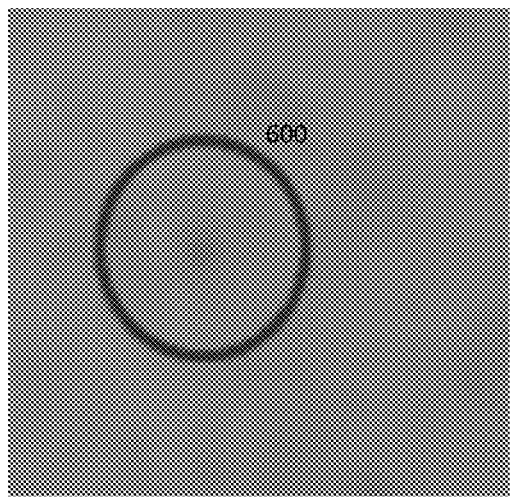
FIG. 6 shows examples of the effects of blocking artifacts on pigmented skin marks and vein patterns: (a) an uncompressed colour image with a common nevus, (b) the corresponding JPEG compressed images with compression ratios of 102.51, (c) the V component of the YUV space with a clear vein pattern, and (d) the V component of the corresponding JPEG compressed images with compression ratios of 95.63, in accordance to various embodiments.
Figure 6B:
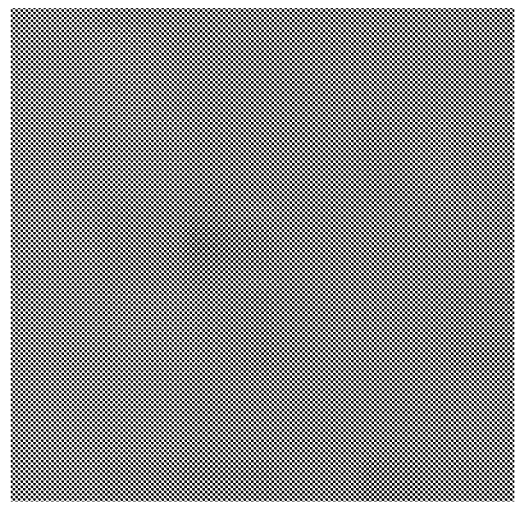
Figure 6C:
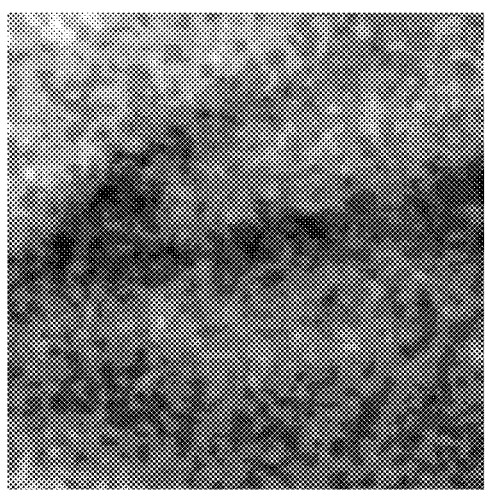
Figure 6D:

In the second scenario 520 as depicted in FIG. 5(b), vein patterns in different digital evidence images 522, 524, for example photographic images or RGB images, collected from the same/different crime scenes were processed using the method 100 or the apparatus 300 of various embodiments and were matched in order to link up criminals in different images and therefore, the connections between different cases or different evidence images were uncovered. In image preprocessing, other methods for example, super-resolution may be included.

Various embodiments have four major processing components: preprocessing, vein uncovering, vein pattern extraction, and vein pattern matching. For example, the preprocessing steps may include, but are not limited to, methods for removing JPEG blocking artifacts and hair and compensating illumination variation. These preprocessing methods may not be necessary for high quality images. They may also be applied to infrared images when it is necessary.

The vein uncovering algorithm may be used to visualize the vein patterns hidden in digital images, for example colour images. The vein pattern extraction algorithms may extract vein patterns from colour images and infrared images, and represented these extracted vein patterns in an effective manner for matching. The vein patterns may be automatically extracted. Because of the difference in image qualities and properties, these images may be required to be handled by different algorithms. The vein pattern matching algorithm may compare two vein patterns to finally produce a matching score. The vein pattern matching may be performed manually or using a pattern matching algorithm. Examples of deblocking, uncovering and extraction algorithms are described below.

EXAMPLE 1

Using a Knowledge-Based Approach to Remove Blocking Artifacts in Skin Images

Using biometric traits from the skin for criminal and victim identification highly depends on the quality of evidence images, because the size of these traits in the images is usually very small. Digital images, taken by consumer cameras, are more than often compressed by the JPEG algorithm. Blocking artifact is a problem caused by this algorithm. As a result of the compressed image, vein patterns may be broken, and skin marks may be blurred or even totally removed, especially under high compression ratios.

FIG. 6 illustrates examples of the effects of blocking artifacts on pigmented skin marks and vein patterns. FIG. 6(a) shows an uncompressed digital image, for example a colour image, with a common nevus, as indicated within a circle 600 and FIG. 6(c) shows the V component of the YUV space with a clear vein pattern, wherein the V component is used in the JPEG algorithm to transform an image from RGB space to YUV space before performing the DCT Transform. FIGS. 6(b) and 6(d) are respectively the corresponding JPEG compressed images with compression ratios of 102.51 and 95.63. As seen in FIG. 6, there may be a need to remove blocking artifacts so as to improve images before any forensic analyses.

Figure 7A:
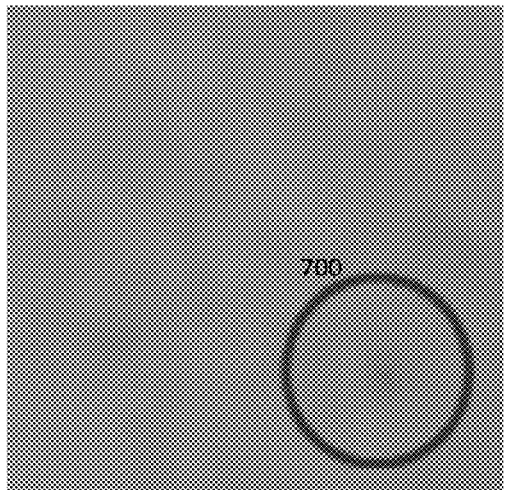
FIG. 7 shows examples of images of (a) an uncompressed digital photographic image (in colour) with a common nevus, (e) the V component of the YUV space with a clear vein pattern from a skin image, (b) the corresponding JPEG compressed image of (a) with compression ratios of 115.32, (f) the V component of the corresponding JPEG compressed images of (e) with compression ratios of 120.15, (c) the output of (b) from a post-filtering method, (g) the output of (f) from a post-filtering method, (d) the output of (b) from a MAP-based method, and (h) the output of (f) from a MAP-based method, in accordance to various embodiments.
Figure 7E:
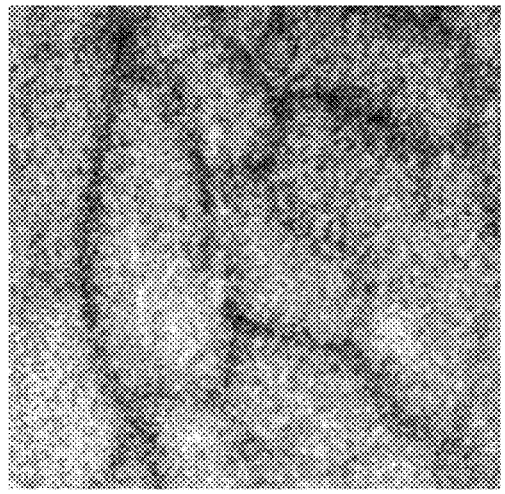
Figure 7B:
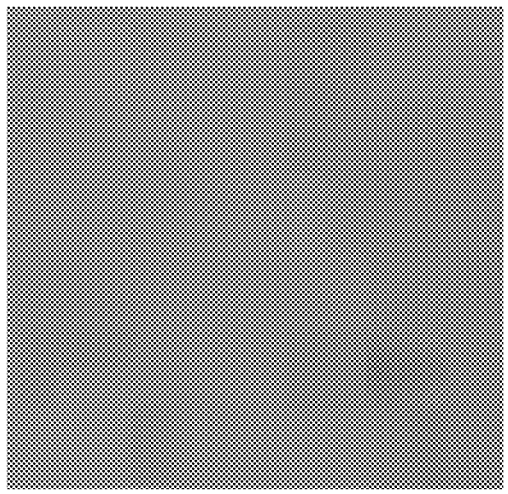
Figure 7F:
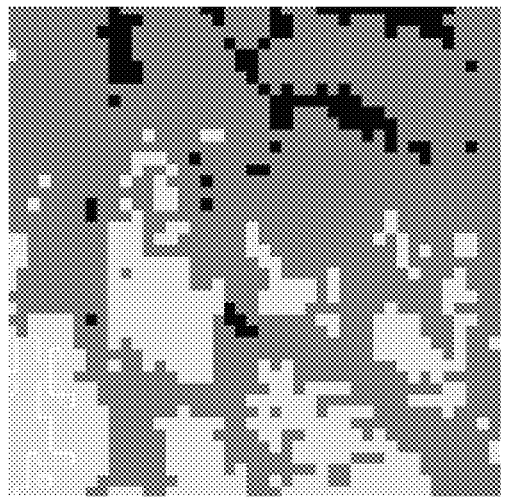
Figure 7C:
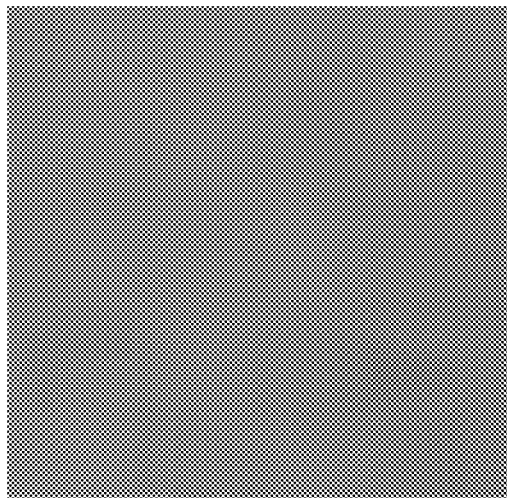
Figure 7G:
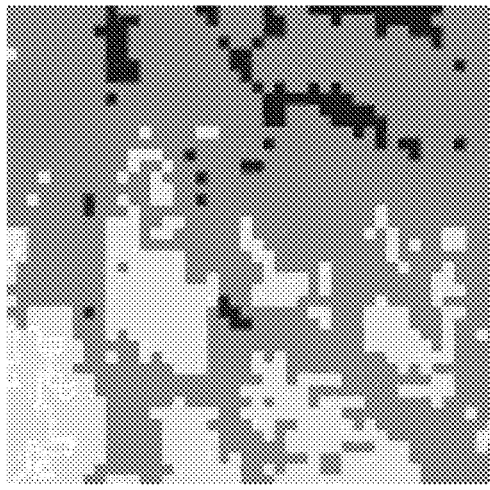
Figure 7D:
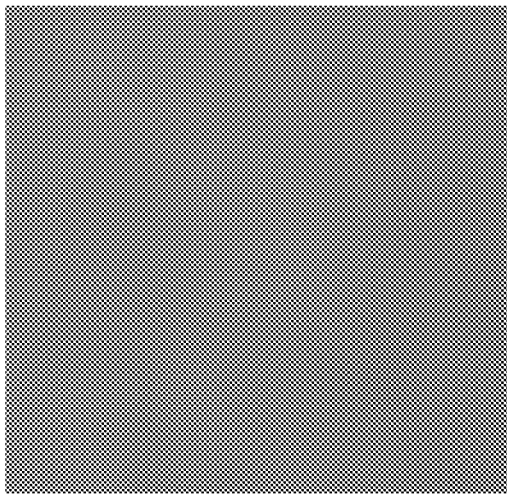
Figure 7H:
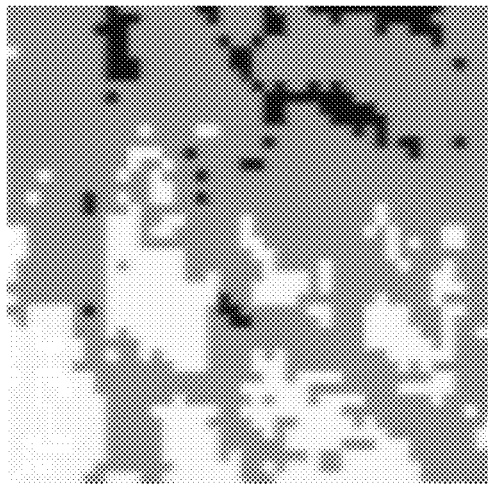

Various approaches to remove JPEG blocking artifacts were studied. The current deblocking methods have been designed for generic images, and therefore, cannot utilize prior knowledge from target images. For example, prior knowledge may include information from infrared images and/or vein patterns that may be modeled by lines and/or curves. In fact, these current methods may worsen or may have negative effect on the removal of the JPEG blocking artifacts because they generally smooth images, including biometric traits, to alleviate blocking artifacts. FIG. 7 shows examples of resultant images from some of these methods. FIG. 7(a) shows an uncompressed digital photographic image (in colour) with a common nevus as indicated within a circle 700 and FIG. 7(e) shows the V component of the YUV space with a clear vein pattern. FIGS. 7(b) and 7(f) show respectively the corresponding JPEG compressed images with compression ratios of 115.32 and 120.15. FIGS. 7(c) and 7(g) show respectively the outputs of FIG. 7(b) and FIG. 7(f) from a post-filtering method (Y. Luo and R. K. Ward, "Removing the blocking artifacts of block-based DCT compressed images", *IEEE TIP*, vol. 12, no. 7, pp. 838-842, 2003). FIGS. 7(d) and 7(h) show respectively the outputs of FIG. 7(b) and FIG. 7(f) from a MAP-based method (D. Sun and W. Chan, "Postprocessing of low bit-rate block DCT coded images based on a fields of experts prior", *IEEE TIP*, vol. 16. no. 11, pp. 2743-2751, 2007). In addition, the difference between original (uncompressed) images and their resultant images may be even larger than that between original images and compressed images in terms of quantized Discrete Cosine Transform (QDCT) coefficients.

To overcome at least the problems mentioned above for the deblocking approaches, a new approach was developed to remove blocking artifacts in skin images. A non-parametric approach to extract prior knowledge, i.e., the block relationship between compressed blocks and their original counterparts, and the neighbourhood relationship among adjacent original blocks was used. Two different algorithms, as described below, were developed to make inferences based on this prior knowledge. The first one used a Markov model and the belief propagation algorithm. This algorithm may be more accurate but may require more time. The second approach was faster and was a one-pass algorithm utilizing spatial and frequency relationships simultaneously. An indexing mechanism to improve the speed of the algorithms was also used.

Prior Knowledge in Skin Images

To exploit prior knowledge in skin images, a large database composed of skin images collected from different body sites, including the hand, arm, foot, leg, chest and back was constructed. The database was divided into a training set and two testing sets. Prior information was extracted from the training set to develop the KB approach and then the testing sets were used to evaluate its function.

Database

The database consisted of two parts. The first part (Asian database) was collected in Singapore from 97 Asians with both genders and diverse ages, occupations, and body mass indices (BMI). The ethnic groups included Chinese, Malay, Indian, and Javanese. aged between about 12 and 70 years old. Their occupations included students, professors, and manual workers, and their BMIs range from about 18 to about 40. The camera model was Nikon D70s, and the images were taken under normal daylight or fluorescent light.

The second part (Caucasian database) was collected in the United States from 10 Caucasians under Institutional Review Board approval from the Los Angeles Biomedical Research Institute. The camera model was Nikon D80, and the imaging configuration such as illumination and image distance was also different from the settings in Singapore.

Images from 71 randomly selected subjects in the Asian database were used to form a training set. The remaining 26 subjects' images comprised the first testing set. The images in the Caucasian database comprised the second testing set. Each set contained images of participants from both genders and all age groups. These images were stored in the JPEG format with a very high quality factor and without noticeable blocking artifacts. The original images from the cameras are herein referred to as uncompressed images.

For the training set, because a large part of the raw images was considered to be the background, sub-images with 256× 256 pixels containing only areas of visible skin were cropped. This relatively small size was chosen to reduce redundant information and to improve the speed of the algorithms. Then, the JPEG standard were used to compress the sub-images resulting in image pairs. Each pair had one original skin image and the corresponding JPEG compressed image. After cropping, the training set contained 5,662 image pairs.

FIG. 8 illustrates (a) a raw image and (b), (f) a pair of skin sub-images obtained. FIG. 8(a) shows a raw image of the inner right forearm of a male (Chinese, 52 years old, BMI=25), and FIG. 8(b) shows the skin image cropped from the indicative rectangle 800 in FIG. 8(a). FIGS. 8(c), 8(d) and 8(e) show the Y, U and V components of FIG. 8(b). FIG. 8(f) shows the JPEG compressed image of FIG. 8(b) with the compression ratio of 41.98. FIGS. 8(g), 8(h) and 8(i) show the Y, U and V components of FIG. 8(f).

The KB approach was operated in the YUV space because the JPEG compression was performed in this space. FIG. 8(h) and FIG. 8(i) show that the blocking artifacts in the U and V components are more significant. These artifacts were caused primarily because of the down-sampling process in the JPEG algorithm and because of larger quantization steps. By further cutting the image pairs into 8×8 pixel blocks, 5,797,888 block pairs were present in the training set. By choosing different compression quality factors, different training sets were then obtained.

For the first testing set, 500 skin sub-images with size of 448×512 or 512×448 pixels from the raw images of the 26 Asian subjects were cropped. The larger sizes were chosen in order to cover more skin features.

For the second testing set, 262 skin sub-images with size of 256×256 pixels from the raw images of the 10 Caucasians were cropped. Because Caucasians typically have more pigmented skin marks, the second testing set was used to evaluate the performance of the KB approach on skin marks. The smaller size was chosen so that skin marks may be more easily observed.

Training Blocks or Sets

An original block (or may be interchangably referred to "set") and its compressed output have the same Discrete Cosine Transform (QDCT) coefficients. In general, only several coefficients in the upper left corner of a QDCT matrix are non-zero integers, which are referred to as effective coefficients, used to form an index vector.

Figures 9, 11:
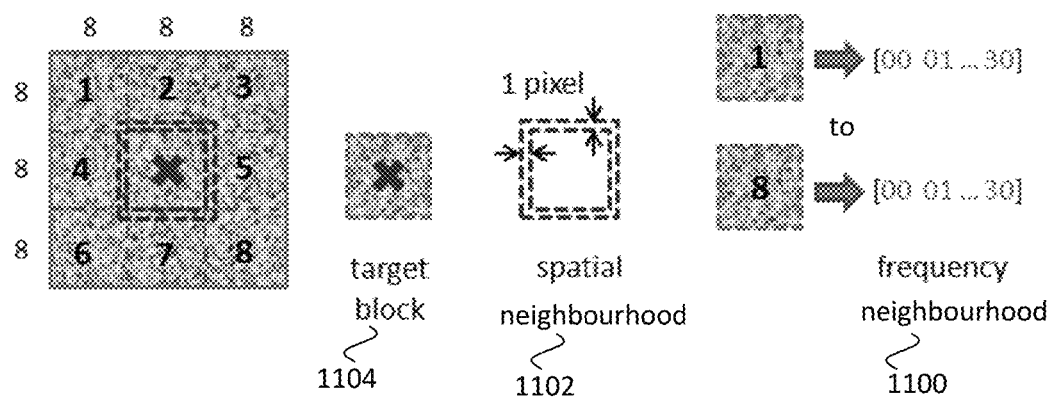
FIG. 9 shows an example of a QDCT coefficient matrix, the effective coefficients, and the corresponding index vector, in accordance to various embodiments.
FIG. 11 shows a schematic representation of spatial and frequency neighbourhoods, in accordance to various embodiments.

FIG. 9 illustrates an example of a QDCT coefficient matrix, the effective coefficients, and the corresponding index vector. As the quantization was a many-to-one mapping, different original blocks (or sets) may have the same QDCT coefficients and index vector.

Figure 10A:
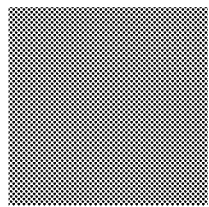
FIG. 10 shows (a) a compressed block (or set) in the V component, (b) to (s) examples of original blocks which have been compressed to (a), in accordance to various embodiments.
Figure 10B:
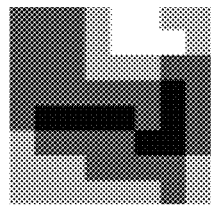
Figure 10C:
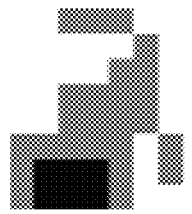
Figure 10D:
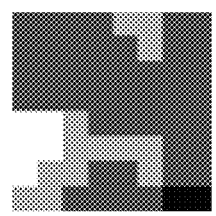
Figure 10E:
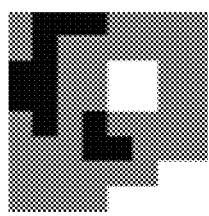
Figure 10F:
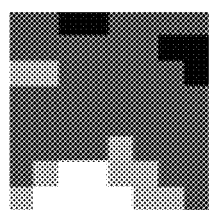
Figure 10G:
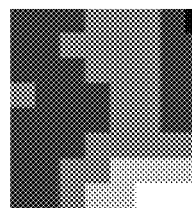
Figure 10H:
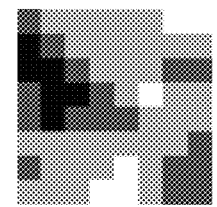
Figure 10I:
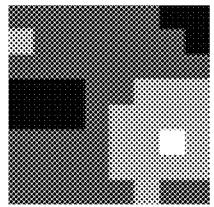
Figure 10J:
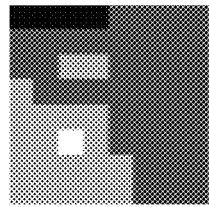
Figure 10K:
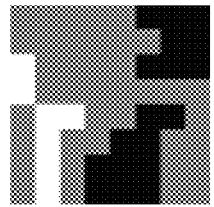
Figure 10L:
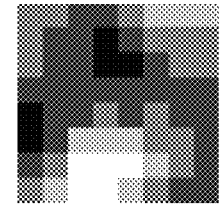
Figure 10M:
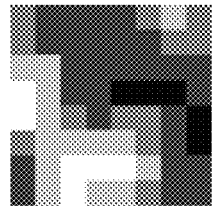
Figure 10N:
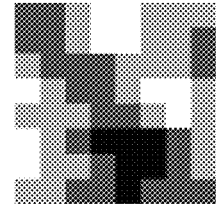
Figure 10O:
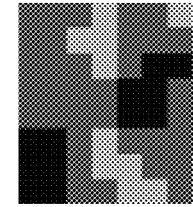
Figure 10P:
Figure 10Q:
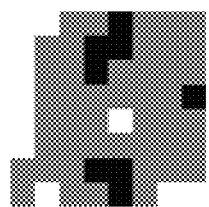
Figure 10R:
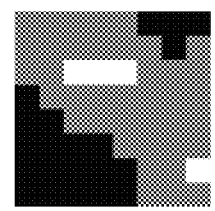
Figure 10S:
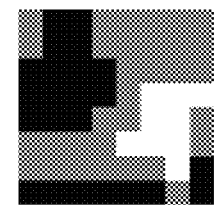

FIG. 10(a) shows a compressed block (or set) in the V component. FIGS. 10(b) to 10(s) show examples of original blocks which have been compressed to FIG. 10(a).

All their index vectors were [13 0 0 0 0 0 0 0 0], where only the DC term was non-zero and therefore, the image in FIG. 10(a) had only one intensity value. This many-to-one block relationship implied that only the local information inside one block was not sufficient to uniquely determine corresponding original blocks. The relationship between neighbouring blocks may be considered.

For each original block, two neighbourhoods were defined, namely a frequency neighbourhood 1100 which was composed by the index vectors of 8 neighbouring blocks, and a spatial neighbourhood which was composed by the 36 pixels in the same 8 neighbouring blocks which were connected with the target block (as illustrated in FIG. 11).

These original blocks and the neighbourhood relationships represented prior knowledge in skin images and were extracted from the training set to infer original blocks (sets) in evidence images. Two algorithms were developed to make inference.

Two Inference Algorithms Based on Prior Knowledge

The two algorithms to make inference based on prior knowledge were as follow:—one was based on a Markov model, while the other was a one-pass algorithm. To speed up these two algorithms, an indexing mechanism was also developed.

Algorithm based on a Markov Model

Figure 12:
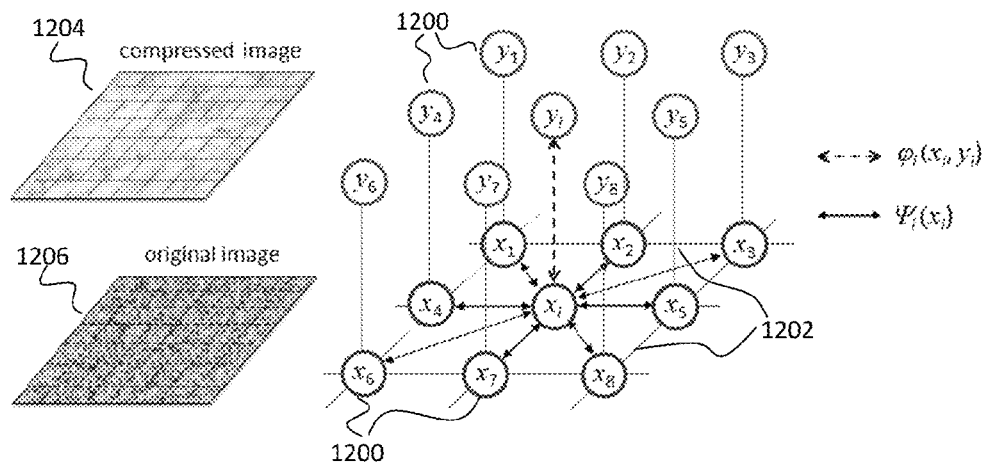
FIG. 12 shows a schematic representation of a Markov network model, in accordance to various embodiments.

The first algorithm used the traditional Markov model illustrated in FIG. 12, where the circles 1200 represent network nodes, and the lines 1202 indicate statistical dependencies between nodes. Let compressed blocks (or sets) 1204 be observation nodes, y, and original blocks (or sets) 1206 with corresponding QDCT coefficients be the different states of hidden nodes, x, which required estimation. For this network, the probability of any choice of original blocks was proportional to the product of functions $\phi_i(x_i,y_i)$ relating each observation to the underlying hidden states, and compatibility functions $\psi_i(x_i)$ relating the possible states of neighbouring hidden nodes:

$$P(x|y) \propto \prod_i \varphi_i(x_i, y_i) \prod_i \psi_i(x_i). \tag{1}$$

The function $\phi_i(x_i,y_i)$ may be specified by the JPEG compression algorithm:

$$\phi_i(x_i,y_i)=\delta\{Q[DCT(x_i)]-Q[DCT(y_i)]\}, \tag{2}$$

where DCT(·) represents the DCT transform, Q[·] is the quantization operator, and $\delta$ is a delta function. The function $\psi_i(x_i)$ represents the spatial compatibility between neighbouring original blocks. Let $p_{ij}{}^s$ be pixels in the spatial neighbourhood 1102 (reference to FIG. 11) of the block i which overlap with the neighbouring block j (j∈N(i), where N(i) is the 8 neighbours of block i). Let $p_{ji}$ be pixels in the neighbouring block j which overlap with the spatial neighbourhood 1102 of block i. The compatibility function may be defined as:

$$\psi_i(x_i) = \exp\left(-\frac{\left[\sum_{j\in N(i)}|p_{ij}^s - p_{ji}|\right]^2}{2\sigma^2}\right). \tag{3}$$

The optimal original blocks may be a collection that maximizes the probability of the Markov network. Finding the global optimal solution may be computationally intractable, so the belief propagation may be used to obtain a suboptimal solution.

FIG. 13 illustrates examples of the performance of the algorithm based on the Markov model. FIG. 13(a) shows the V component of an original skin sub-image where one can observe a patterned distribution of hemoglobin in the veins of the skin. However, in the compressed image, the pattern was destroyed (reference to FIG. 13(b)). The belief propagation was used to infer original blocks. At the beginning (i.e., zero iteration), a resultant image consisted of the original blocks in the training set which had the same index vectors as the compressed blocks. Spatial smoothness was not considered in this initialization. As there may be more than 10,000 candidate blocks corresponding to one compressed block, frequency neighbourhoods 1100 (reference to FIG. 11) were used as a constraint to reduce the searching range. However, the outcome remained noisy and had many repeated blocks (reference to FIG. 13(c)). A high compression ratio of 86.92 produced large areas with the same intensity value (reference to FIG. 13(b)) leading to this effect. In the following iterations, more than half of these estimated blocks were subsequently corrected by the belief propagation based on spatial smoothness constraints. It quickly converged after about four to five iterations and significantly improved the quality of the outcome (reference to FIGS. 13(d)-13(h)). The vein pattern in the skin was successfully recovered, and the blocking artifacts were completely removed.

One-Pass Algorithm

In general, although the belief-propagation algorithm converges quickly, several iterations are still required to produce a satisfactory result. A one-pass algorithm was therefore developed to infer original blocks (or sets) based on combined spatial and frequency information.

Figure 14:
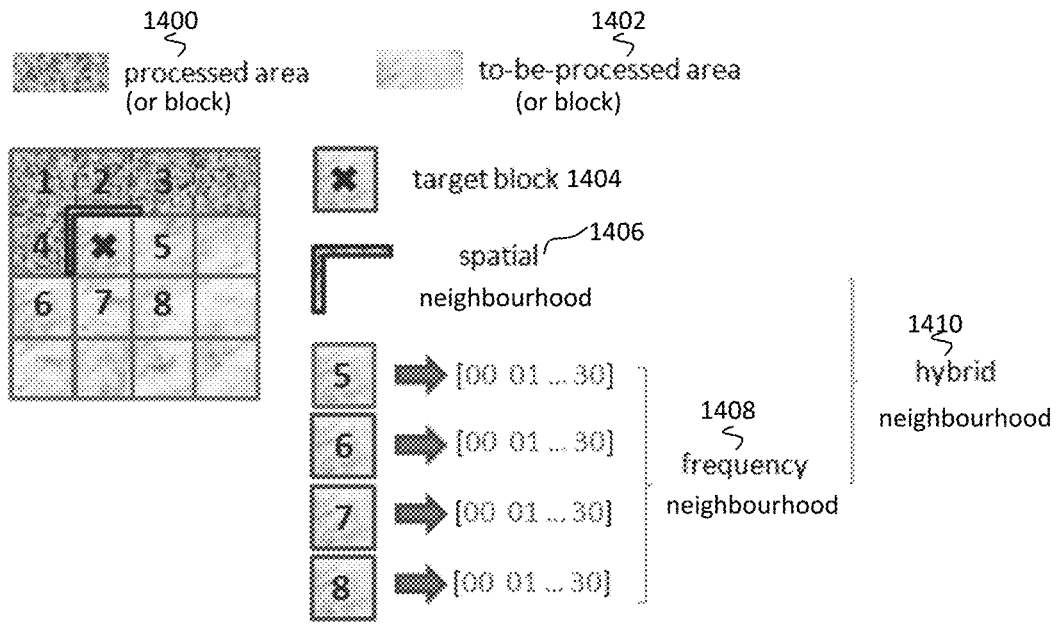
FIG. 14 shows a schematic representation of a hybrid neighbourhood in a testing process, in accordance to various embodiments.
Figure 15:
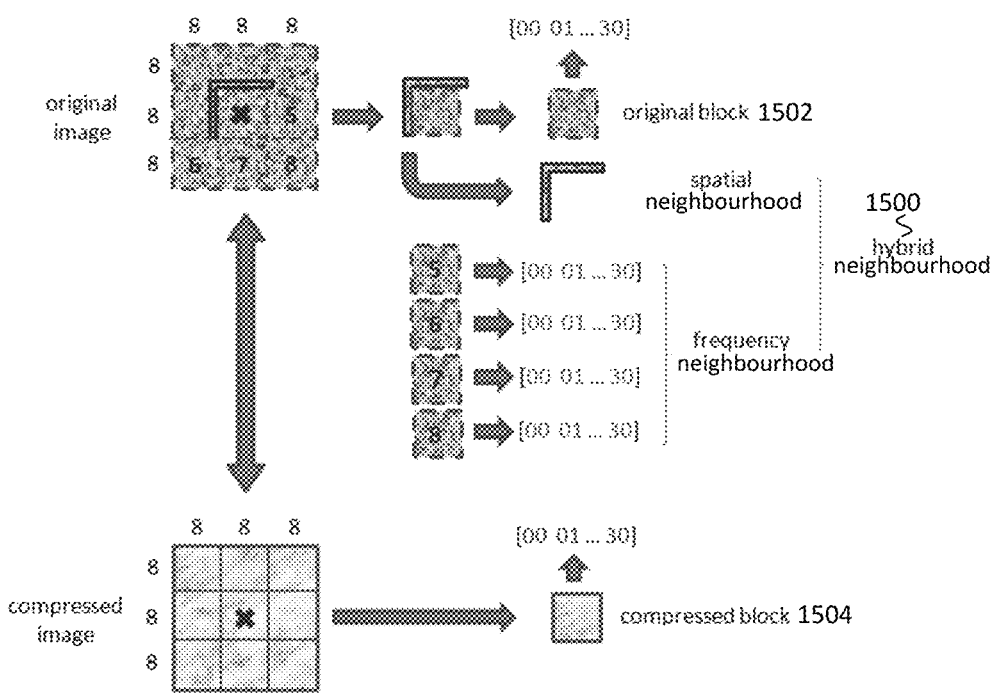
FIG. 15 shows a schematic representation of a hybrid neighbourhood in a training set construction, in accordance to various embodiments.

Assume that a compressed image was processed block by block in a raster-scan order (i.e., from left to right and from top to bottom). For a compressed block target, three upper and one left neighbouring blocks were processed as illustrated in an example of FIG. 14). The spatial information in the processed blocks 1400 (i.e., blocks 1-4 in FIG. 14) and the frequency information in the to-be-processed blocks 1402 (i.e., blocks 5-8 in FIG. 14) were used as smooth constraints to search for the best original block in the training set. The pixels in the processed blocks 1400 that were connected to a target block 1404 represented a spatial neighbourhood 1406. The index vectors of the to-be-processed blocks 1402 represented a frequency neighbourhood 1408. Together these formed a "hybrid neighbourhood" 1410 of the target block 1404. Thus, each original block in the training set had a hybrid neighbourhood 1500 determined from the source (i.e., the original) image (as seen in FIG. 15). For example, the hybrid neighbourhood 1500 may be formed similarly to the hybrid neighbourhood 1410. In this configuration of FIG. 15, each record in the training set contained an original block 1502, its hybrid neighbourhood 1500, and its compressed block 1504.

In the testing stage, for a target block w, its index vector was used to find a group of candidate original blocks, G(w) ={z|QDCT[z]=QDCT[w]}. Then an optimal candidate was searched according to the hybrid neighbourhood of the target block. This search was carried out in two steps. Firstly, the frequency neighbourhood was used to narrow down the group:

$$G'(w)=\{u\in G(w)|F_w=F_u\}, \tag{4}$$

where $F_w(F_u)$ represents the frequency neighbourhood of w(u). If the group was an empty set, 20 candidate blocks were searched from G(w) whose frequency neighbourhoods were the nearest to $F_w$ to form G'. Then the spatial neighbourhood was used to find the optimal original block t*:

$$t^* = \underset{t\in G'(w)}{\operatorname{argmin}} d(S_t, S_w), \tag{5}$$

where $S_w(S_t)$ represents the spatial neighbourhood of w(t), and d represents L1-norm.

Figure 13A:
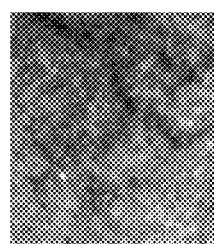
FIG. 13 shows (a) the V component of an original skin sub-image, (b) a compressed version of (a) with the compression ratio of 86.92, (c)-(h) respectively the outputs after 0, 1, 3, 6, 9 and 18 iterations using the Markov model algorithm based on belief propagation, in accordance to various embodiments.
Figure 13B:
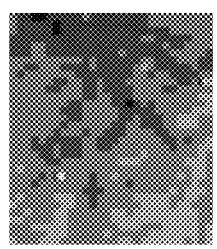
Figure 13C:
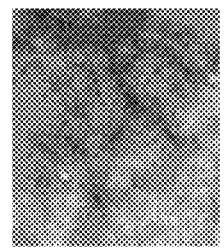
Figure 13D:
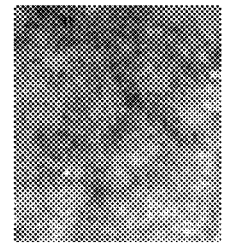
Figure 13E:
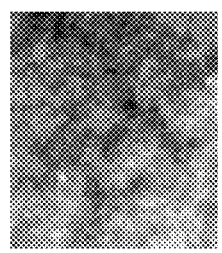
Figure 13F:
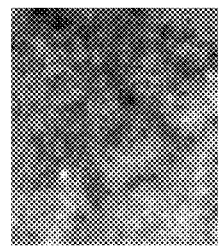
Figure 13G:
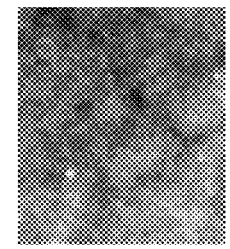
Figure 13H:
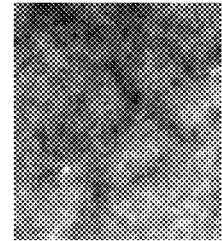
Figures 16A, 16B, 16C, 16D:
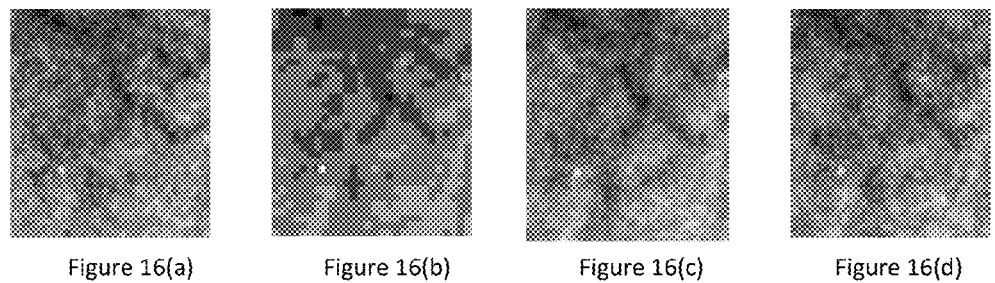
FIG. 16 shows (a) the V component of an original skin sub-image, (b) a compressed version of (a) with the compression ratio of 86.92, (c) the output using the Markov model algorithm, and (d) the output using the one-pass algorithm, in accordance to various embodiments.

To compare the one-pass algorithm with the algorithm based on the Markov model, the same testing image (reference to FIG. 13(b)) was used to evaluate the one-pass algorithm (reference to FIG. 16). Theoretically, the outcome from the Markov model based algorithm should be more accurate because it optimizes the probability in Eq. (1). However, FIG. 16(c) and FIG. 16(d) demonstrate that the difference between the two outcomes are difficult to discern with normal human vision.

The one-pass algorithm had similar performance but was much faster than the belief propagation. Thus, the one-pass algorithm was used for the following evaluations.

Figure 17:
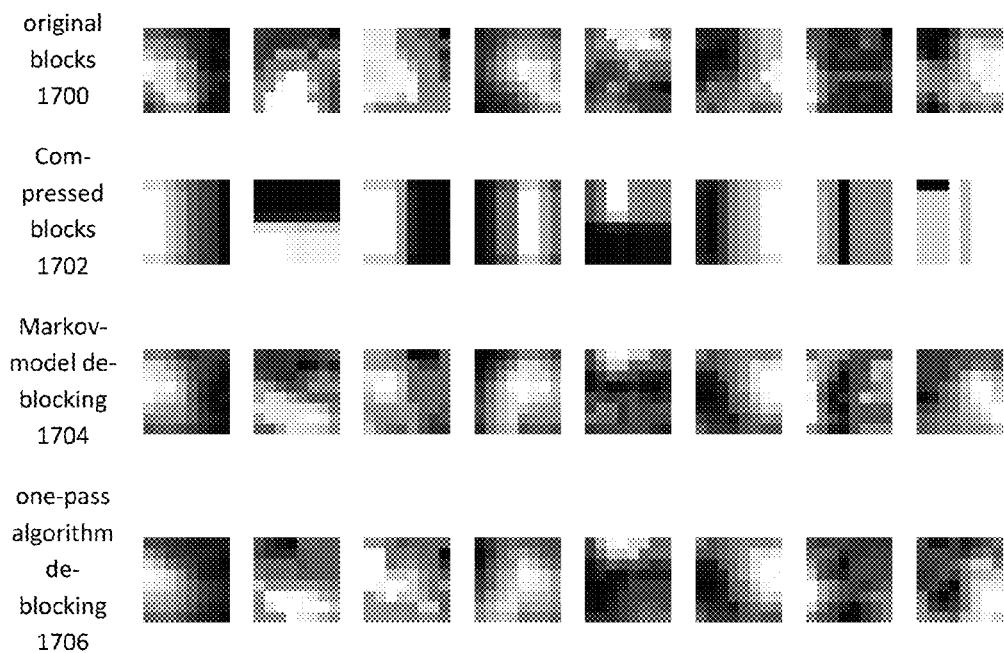
FIG. 17 shows images of corresponding blocks (or sets), in accordance to various embodiments.
Figure 18A:
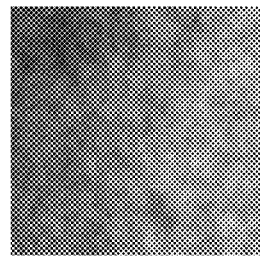
FIG. 18 shows evaluation of deblocking performance in the Y component of (a) an original images, (b) the compressed image, (c) the image from FOE method, (d) the image from SADCT method, (e) the image from ADPROC method, (f) the image from NLF method, and (g) from the KB approach, in accordance to various embodiments.
Figure 18B:
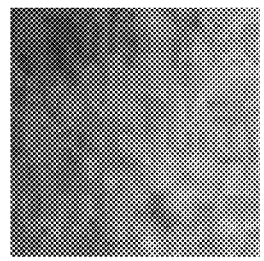
Figure 18C:
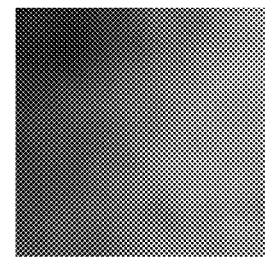
Figure 18D:
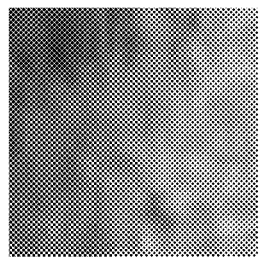
Figure 18E:
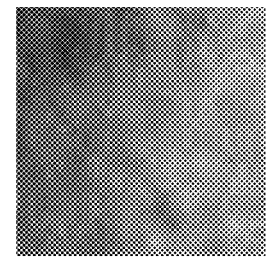
Figure 18F:
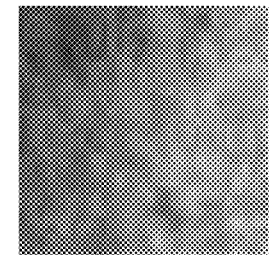
Figure 18G:
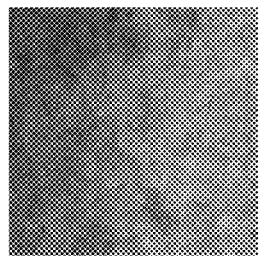
Figure 19A:
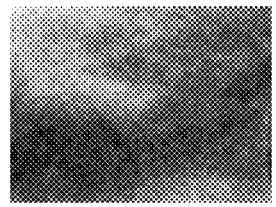
FIG. 19 shows evaluation of deblocking performance in the U component of (a) an original image, (b) the compressed image, (c) the image from FOE method, (d) the image from SADCT method, (e) the image from ADPROC method, (f) the image from NLF method, and (g) from the KB approach, in accordance to various embodiments.
Figure 19B:
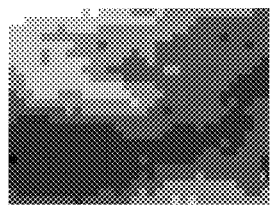
Figure 19C:
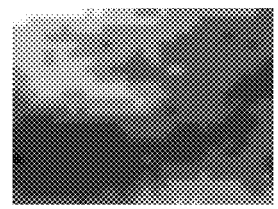
Figure 19D:
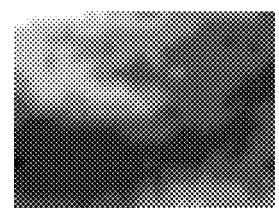
Figure 19E:
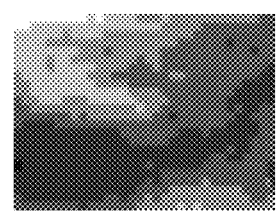
Figure 19F:
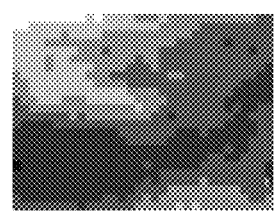
Figure 19G:
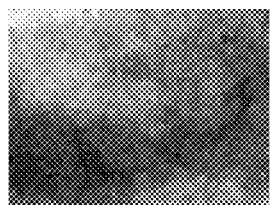
Figure 20A:
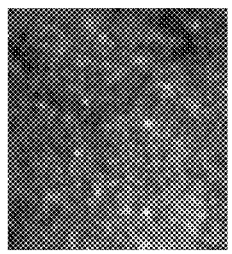
FIG. 20 shows evaluation of deblocking performance in the V component of (a) an original image, (b) the compressed image, (c) the image from FOE method, (d) the image from SADCT method, (e) the image from ADPROC method, (f) the image from NLF method, and (g) from the KB approach, in accordance to various embodiments.
Figure 20B:
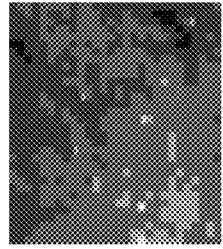
Figure 20C:
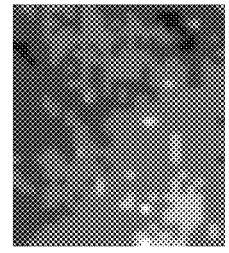
Figure 20D:
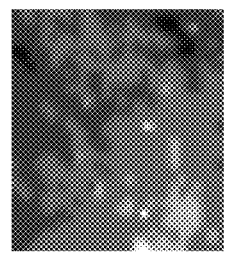
Figure 20E:
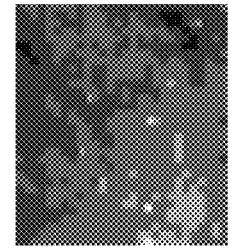
Figure 20F:
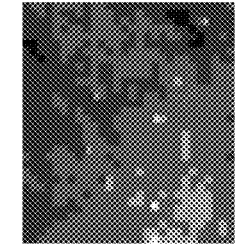
Figure 20G:
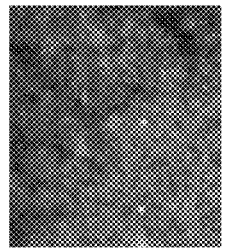
Figure 21A:
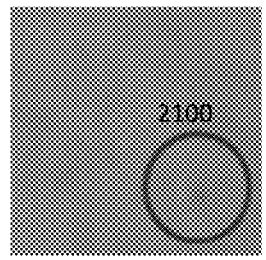
FIG. 21 shows evaluation of deblocking performance on digital photographic images (in colour) of (a) the original image, (b) the compressed image, (c) the image from FOE method, (d) the image from SADCT method, (e) the image from ADPROC method, (f) the image from NLF method, and (g) the image from the KB approach, in accordance to various embodiments.
Figure 21B:
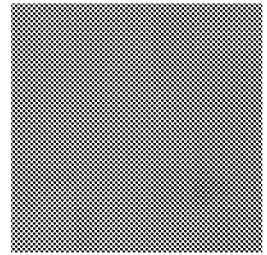
Figure 21C:
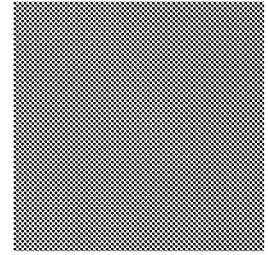
Figure 21D:
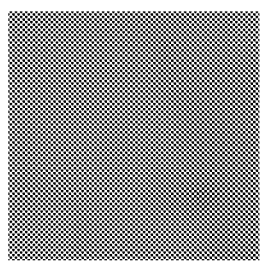
Figure 21E:
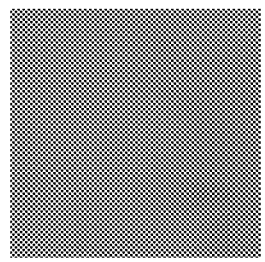
Figure 21F:
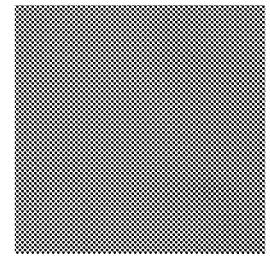
Figure 21G:
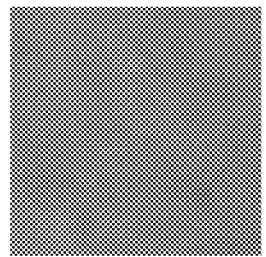
Figure 22A:
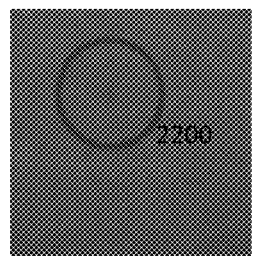
FIG. 22 shows evaluation of deblocking performance on digital photographic images (in colour) of (a) the original image, (b) the compressed image, (c) the image from FOE method, (d) the image from SADCT method, (e) the image from ADPROC method, (f) the image from NLF method, and (g) the image from the KB approach, in accordance to various embodiments.
Figure 22B:
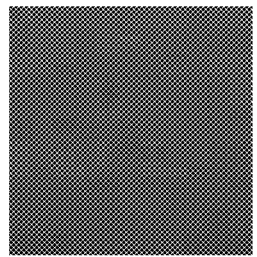
Figure 22C:
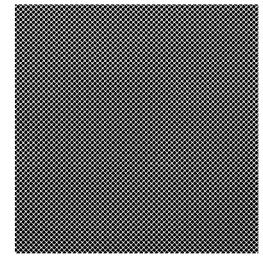
Figure 22D:
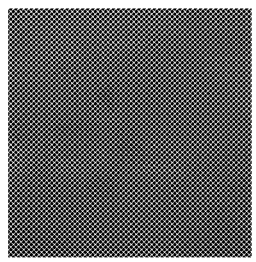
Figure 22E:
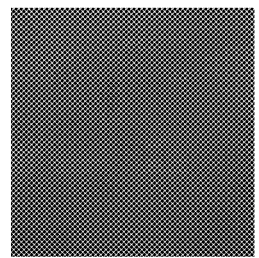
Figure 22F:
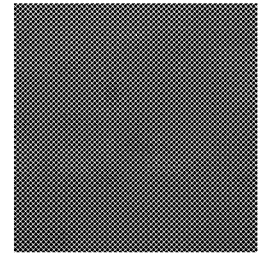
Figure 22G:
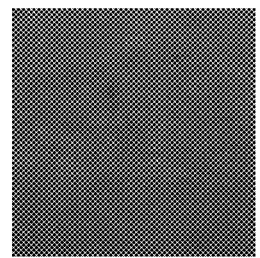
Figure 23A:
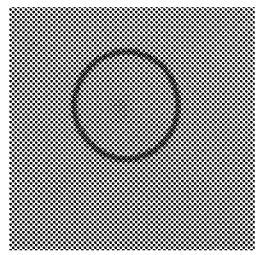
FIG. 23 shows evaluation of deblocking performance on digital photographic images (in colour) of (a) the original image, (b) the compressed image, (c) the image from FOE method, (d) the image from SADCT method, (e) the image from ADPROC method, (f) the image from NLF method, and (g) the image from the KB approach, in accordance to various embodiments.
Figure 23B:
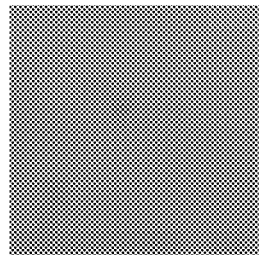
Figure 23C:
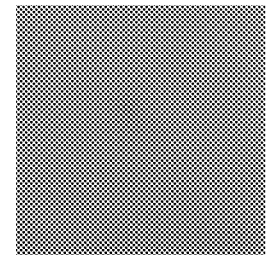
Figure 23D:
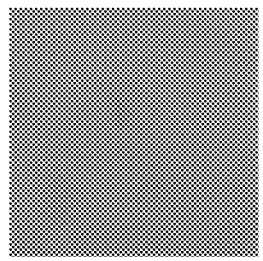
Figure 23E:
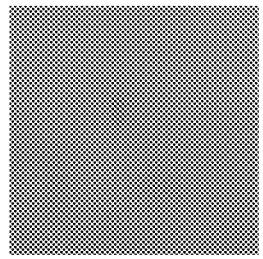
Figure 23F:
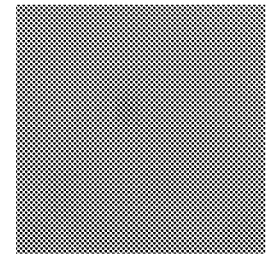
Figure 23G:
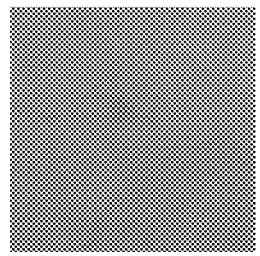
Figure 24A:
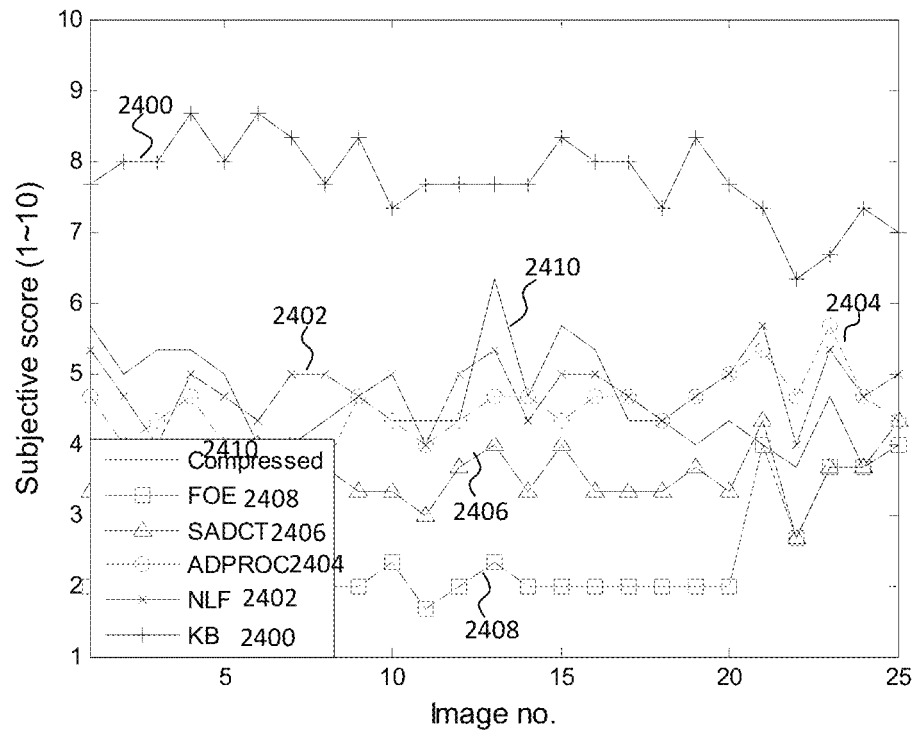
FIG. 24 shows a graphic representation of the average scores from the dermatological professionals: (a) Y component, (b) U component, (c) V component, and (d) digital photographic image (in colour), in accordance to various embodiments.
Figure 24B:
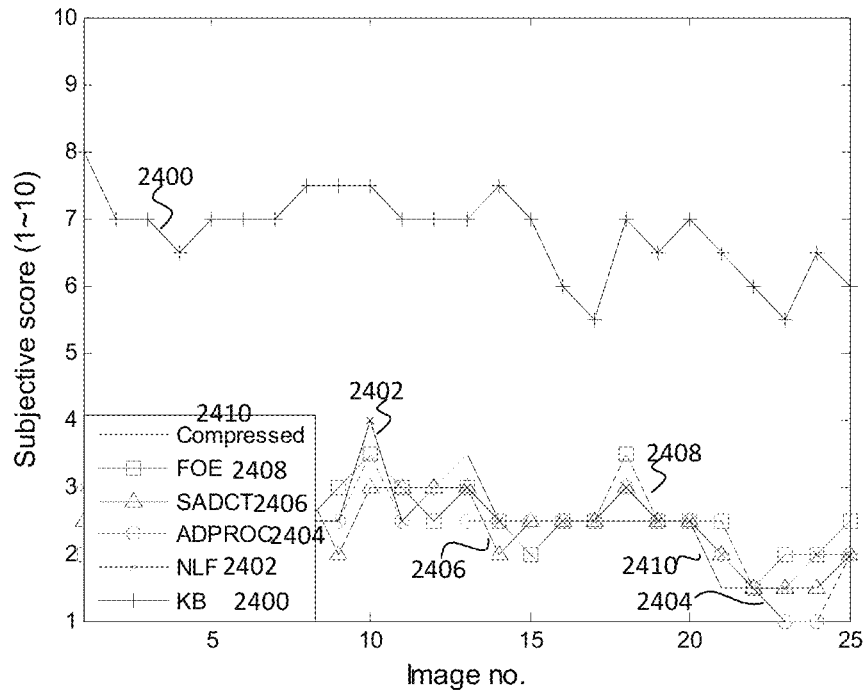
Figure 24C:
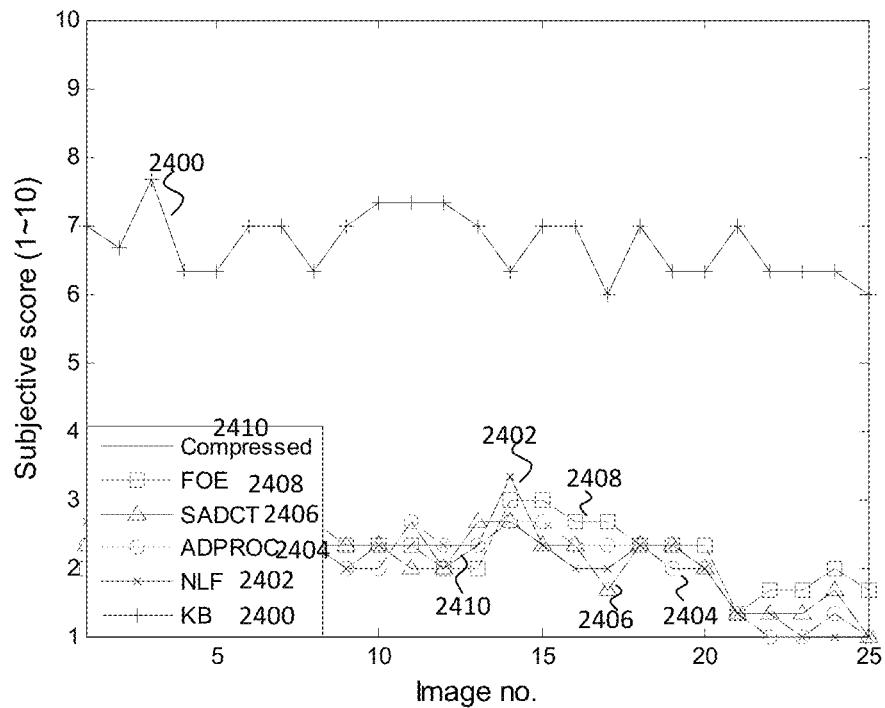
Figure 24D:
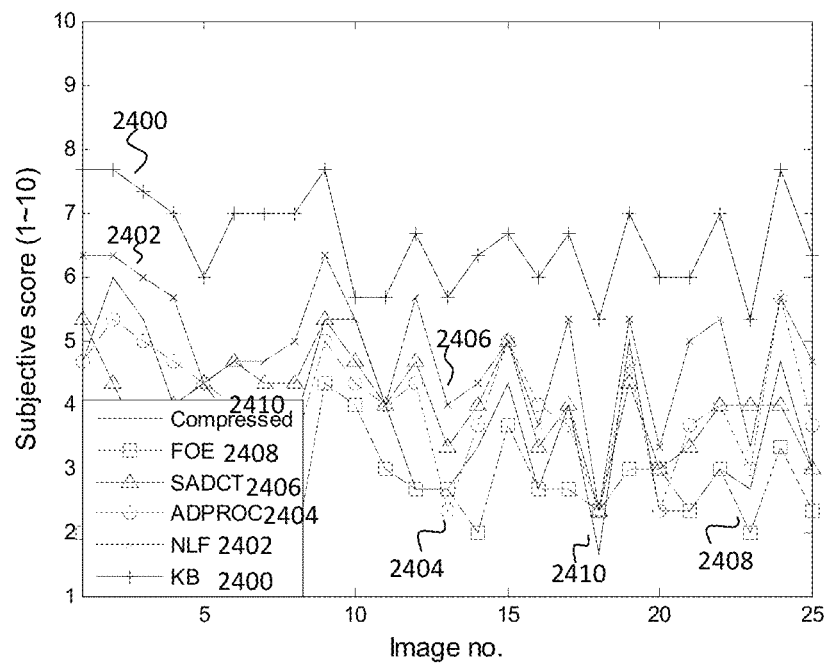
Figure 25A:
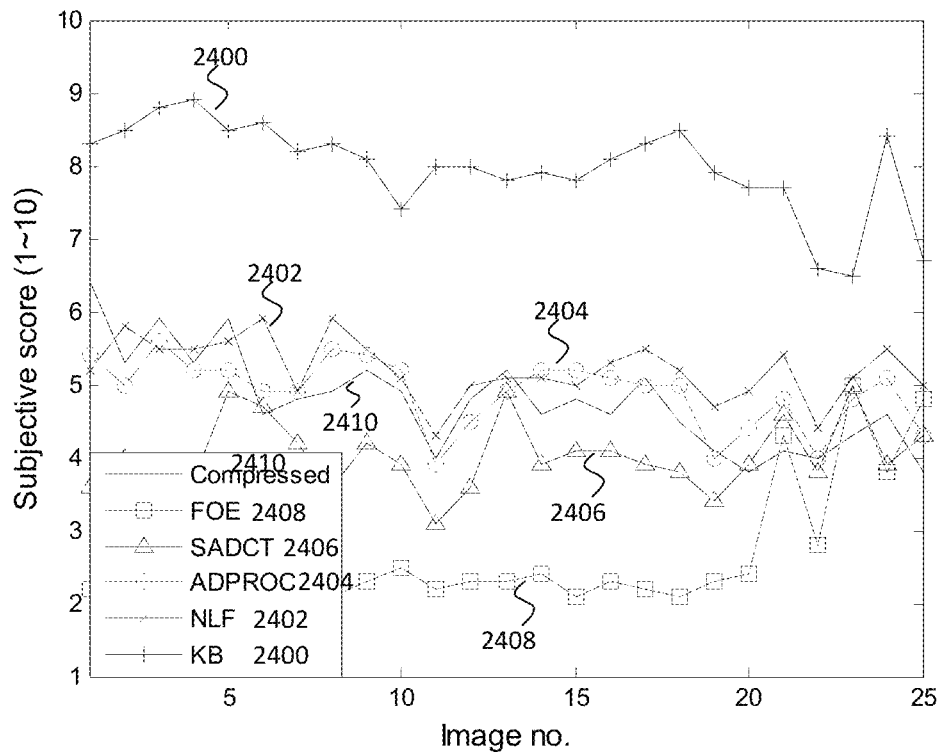
FIG. 25 shows a graphic representation of the average scores from the other participants: (a) Y component, (b) U component, (c) V component, and (d) digital photographic image (in colour), in accordance to various embodiments.
Figure 25B:
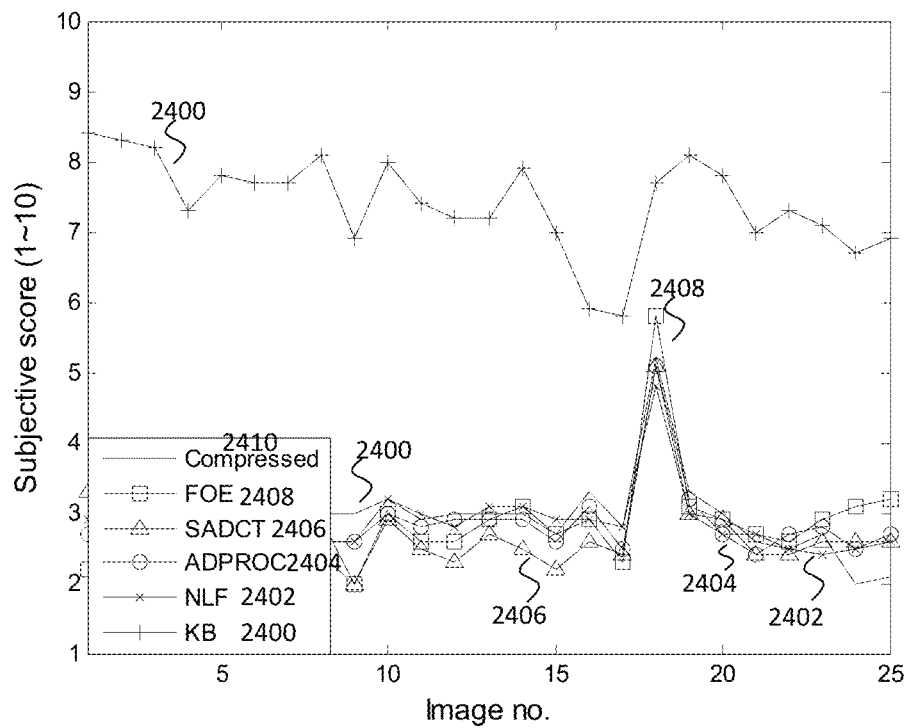
Figure 25C:
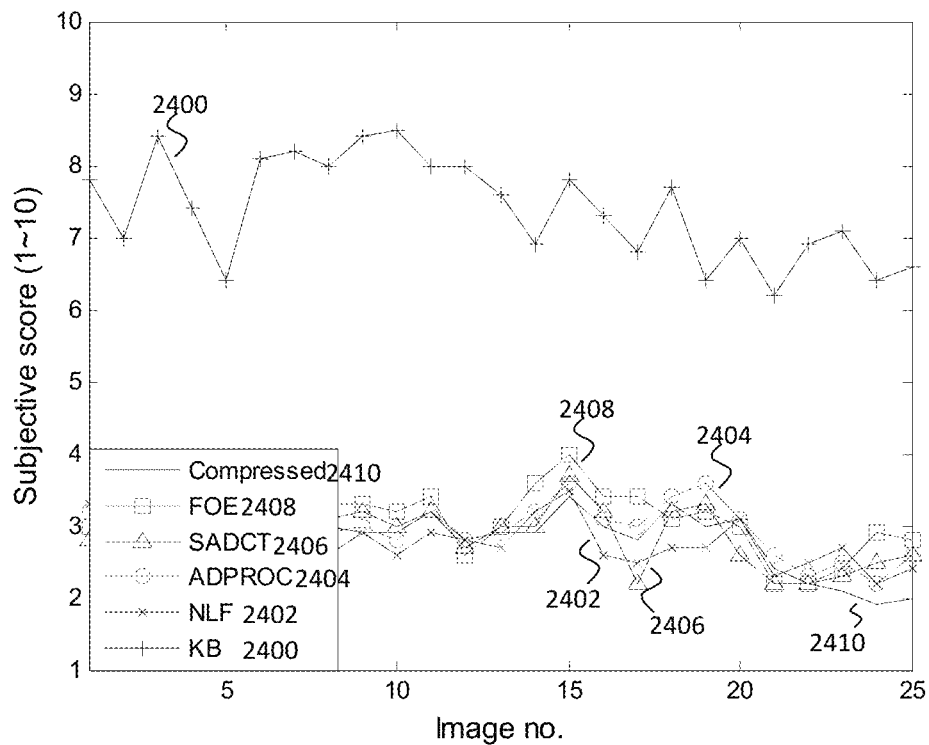
Figure 25D:
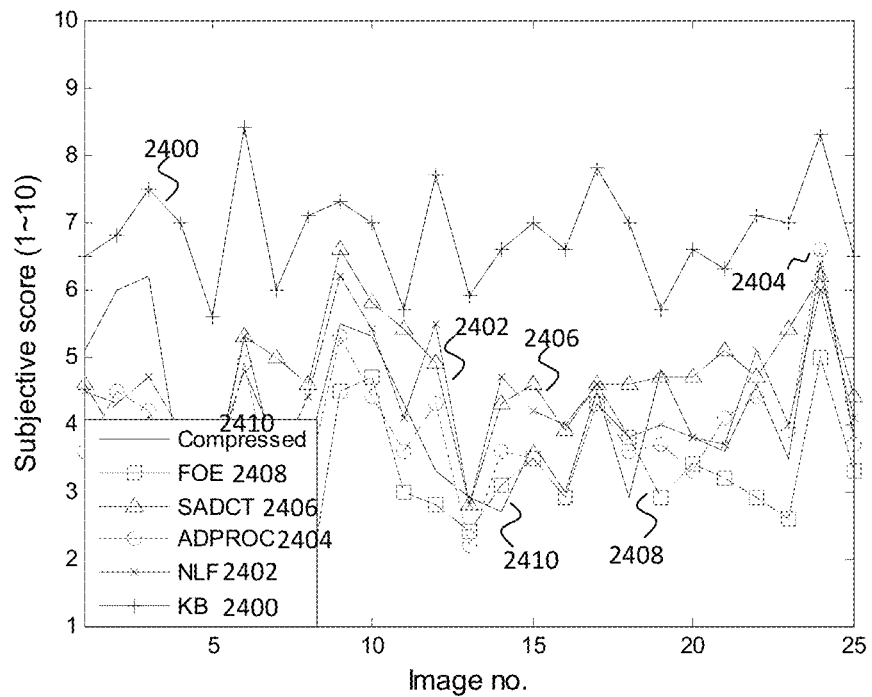

FIG. 17 illustrates examples of some blocks from FIG. 16. Original blocks 1700 in the first row corresponded to the compressed blocks 1702 in the second row. The high compression ratio caused great information loss. In FIG. 17, the third and fourth rows show the resultant blocks from the Markov model based algorithm 1704 and the one-pass algorithm 1706, respectively. For the one-pass algorithm 1706, the hybrid neighbourhood was sufficient to recover the lost information.

An Indexing Mechanism to Speed Up the Algorithms

To make inference based on prior knowledge, a large training set was required and to certain extent, essential. In various example, a training set contained more than 5 million block-pairs. It may be considerably time consuming to search the entire dataset for each testing block.

To speed up the searching, an indexing mechanism was proposed using a multi-dimensional structure to store the information of each original block in the dataset. The number of dimensions corresponded to the length of index vectors. Each entry represented one index vector and stored the information of the corresponding original blocks. This included their positions in the source images and their hybrid neighbourhoods. For a testing block, its index vector immediately led to the corresponding entry in the structure. This mechanism was faster than matching it with all the blocks in the dataset.

This indexing mechanism cannot be used directly in the Y component, because its quantization steps were much smaller than those in U and V components. As a result, the number of different index vectors was too large to be stored in a multi-dimensional structure due to memory constraints. The Y components of the original images were preprocessed by normalizing the intensity values of these Y components to zero mean and unit variance. Then, their index vectors whose varying range decreased significantly were recalculated. This normalization step clustered the index vectors in the Y components into a limited number of groups allowing storage in a multi-dimensional structure. In each entry of the subsequent structure, the un-normalized index vectors were added as extra or additional information to distinguish individual blocks. This indexing mechanism made it possible to handle such a large dataset quickly and efficiently.

Examples of Removing Blocking Artifacts in Skin Images

To evaluate the KB approach, extensive experiments were performed and comparison were made with four other common deblocking methods. The other methods were Sun et al.'s maximum a posteriori method based on a Field of Experts prior (FOE) which achieves higher PSNR gain (D. Sun and W. Chan, "Postprocessing of low bit-rate block DCT coded images based on a fields of experts prior", *IEEE TIP*, vol. 16. no. 11, pp. 2743-2751, 2007), Foi et al.'s Pointwise Shape-adaptive DCT method (SADCT) which was one of the more recent deblocking techniques (A. Foi, V. Katkovnik, and K. Egiazarian, "Pointwise shape-adaptive DCT for high-quality denoising and deblocking of grayscale and colour images", *IEEE TIP*, vol. 16, no. 5, pp. 1395-1411, 2007), Luo et al.'s adaptive processing method (ADPROC) which was efficient at reducing blocking artifacts in smooth regions (Y. Luo and R. K. Ward, "Removing the blocking artifacts of block-based DCT compressed images", *IEEE TIP*, vol. 12, no. 7, pp. 838-842, 2003), and Chou et al.'s nonlinear filtering method (NLF) which was fast and robust for different images and quantization strategies (J. Chou, M. Crouse, and K. Ramchandran, "A simple algorithm for removing blocking artifacts in block-transform coded images". in *Proceedings of the IEEE ICIP*, vol. 1, pp. 377-380, 1998).

These methods and the KB approach were analyzed using the two testing sets. The first testing set with 500 images was compressed with the JPEG quality factor of 50, and the average compression ratio was 72.55. The second testing set with 262 images was compressed with the JPEG quality factor of 25, and the average compression ratio was 126.93. As a result of this high compression ratio in the second set, most skin features were destroyed.

FIGS. 18 to 23 show the comparison of (a) the original images, (b) the compressed images, (c) the images from FOE method, (d) the images from SADCT method, (e) the images from ADPROC method, and (f) the images from NLF method. Additionally, the images from the KB approach are shown in FIGS. 18(g) to 23(g), respectively.

These six sets of skin images were shown for visual comparison. FIGS. 18-20 show respectively the Y, U and V components, and FIGS. 21-23 show the digital photographic images (in colour). The circles 2100, 2200, 2300 in FIGS. 21(a), 22(a) and 23(a), respectively, denote skin marks identified by dermatology experts in the uncompressed images. The compression ratios of FIGS. 18 to 23 were respectively 76.12, 69.50, 78.13, 115.32, 126.97, and 121.16. These figures showed that the FOE and SADCT methods had strong smoothing effect, which occasionally resulted in unrecognizable or absent skin marks; while the ADPROC and NLF methods had less smoothing effect, but these methods did not change the compressed images significantly. In comparison, the KB approach removed the blocking artifacts and successfully recovered lost skin information, including the pigmented skin marks as shown in FIGS. 21(g) to 23(g), respectively (approximately around the corresponding area marked by the respective circle 2100, 2200, 2300 of FIGS. 21(a) to 23(a)).

To quantify these visual comparisons, either image quality indexes were used or a subjective evaluation was carried out. Traditional point-wise comparison measuring for example mean square error (MSE) or peak signal-to-noise ratio (PSNR) may not be well-matched to perceived visual quality (Z. Wang and A. C. Bovik, "Mean squared error: Love it or leave it? A new look at signal fidelity measures", *IEEE Signal Processing Magazine*, vol. 26, no. 1, pp. 98-117, 2009). Other image quality indexes, for example, SSIM (Z. Wang, A. C. Bovik, H. R. Sheikh and E. P. Simoncelli, "Image quality assessment: from error visibility to structural similarity", *IEEE TIP*, vol. 13, no. 4, pp. 600-612, 2004) attempted to mimic the extremely complicated human vision system (HSV). It was very difficult, if not impossible, to perfectly model HSV.

To avoid modeling defects, a subjective evaluation was carried out on the resultant images. Twenty-three observers participated in this study. Three of the observers had dermatological knowledge (one was a board-certified dermatologist and the other two were medical students studying dermatology); while twelve of the observers were familiar with image processing; and the rest of the observers had computer science background. The spread of observers provided objectivity on the study. For example, as law enforcement agents, including the U.S. Department of Justice, recruit board-certified dermatologists to recognize skin marks in legal cases, having a board-certified dermatologist included as an observer may provide expertised findings which may allow for the evaluation to be gauged. All the testing images were prepared by one person. There were no so-called skin mark examiners, for example, fingerprint examiners.

The experiment was carried out in Y, U, V components and digital photographic images, in this case, colour images. In each case, 25 groups of images were presented. For the Y, U and V components, 20 groups were from the first testing set, and 5 groups were from the second testing set, while for the colour images, 5 groups were from the first testing set, and 20 groups were from the second testing set. Totally 100 groups were evaluated. In each group, an original uncompressed image used as a reference (i.e., a comparison bar or a standard) was presented, the corresponding compressed image and the 5 resultant images (4 from the other methods and 1 from the KB approach) to the unbiased observers. The observers to rated the images using a 10-point scale. For the Y, U and V components, the observers were required to rate the resultant images according to their similarity with the respective references. Higher grades (i.e. 10 points) represented higher similarity between the original uncompressed images and the resultant images.

For colour images, skin marks in the respective reference images were highlighted. An example may be as in any one of FIGS. 21 to 23. The observers compared skin marks. As with the Y, U and V components, the same grading scheme was employed. Ten observers participated in the Y, U and V evaluation, and the other ten participated in the colour evaluation. The three dermatological professionals participated in all evaluations. The average scores from the dermatological professionals and from other participants are illustrated in FIGS. 24 and 25, respectively. FIG. 24 shows (a) Y component, (b) U component, (c) V component, and (d) digital photographic image (in colour). Similarly, FIG. 25 shows (a) Y component, (b) U component, (c) V component, (d) digital photographic image (in colour). Both FIGS. 24 and 25 clearly reflect that the KB approach provides the greatest visual quality improvement. These observations clearly pinpointed that the KB approach was effective not only for generic skin images, but also for skin marks. The observations further confirmed the visual comparisons of FIGS. 18-23.

EXAMPLE 2

Vein Uncovering Algorithm

Figure 26A:
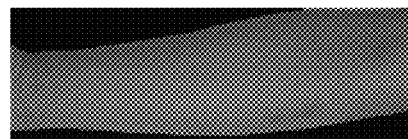
FIGS. 26(a) and 26(c) show digital photographic images (in colour)
Figure 26B:
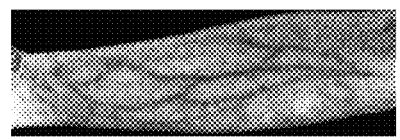
FIG. 26(b) shows the output of FIG. 26(a) obtained from an algorithm in accordance to various embodiments.
Figure 26C:
Figure 26D:
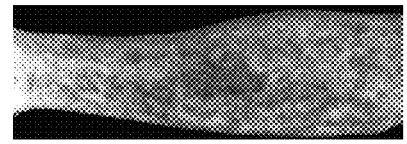
FIG. 26(d) shows the output of FIG. 26(c) obtained from the algorithm in accordance to various embodiments.

Extracting veins from colour images is a very challenging task because the vein patterns are hidden under the skin and nearly invisible. Skin is an intricate layered material whose internal structures vary with individuals, body sites, and time. Additionally, the physical process of image formation may complicate the situation. When the light from an illumination source hits the skin, some light is absorbed while some light is reflected and captured by the sensor in a camera. The characteristics of the illuminant and the camera also play a significant role on the skin color formation in an image. There is no algorithm or software package especially designed for this purpose, except for various embodiments of this invention. FIGS. 26(a) and 26(c) show an example of digital photographic images (in colour). FIGS. 26(b) and 26(d) show the respective output obtained from various embodiments of this invention without parameter range optimization through colour or automatic adjustment of image intensity schemes, as described herein.

Vein Uncovering Algorithm Based on Principles of Optics and Skin Biophysics

Vein uncovering algorithms may also be based on the principles of optics and skin biophysics. In another example, these algorithms inversed the process of the skin colour formation in an image, and derived corresponding biophysical parameters. Although in general, pixels of veins and pixels of generic skin have very similar RGB values, the respective biophysical parameters differ significantly. Therefore, the vein patterns may be uncovered from their spatial distributions. This approach may not be limited to the hand or wrist and can theoretically be applied to any part of the body.

In an example, the algorithm used a Kubelka-Munk (K-M) model (P. Kubelka and F. Munk, "Ein Beitrag zur Optik der Farbanstriche", Z. Tech Phys, vol. 12, pp. 593-601, 1931; and P. Kubelka, "New contribution to the optics of intensely light-scattering materials", JOSA, vol. 38, pp. 448-457, 1948) to reveal hidden vein patterns in digital images or more specifically for easy reference, colour images.

The Kubelka-Munk Model

Figure 27:
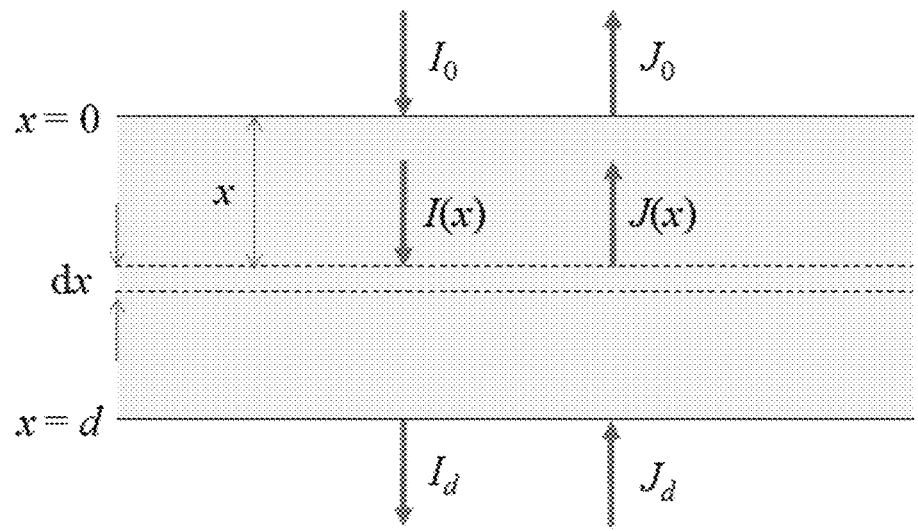
FIG. 27 shows a schematic representation of light transport based on the Kubelka-Munk (K-M) model, in accordance to various embodiments.

The K-M model assumed that the radiation passing through a scattering medium was divided into two diffuse fluxes: one traveled in the forward direction, and the other traveled in the backward direction, as denoted respectively as I and J in FIG. 27.

According to the K-M model, at a distance x from the surface, the changes in flux over an infinitesimal distance dx for I and J are:

$$dI = -(k+s)Idx + sJdx, \qquad (6)$$

$$dJ = (k+s)Jdx - sIdk, \qquad (7)$$

where $k=2\mu_a$ and $s=2\mu_s \cdot \mu_a$ ($\mu_s$) is the absorption (scattering) coefficient of the medium at a particular wavelength, i.e., the fraction of radiation absorbed (scattered) per unit path length.

Using the boundary condition ($J_d$=0), the reflectance and transmittance of the material may be respectively obtained as:

$$R = \frac{(1-\beta^2)(e^{Kd} - e^{-Kd})}{(1+\beta)^2 e^{Kd} - (1-\beta)^2 e^{-Kd}}, \qquad (8)$$

$$T = \frac{4\beta}{(1+\beta)^2 e^{Kd} - (1-\beta)^2 e^{-Kd}}, \qquad (9)$$

where $$K = \sqrt{k(k+2s)}, \qquad (10)$$

$$\beta = \sqrt{k/(k+2s)}. \qquad (11)$$

The reflected light thus depended on three parameters of the material: the absorption coefficient, $\mu_a$, the scattering coefficient, $\mu_s$, and the material thickness, d. In general, the two optical coefficients are wavelength dependent, i.e., $\mu_a(\lambda)$ and $\lambda_s(\lambda)$.

Let the reflectance and transmittance of the $i^{th}$ layer in an n layered material be $R_i$ and $T_i$, respectively. The total reflectance, $R_{12\ldots n}$, and transmittance, $T_{12\ldots n}$ may be computed by the recursive equations:

$$R_{12\ldots n} = R_{12\ldots n-1} + \frac{T_{12\ldots n-1}^2 R_n}{1 - R_{12\ldots n-1} R_n}, \qquad (12)$$

$$T_{12\ldots n} = \frac{T_{12\ldots n-1} T_n}{1 - R_{12\ldots n-1} R_n}. \qquad (13)$$

The K-M theory has been frequently used to model optical properties of different materials. In skin optics, the K-M theory was used to model optical properties of dermal tissue (R. R. Anderson and J. A. Parrish, "The Optics of Human Skin", J. Invest. Dermatol., vol. 77, no. 1, pp. 13-19, 1981; and R. R. Anderson, J. Hu, and J. A. Parrish, "Optical Radiation Transfer in the Human Skin and Applications in In Vivo Remittance Spectroscopy", In Bioengineering and the Skin, ed. R. Marks and P. A. Payne, Chapter 28, pp. 253-265, MTP Press Limited, 1981). This model was extended to compute the absorption and scattering coefficients of the epidermis, taking into account both collimated and diffuse incident irradiance (S. Wan, R. R. Anderson, and J. A. Parrish, "Analytical modeling for the optical properties of the skin with in vitro and in vivo applications", Photochem. Photobiol., vol. 34, no. 4, pp. 493-499, 1981). A model based on the K-M theory which considered both forward and backward scattering, and allowed changes in the refractive index at the air/skin interfaces was also studied (B. Diffey, "A Mathematical Model for Ultraviolet Optics in Skin", Phys. Med. Biol., vol. 28, no. 6, pp. 647-657, 1983). Cases of dominant absorption, dominant scattering, and scattering were further distinguished to be about equal to absorption (M. J. C. Van Gemert, S. L. Jacques, H. J. C. M. Sterenborg, and W. M. Star, "Skin Optics", IEEE Trans. Biomed. Eng., vol. 36, no. 12, pp. 1146-1154, 1989). The K-M model was used to aid the categorization of pigmented skin lesions from colour images (S. Cotton and E. Claridge, "Developing a predictive model of skin colouring", In SPIE Vol. 2708, Medical Imaging 1996, pp. 814-825, 1996). Important factors from the internal structure and composition of pigmented skin lesions were further derived diagnostically (E. Claridge, S. Cotton, P. Hallc, and M. Moncrieffd, "From Colour to Tissue Histology: Physics-Based Interpretation of Images of Pigmented Skin Lesions", Med. Image Anal., no. 7, pp. 489-502, 2003). The human skin was modeled as a two-layered turbid material and the K-M equations was used with six unknown parameters to estimate the reflectance (M. Doi and S. Tominaga, "Spectral Estimation of Human Skin Colour using the Kubelka-Munk Theory", In SPIE/IS&T Electronic Imaging, SPIE, vol. 5008, pp. 221-228, 2003). These parameters were obtained by fitting the estimated reflectance to empirical values using the least squares method. The K-M model was also used to investigate skin colour formation under changing and mixed illumination.

The K-M model was further used to reveal the structure of pigmented skin lesions for diagnosis and predicate optical properties of the skin for laser surgery. However, none of these applications were related to forensics. To date, there are no prior reports of similar research or applications to uncover vein patterns from digital images, for example, colour images for forensic investigation.

The method used by Claridge et al. (E. Claridge, S. Cotton, P. Hallc, and M. Moncrieffd, "From Colour to Tissue Histology: Physics-Based Interpretation of Images of Pigmented Skin Lesions", Med. Image Anal., no. 7, pp. 489-502, 2003) using colour images to diagnose pigmented skin lesions revealed the distributions of melanin, hemoglobin, and the depth of dermis from colour images. In this method, colour images were collected in a controlled environment with white incident light and were used for medical applications. This method was also based on table lookup.

In contrast, various embodiments of the invention provided an algorithm based on a more accurate biophysical structure of the skin. The algorithm in accordance to various embodiments worked under different illumination conditions and used for personal identification. Various embodiments utilized neural networks, which possess good extrapolation ability and may well approximate the nonlinear relationship between skin colour and biophysical parameters.

Another method that may possibly uncover veins was the Independent Component Analysis (ICA)-based method. ICA was used to analyze and synthesize the colour and texture of human skin (N. Tsumura, H. Haneishi, and Y. Miyake, "Independent Component Analysis of Skin Colour Image", JOSA (A), vol. 16, no. 9, pp. 2169-21'76, 1999). An important assumption in this method was the linearity among quantities of pigments. However, the complex structure of the skin very likely violated this assumption (N. Tsumura, H. Haneishi, and Y. Miyake, "Independent Component Analysis of Spectral Absorbance Image in Human Skin", Opt. Rev., vol. 7, no. 6, pp. 479-482, 2000). It was also assumed that spectral absorbance of the pigments did not change spatially. Nevertheless, hemoglobin has two states: oxy-hemoglobin and deoxy-hemoglobin, which have different absorption coefficients. Another important problem with this ICA-based method was that it may not converge for hair on the skin or highly compressed JPEG skin images.

Using the K-M Model to Uncover Vein Patterns in Digital Images

To uncover vein patterns hidden in digital images or more specifically for easy reference, colour images, a computation model was used to reveal the spatial distributions of the volume fraction (%) of the epidermis occupied by melanosomes, the volume fraction (%) of the dermis occupied by blood, and the depth of the dermis. They were respectively denoted as $\theta_n$, $\theta_p$, and $d^{der}$. Intuitively, vein patterns may be found in $\theta_p$, as these vein patterns contained higher concentration of blood than other skin components. Veins with a certain size may occupy the spaces of dermis and epidermis and therefore, these veins may also be observed from the spatial distributions of $\theta_n$ and $d^{der}$.

Mathematically, a function g was established such that given a colour image and other information, the function g mapped input variables to $\theta_m$, $\theta_p$ and $d^{der}$. More precisely, the mapping was $$[\theta_m, \theta_p, d^{der}] = g(R, G, B, E), \quad (14)$$

where R, G, and B represent the three colour components in a given image, and E represents other information. In this model, E included prior knowledge from cameras, and illuminants.

To obtain the function g, the formation of skin colour in an image was firstly modeled as given by:

$$[R, G, B] = f(I(\lambda), \theta_m, \theta_p, d^{der}, S_R(\lambda), S_G(\lambda), S_B(\lambda)), \quad (15)$$

where $S_R(\lambda)$, $S_G(\lambda)$, and $S_B(\lambda)$ are respectively the R, G, and B spectral response functions of a camera, $I(\lambda)$ is an illuminant, and $\lambda$ represents wavelengths. In legal cases, the spectral response functions may be known through the camera model, which may be found in headers of evidence images.

Three types of light sources are commonly encountered in a real environment: daylight, incandescent lamps, and fluorescent lamps. They correspond respectively to illuminant D65, A and F, which are standard illuminants established by The International Commission on Illumination.

Based on environments exposed in evidence images, the illuminant may be determined. Thus, it was not unrealistic to assume that $S_R(\lambda)$, $S_G(\lambda)$, $S_B(\lambda)$ and $I(\lambda)$ were known.

Once the function $f$ was established, R, G and B values of the skin in an image may be obtained, when $I(\lambda)$, $\theta_m$, $\theta_p$, $d^{der}$, $S_R(\lambda)$, $S_G(\lambda)$, and $S_B(\lambda)$ were given. The mapping from [$I(\lambda)$, $\theta_m$, $\theta_p$, $d^{der}$, $S_R(\lambda)$, $S_G(\lambda)$, $S_B(\lambda)$] to [R, G, B] was established. If this mapping was one-to-one, $$[I(\lambda),\theta_m,\theta_p,d^{der},S_R(\lambda),S_G(\lambda),S_B(\lambda)]=f^{-1}(R,G,B), \quad (16)$$

may be obtained. Because $S_R(\lambda)$, $S_G(\lambda)$, $S_B(\lambda)$ and $I(\lambda)$ were known, Eq. 16 may be simplified as $[\theta_m, \theta_p, d^{der}]=f^{-1}(R, G, B)$. However, $f$ was not a one-to-one function, and therefore, $f^{-1}$ did not exist.

A function $g \approx f^{-1}$ was constructed as given by:

$$[\theta_m,\theta_p,d^{der}]=g(R,G,B), \quad (17)$$

from a neural network.

Figure 28:
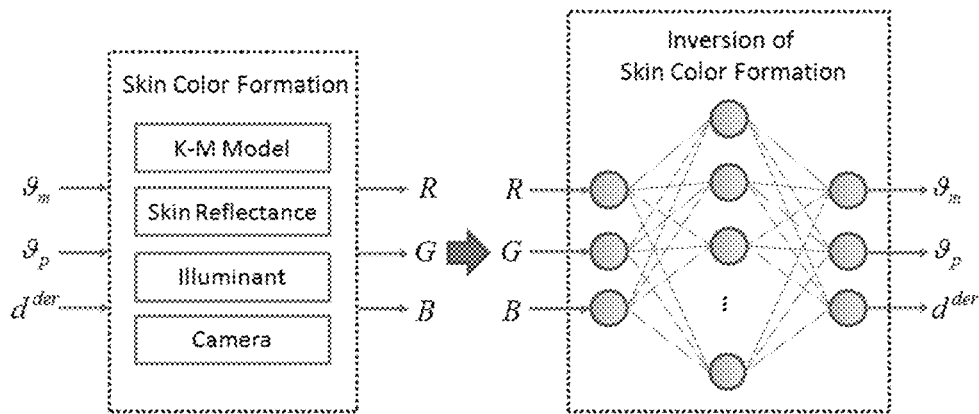
FIG. 28 shows a schematic diagram of an algorithm to uncover vein patterns wherein the left block represents the skin color formation model and the right block represents the inversion of the skin color formation, in accordance to various embodiments.

The information from $S_R(\lambda)$, $S_G(\lambda)$, $S_B(\lambda)$ and $I(\lambda)$ was embedded in Eq. 17, although this information was not shown explicitly. FIG. 28 shows a schematic diagram of the algorithm in accordance to various embodiments of the invention to uncover vein patterns. The left block represented the skin colour formation model and the right block represented the inversion of the skin colour formation to obtain $[\theta_m, \theta_p, d^{der}]$ from [R, G, B].

The Skin Colour Formation

The K-M theory and the optical properties of the skin to model skin colour formation were used in an image. According to the K-M model, the reflectance of a material was mainly determined by the absorption and scattering characteristics of each layer. The human skin is composed of three layers: the stratum corneum, the epidermis and the dermis.

Figure 29:
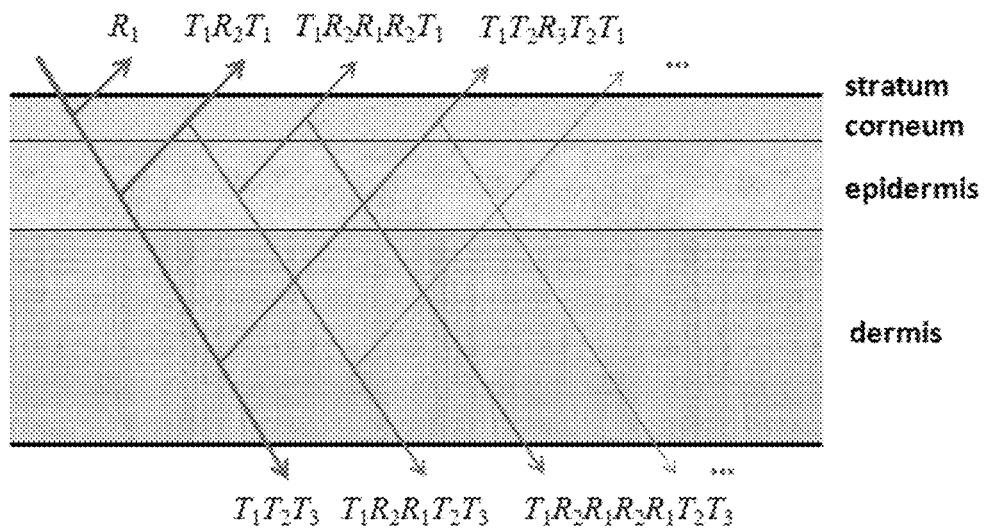
FIG. 29 shows a schematic representation of a process of light transport in a human skin based on the K-M model, in accordance to various embodiments.

FIG. 29 illustrates a schematic view of the process of light transport in human skin. A fraction of the incident light was reflected by the stratum corneum and the rest penetrates into the deeper layers. In the epidermal and dermal layers, the light was scattered multiple times and absorbed by melanin, hemoglobin, β-carotene, and bilirubin.

According to the K-M model, the reflectance $R_{123}(\lambda)$ and transmittance $T_{123}(\lambda)$ of the whole skin may be obtained from $$R_{123}(\lambda)=R_{12}(\lambda)+T_{12}(\lambda)^2 R_3(\lambda)/[1-R_{12}(\lambda)R_3(\lambda)], \quad (18)$$

$$T_{123}(\lambda)=T_{12}(\lambda)T_3(\lambda)/[1-R_{12}(\lambda)R_3(\lambda)], \quad (19)$$

where $$R_{12}(\lambda)=R_1(\lambda)+T_1(\lambda)^2 R_2(\lambda)/[1-R_1(\lambda)R_2(\lambda)], \quad (20)$$

$$T_{12}(\lambda)=T_1(\lambda)T_2(\lambda)/[1-R_1(\lambda)R_2(\lambda)]. \quad (21)$$

The variables $R_i(\lambda)$ and $T_i(\lambda)$ (i=1,2,3) in the equations were respectively the reflectance and transmittance of the i$^{th}$ layer of the skin. The 1$^{st}$, 2$^{nd}$ and 3$^{rd}$ layers were respectively the stratum corneum, the epidermis and the dermis. According to Eqs. 8-11, $R_i(\lambda)$ and $T_i(\lambda)$ were determined by the absorption coefficient, $\mu_{ia}$, the scattering coefficient, $\mu_{is}$, and the thickness of the corresponding layer.

The Absorption and Scattering Coefficients of the Stratum Corneum

The total absorption coefficient of the stratum corneum may be:

$$\mu_{1a}(\lambda)=\mu_a^{base}(\lambda)+\mu_a^{cs}(\lambda)[\text{cm}^{-1}], \quad (22)$$

where $\mu_a^{base}(\lambda)$ and $\mu_a^{cs}(\lambda)$ were respectively the absorption coefficients of the baseline skin and the β-carotene in the stratum corneum.

The absorption coefficients were calculated as:

$$\mu_a^{base}(\lambda)=0.244+85.3\cdot\exp\{-(\lambda-154)/66.2)\} \text{ [cm}^{-1}], \quad (23)$$

$$\mu_a^{cs}(\lambda)=\epsilon^{car}(\lambda)\cdot c^{cs}/m^{car}[\text{cm}^{-1}], \quad (24)$$

where $\epsilon^{car}(\lambda)$ was the extinction coefficient of β-carotene, $m^{car}$ was its molecular weight, and $c^{cs}$ was its concentration in the stratum corneum.

The scattering of light in the stratum corneum combined the Mie scattering by large cylindrical collagen fibers and the Rayleigh scattering by small-scale structures associated with the collagen fibers and other cellular structures. The total scattering coefficient in the stratum corneum may be obtained by $$\mu_{1s}(\lambda)=2\times10^5\times\lambda^{-1.5}+2\times10^{12}\times\lambda^{-4}[\text{cm}^{-1}], \quad (25)$$

where the first term was for the Mie scattering and the second was for the Rayleigh scattering.

The Absorption and Scattering Coefficients of the Epidermis

The total absorption coefficient of the epidermis may be:

$$\mu_{2a}(\lambda)=(\beta_m\mu_a^{em}(\lambda)+(1-\beta_m)\mu_a^{pm}(\lambda))\theta_m+(\mu_a^{base}(\lambda)+\mu_a^{ce}(\lambda))(1-\theta_m)[\text{cm}^{-1}], \quad (26)$$

where $\mu_a^{em}(\lambda)$ and $\mu_a^{pm}(\lambda)$ were the absorption coefficients of eumelanin and pheomelanin, respectively.

$\beta_m$ controlled the ratio of the amount of eumelanin and pheomelanin. $\theta_m$ was the volume fraction (%) of the epidermis occupied by melanosomes, organelles containing melanin. For lightly pigmented skin, $\theta_m$ was about 1.3-6.3%; for moderately pigmented skin, $\theta_m$ was about 7-16%; and for darkly pigmented skin, $\theta_m$ was about 17-43%. $\mu_a^{ce}(\lambda)$ was the absorption coefficient of β-carotene in the epidermis. $\mu_a^{em}(\lambda)$, $\mu_a^{pm}(\lambda)$ and $\mu_a^{ce}(\lambda)$ may be calculated as:

$$\mu_a^{em}(\lambda)=\epsilon^{em}(\lambda)\cdot c^{em}/m^{em}[\text{cm}^{-1}], \quad (27)$$

$$\mu_a^{pm}(\lambda)=\epsilon^{pm}(\lambda)\cdot c^{pm}/m^{pm}[\text{cm}^{-1}], \quad (28)$$

$$\mu_a^{ce}(\lambda)=\epsilon^{car}(\lambda)\cdot c^{ce}/m^{car}[\text{cm}^{-1}], \quad (29)$$

where $\epsilon^{em}(\lambda)$ and $\epsilon^{pm}(\lambda)$ were the extinction coefficients of eumelanin and pheomelanin, respectively, $m^{em}$ and $m^{pm}$ were the respective molecular weights, $c^{em}$ and $c^{pm}$ were the respective concentrations in melanosomes, and $c^{ce}$ was the concentration of β-carotene in the epidermis.

The total scattering coefficient in epidermis was the same as the total scattering coefficient in the stratum corneum i.e., $\mu_{2s}(\lambda)=\mu_{1s}(\lambda)$.

The Absorption and Scattering Coefficients of the Dermis

The total absorption coefficient of the dermis may be:

$$\mu_{3a}(\lambda)=(\gamma\mu_a^{ohb}(\lambda)+(1-\gamma)\mu_a^{dhb}(\lambda)+\mu_a^{bil}(\lambda)+\mu_a^{cd}(\lambda))\theta_p+\mu_a^{base}(\lambda)(1-\theta_p)[\text{cm}^{-1}], \quad (30)$$

where $\mu_a^{ohb}(\lambda)$ and $\mu_a^{dnb}(\lambda)$ were the absorption coefficients of oxy-hemoglobin and deoxy-hemoglobin, respectively, γ controlled the ratio of the amount of oxy-hemoglobin and deoxy-hemoglobin, $\mu_a^{bil}(\lambda)$ and $\mu_a^{cd}(\lambda)$ were the absorption coefficients of bilirubin and the β-carotene in the dermis, respectively, and $\theta_p$ is the volume fraction (%) of the dermis occupied by the blood.

$\mu_a^{ohb}(\lambda)$, $\mu_a^{dhb}(\lambda)$, $\mu_a^{bil}(\lambda)$ and $\mu_a^{cd}(\lambda)$ may be calculated as:

$$\mu_a^{ohb}(\lambda)=\epsilon^{ohb}(\lambda)\cdot c^{hb}/m^{hb}[\text{cm}^{-1}], \quad (31)$$

$$\mu_a^{dhb}(\lambda)=\epsilon^{dhb}(\lambda)\cdot c^{hb}/m^{hb}[\text{cm}^{-1}], \quad (32)$$

$$\mu_a^{bil}(\lambda)=\epsilon^{bil}(\lambda)\cdot c^{bil}/m^{bil}[\text{cm}^{-1}], \quad (33)$$

$$\mu_a^{cd}(\lambda)=\epsilon^{car}(\lambda)\cdot c^{cd}/m^{car}[\text{cm}^{-1}], \quad (34)$$

where $\epsilon^{ohb}(\lambda)$, $\epsilon^{dhb}(\lambda)$ and $\epsilon^{bil}(\lambda)$ were the extinction coefficients of oxy-hemoglobin, deoxy-hemoglobin and bilirubin, respectively, $m^{hb}$ and $m^{bil}$ were the molecular weights of hemoglobin and bilirubin, respectively, and $c^{hb}$, $c^{bil}$ and $c^{cd}$ were the concentrations of hemoglobin, bilirubin and β-carotene in the blood, respectively.

The deeper regions of the skin were generally less scattering than the upper regions because there were lower concentrations of scatterers. The scattering coefficient of the dermis was about 50% of that of the epidermis, i.e., $\mu_{3s}(\lambda)=0.5\mu_{2s}(\lambda)$.

Using the absorption coefficients, $\mu_{1a}$, $\mu_{2a}$ and $\mu_{3a}$, the scattering coefficients, $\mu_{1s}$, $\mu_{2s}$ and $\mu_{3s}$, Eqs. 8-11 and Eqs. 18-21, the reflectance of the skin, $R_{123}(\lambda)$ may be obtained.

A Model of Sensors in Digital Cameras

By supplying the incident light and the skin reflectance, the colour captured by a camera was then derived by convolving the reflected light with spectral response functions of a camera, i.e., $$R=\int_0^\infty I(\lambda)R_{123}(\lambda)S_R(\lambda)d\lambda, \quad (35)$$

$$G=\int_0^\infty I(\lambda)R_{123}(\lambda)S_G(\lambda)d\lambda, \quad (36)$$

$$B=\int_0^\infty I(\lambda)R_{123}(\lambda)S_B(\lambda)d\lambda, \quad (37)$$

where $I(\lambda)$ was the illuminant, $R_{123}(\lambda)$ was the reflectance of the skin, $S_R(\lambda)$, $S_G(\lambda)$, $S_B(\lambda)$ were respectively the R, G and B spectral response functions of the camera. As earlier described, given a camera model, these spectral response functions may be obtained from producers or manufacturers. By selecting different illuminants, camera models, and skin parameters, different imaging configurations and types of skin may be simulated.

An Inversion of the Skin Colour Formation

Using Eqs. 18-37 as a forward model, the constant skin parameters determined by a series of biophysical studies, and other biological data to limit the ranges of $\theta_m$, $\theta_p$ and $d^{der}$, data pairs (R, G, B) and ($\theta_m$, $\theta_p$, $d^{der}$) may be obtained. $\theta_m$, $\theta_p$ and $d^{der}$ may be exhaustively changed to obtain corresponding colour values. Then, the colour values were used as inputs and the parameters as target outputs to train a three-layered feed-forward neural network. The transfer functions in the hidden and output layers were respectively the classical tan-sigmoid and linear functions. In an example, 5 neurons were placed in the hidden layer. The network was trained with the Levenberg-Marquardt back-propagation algorithm (S. Haykin, Neural Networks: A Comprehensive Foundation. New York: Macmillan Publishing, 1994) and converged in five iterations.

The trained neural network depended on the spectral response functions of the camera and the illuminant. Thus, different cameras or different illuminants may have different neural networks. The trained neural network was in fact the function g in Eq. 17.

To visualize vein patterns in a digital image or a test image, its RGB values were input to the trained neural network, and the outputs were collected to form three distribution maps: the spatial distributions of melanin and hemoglobin, and the variation of the depth of dermis. As hemoglobin was mainly found in veins which were located in the dermis, the pixels of veins and pixels of generic skin had different parameter values. The melanin and depth of dermis also provided information of vein patterns. Generally, as veins occupy some space, generic skin has a thicker dermis layer than skin regions with veins. For the same reason, the distribution of melanin was also influenced by veins. Consequently, these veins may also be uncovered from these distribution maps.

Two schemes namely parameter range optimization and image intensity adjustment were presented to further enhance the algorithm given above.

Parameter Range Optimization through Colour

A three-layered feed-forward neural network was used to approximate the inversion of skin color formation. When simulating the forward skin optical model to prepare training data, the parameter ranges were not taken directly from literature. This is because those parameter ranges were obtained in ideal medical settings from a particular race (in particular, Caucasian) and body site (in particular, hand). Therefore, the data from literature may not be applicable to forward skin optical model.

In this scheme, a typical skin image from a database was selected and its average RGB value was used as a target to optimize the parameters in the model of skin color formation. After obtaining the optimal values, the parameter ranges were set from half to twice of the optimal values.

Figure 30:
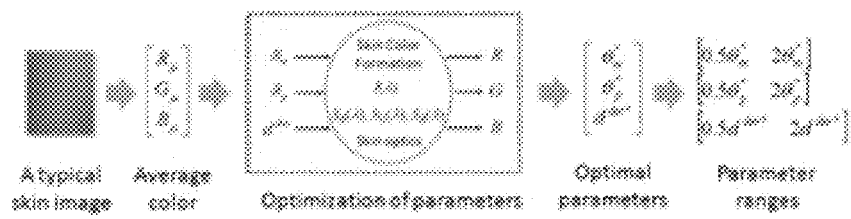
FIG. 30 shows a schematic representation of a process of parameter range optimization, in accordance to various embodiments.

FIG. 30 illustrates the process of parameter range optimization. Then the model of skin color formation was simulated and the corresponding RGB values were obtained.

Figure 31:
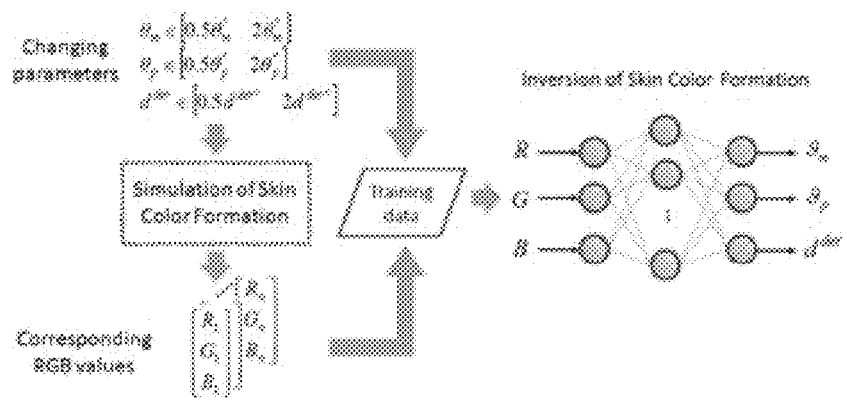
FIG. 31 shows a schematic representation of a process of training data preparation for the neural network in accordance to various embodiments.
Figure 32A:
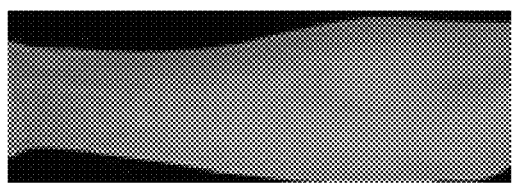
FIG. 32 shows images for an exemplary comparison of vein uncovering algorithms illustrating (a) an image of the inner right forearm of a male (color image); (b) its NIR image; (c) the distribution maps of $d^{der}$ obtained from the uncovering algorithm without the two schemes as described herein, and (d) the uncovering algorithm under these two schemes (intensity adjustment ratio a*=1.1), in accordance to various embodiments.
Figure 32B:
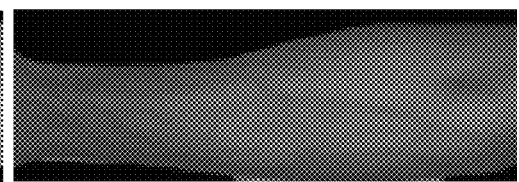
Figure 32C:
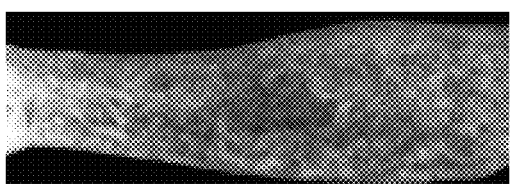
Figure 32D:
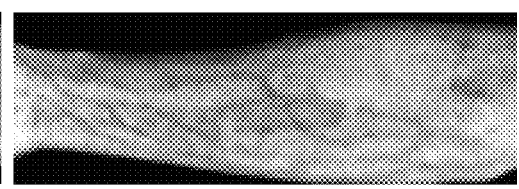
Figure 33A:
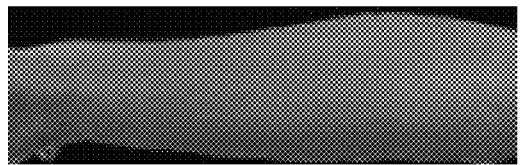
FIG. 33 shows images for another exemplary comparison of vein uncovering algorithms illustrating (a) an image of the inner right forearm of a male (color image); (b) its NIR image; (c) the distribution maps of $d^{der}$ obtained from the uncovering algorithm without the two schemes as described herein, and (d) the uncovering algorithm under these two schemes (intensity adjustment ratio a*=0.8), in accordance to various embodiments.
Figure 33B:
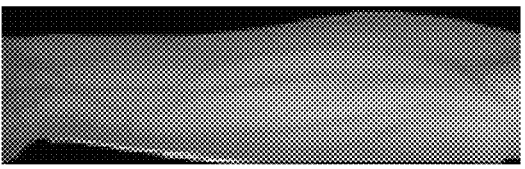
Figure 33C:
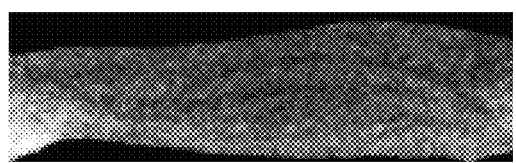
Figure 33D:
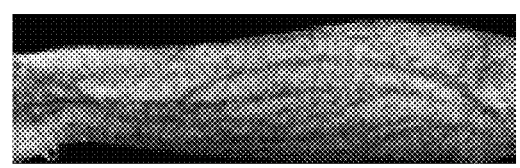

FIG. 31 illustrates the process of training data preparation for the neural network. The trained neural network approximated the inversion of skin color formation. It is in fact the function g in Eq. 17, constructed from a three-layered feed-forward neural network. To visualize vein patterns in a test image, its RGB values were inputs to the trained neural network, and the outputs were collected to form the distribution maps of $\theta_m$, $\theta_p$, and $d^{der}$. The three parameters for each pixel in an image were not optimized because the optimization was very time-consuming. Using MATLAB on a PC embedded with an Intel® Core™2 Quad processor (3.0 GHz) to optimize an image with size of 200×300 pixels, it may take about 50 hours. However, in contrast, using neural network mapping, it may take only about one second.

Automatic Adjustment of Image Intensity

Illuminant has great influence on skin color in images and therefore, the performance of the RGB-based uncovering algorithm may deteriorated if $I(\lambda)$ was not estimated accurately. Although several standard illuminants (e.g. D65) may be used to estimate $I(\lambda)$, the power may vary significantly. To avoid manual estimation of the power, a scheme was used to automatically adjust image intensity to improve the robustness of the uncovering algorithm. Although all of the three parameter maps ($\theta_m$, $\theta_p$, $d^{der}$) showed vein patterns, the distribution map of $d^{der}$ was the clearest. Therefore, it was used in intensity adjustment and later automatic matching. An intensity adjustment ratio a was introduced in the mapping i.e., $$d^{der}=g_{der}(C/a) \quad (38)$$

where C is a color skin image and $g_{der}$ represents the neural network function mapping RGB values to $d^{der}$.

The averaged local variance of the $d^{der}$ map was used as an objective function to determine the optimal adjustment ratio a*:

$$a^* = \underset{a \in A}{\mathrm{argmax}}\left\{\frac{1}{N}\sum_{i=1}^{N}\underset{(x,y)\in M_{bi}}{\mathrm{var}}[d_{bi}^{der}(x,y)]\right\} \quad (39)$$

where A is the set of different intensity adjustment ratios, $d_{bi}^{der}$ is the $i^{th}$ 5×5 block in $d^{der}$, N is the total number of blocks, (x, y) is the position of a pixel, and $M_{bi}$ is the set of skin pixels in $d_{bi}^{der}$. It was noted that only skin pixels were considered in the calculation of local variance.

FIGS. 32 and 33 respectively show outputs from the same uncovering algorithm with and without the two schemes, automatic adjustment of image intensity and parameter range optimization through colour.

FIG. 32 shows an exemplary comparison of vein uncovering algorithms illustrating (a) an image of the inner right forearm of a male (color image); (b) its NIR image; (c) the distribution map of $d^{der}$ obtained from the uncovering algorithm without the two schemes and (d) the uncovering algorithm under these two schemes (intensity adjustment ratio a*=1.1).

FIG. 33 shows another exemplary comparison of vein uncovering algorithms illustrating (a) an image of the inner right forearm of a male (color image); (b) its NIR image; (c) the distribution map of $d^{der}$ obtained from the uncovering algorithm without the two schemes and (d) the uncovering algorithm under these two schemes (intensity adjustment ratio a*=0.8).

Visual comparison with NIR images showed that the outputs from the uncovering algorithm under these two schemes contained more and clearer vein patterns.

Examples of Evaluating the Vein Uncovering Algorithm

To evaluate the vein uncovering algorithm, corresponding digital photographic images (in color) and near infrared (NIR) skin images were collected. The NIR images were considered as the ground truth (or reference) for comparison. The outcomes using the vein uncovering algorithm in accordance with various embodiments of the invention were compared against with those obtained from Tsumura et al.'s method (N. Tsumura, H. Haneishi, and Y. Miyake, "Independent Component Analysis of Skin Color Image", JOSA(A), vol. 16, no. 9, pp. 2169-2176, 1999) and Claridge et al.'s method (E. Claridge, S. Cotton, P. Hallc, and M. Moncrieffd, "From Colour to Tissue Histology: Physics-Based Interpretation of Images of Pigmented Skin Lesions", Med. Image Anal., no. 7, pp. 489-502, 2003). Nikon D60 and the illuminant of D65 were employed in these evaluations.

FIGS. 34-37 show examples of (a) original digital photographic skin images (in colour), (b) the corresponding NIR images, (c) the first components obtained from Tsumura et al.'s method, (d) the second components obtained from Tsumura et al.'s method, (e) the distribution maps of melanin obtained from Claridge et al.'s method, (f) the distribution maps of hemoglobin obtained from Claridge et al.'s method, (g) the distribution maps of depth of papillary dermis obtained from Claridge et al.'s method, (h) the distribution maps of melanin obtained from the preliminary vein uncovering algorithm in accordance with various embodiments of the invention, (i) the distribution maps of hemoglobin obtained from the preliminary vein uncovering algorithm in accordance with various embodiments of the invention and (j) the distribution maps of depth of dermis obtained from the preliminary vein uncovering algorithm in accordance with various embodiments of the invention. The term preliminary vein uncovering algorithm refers to the uncovering algorithm without implementing the two schemes, automatic adjustment of image intensity and parameter range optimization through colour.

Figure 34A:
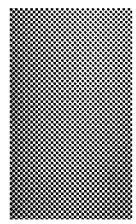
FIG. 34 shows (a) original digital photographic skin image (in colour) of the front side of the left leg of a female subject, (b) the corresponding NIR images, (c) the first components obtained from Tsumura et al.'s method, (d) the second components obtained from Tsumura et al.'s method, (e) the distribution maps of melanin obtained from Claridge et al.'s method, (f) the distribution maps of hemoglobin obtained from Claridge et al.'s method, (g) the distribution maps of depth of papillary dermis obtained from Claridge et al.'s method, (h) the distribution maps of melanin obtained from the vein uncovering algorithm in accordance with various embodiments of the invention, (i) the distribution maps of hemoglobin obtained from the vein uncovering algorithm in accordance with various embodiments of the invention and (j) the distribution maps of depth of dermis obtained from the vein uncovering algorithm in accordance with various embodiments of the invention.
Figure 34B:
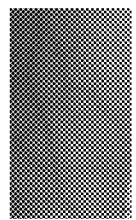
Figure 34C:
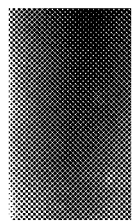
Figure 34D:
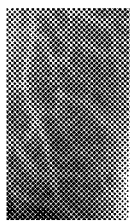
Figure 34E:
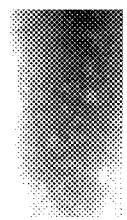
Figure 34F:
Figure 34G:
Figure 34H:
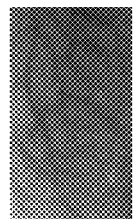
Figure 34I:
Figure 34J:

FIG. 34(a) shows an image of the front side of the left leg of a female subject. The skin in this image had low concentration of melanin and fat, and therefore, Tsumura et al.'s method was able to show the veins. Claridge et al.'s method provided almost nothing about veins. The preliminary vein uncovering algorithm in accordance with various embodiments of the invention showed clear vein patterns as in the case of Tsumura et al.'s method. The clarity of the vein patterns in the right part of the image is comparable or even clear (or vein being more prominently shown) than that in the NIR image.

Figure 36A:
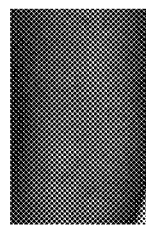
FIG. 36 shows (a) original digital photographic skin image (in colour) of the back side of the left leg of a male subject, (b) the corresponding NIR images, (c) the first components obtained from Tsumura et al.'s method, (d) the second components obtained from Tsumura et al.'s method, (e) the distribution maps of melanin obtained from Claridge et al.'s method, (f) the distribution maps of hemoglobin obtained from Claridge et al.'s method, (g) the distribution maps of depth of papillary dermis obtained from Claridge et al.'s method, (h) the distribution maps of melanin obtained from the vein uncovering algorithm in accordance with various embodiments of the invention, (i) the distribution maps of hemoglobin obtained from the vein uncovering algorithm in accordance with various embodiments of the invention and (j) the distribution maps of depth of dermis obtained from the vein uncovering algorithm in accordance with various embodiments of the invention.
Figure 36B:
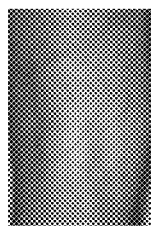
Figure 36C:
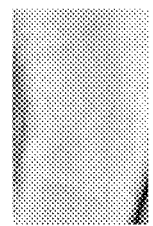
Figure 36D:
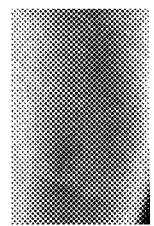
Figures 36E, 36F:
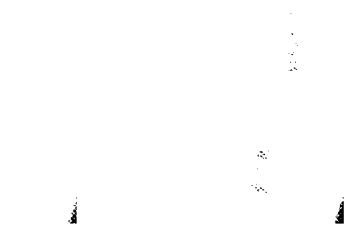
Figure 36G:
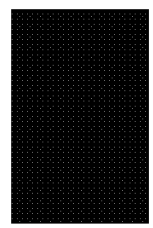
Figure 36H:
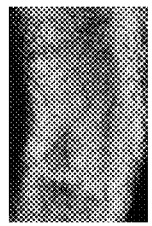
Figure 36I:
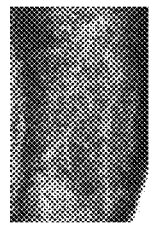
Figure 36J:
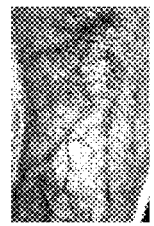
Figure 37A:
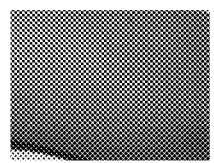
FIG. 37 shows (a) original digital photographic skin image (in colour) of the back side of the right upper arm of a male subject, (b) the corresponding NIR images, (c) the first components obtained from Tsumura et al.'s method, (d) the second components obtained from Tsumura et al.'s method, (e) the distribution maps of melanin obtained from Claridge et al.'s method, (f) the distribution maps of hemoglobin obtained from Claridge et al.'s method, (g) the distribution maps of depth of papillary dermis obtained from Claridge et al.'s method, (h) the distribution maps of melanin obtained from the vein uncovering algorithm in accordance with various embodiments of the invention, (i) the distribution maps of hemoglobin obtained from the vein uncovering algorithm in accordance with various embodiments of the invention and (j) the distribution maps of depth of dermis obtained from the vein uncovering algorithm in accordance with various embodiments of the invention.
Figure 37B:
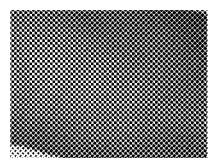
Figure 37C:
Figure 37D:
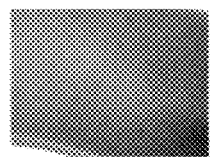
Figure 37E:
Figure 37F:
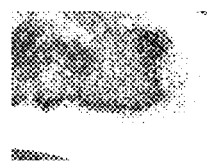
Figure 37G:
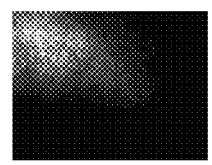
Figure 37H:
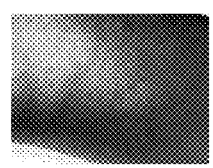
Figure 37I:
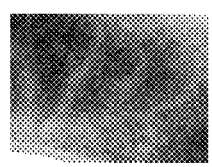
Figure 37J:
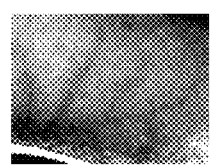

FIG. 35(a) shows an image of the front side of the left leg of a male subject. FIG. 36(a) shows an image of the back side of the left leg of a male subject. FIG. 37(a) shows an image of the back side of the right upper arm of a male subject. The skin in these images contained higher concentration of melanin or fat. It was nearly impossible to observe the vein patterns from the digital photographic images (in colour). For these images, both Tsumura et al.'s method and Claridge et al.'s method provided almost nothing about the veins. In contrast, the preliminary vein uncovering algorithm in accordance with various embodiments of the invention uncovered clear vein patterns. These encouraging evaluation outcomes clearly demonstrated that body vein patterns may be uncovered from digital photographic skin images (in colour) for forensic investigations. Claridge et al.'s method and Tsumura et al.'s method were not designed forensic analysis, but rather, for medical and computer graphic applications.

To verify the reliability of the preliminary vein uncovering algorithm in accordance with various embodiments of the invention, five "examiners" performed the matching of the NIR images with the uncovered vein distribution maps generated. Manual matching is generally, at least at present, a very accurate and reliable method. Thus, for personal identification in legal cases, final fingerprint comparisons are still based on expert latent print examiners.

The testing database contained image pairs (NIR and digital photographic images (in colour)) from 4 body parts of 150 persons: inner forearm (IF), outer forearm (OF), front thigh (FT), and outer thigh (OT). The images were taken in two settings, with an interval of at least one week. Vein patterns were uncovered from the color images using the preliminary vein uncovering algorithm in accordance with various embodiments of the invention. The evaluations by the 5 examiners were performed in two testing sessions. In each session, 16 groups of images (4 groups from each body part) were presented to each of the "examiners". Each group contained 3 vein distribution maps from a digital photographic skin image (in colour) and 10 NIR images—one was from the same individual that the digital photographic image was from and the other nine were selected from the same body part of the other 149 persons. The examiners were asked to match the vein distribution maps to one of the ten NIR images. If they were not confident in their match, they were allowed to answer as such. In the first testing session, the original color image and the corresponding NIR image were taken on the same photography day, while in the second session, they were taken on different days. Thus, in the second testing session, there were more illumination and perspective variations between the NIR and the digital photographic image (in colour).

Table 1 shows the matching outcomes, where C represents "correct" and N represents "NO confidence". The percentage of "correct" was calculated by the total number of correct matchings over the total number of attempted matches. The percentage of "NO confidence" was calculated by the total number of unanswered matches over the total number of attempts. In the first session, Examiners 1, 3 and 5 were 100% correct, answering all matches. In the second session, Examiners 2 and 5 were 100% correct; Examiner 2 did not answer in 25% of the trials, while Examiner 5 answered for all of the matches. These findings demonstrated that different examiners have different capability to recognize the veins. Examiner 5 may have performed significantly better than others because he was familiar with fingerprint, palmprint, iris and skin mark matching. Most importantly, these findings indicated that the uncovering vein patterns may be used for personal identification. In application, professional examiners who would be performing these vein pattern matchings for legal cases would have received sufficient training, as is the case for professional fingerprint examiners.

TABLE 1

| | | Session 1 | | | | | Session 2 | | | | |
|---|---|---|---|---|---|---|---|---|---|---|---|
| | | IF | OF | FT | OT | AVG | IF | OF | FT | OT | AVG |
| [1]E1 | [2]C | 100 | 100 | 100 | 100 | 100 | 100 | 75 | 100 | 100 | 93.75 |
| | [3]N | 0 | 0 | 0 | 0 | 0 | 0 | 0 | 0 | 0 | 0 |
| E2 | C | 100 | 75 | 75 | 100 | 87.5 | 100 | 100 | 100 | 100 | 100 |
| | N | 0 | 0 | 0 | 50 | 12.5 | 0 | 25 | 25 | 50 | 25 |
| E3 | C | 100 | 100 | 100 | 100 | 100 | 100 | 75 | 100 | 100 | 93.75 |
| | N | 0 | 0 | 0 | 0 | 0 | 0 | 0 | 0 | 0 | 0 |
| E4 | C | 100 | 100 | 75 | 100 | 93.75 | 100 | 100 | 25 | 100 | 81.25 |
| | N | 0 | 0 | 0 | 0 | 0 | 0 | 0 | 0 | 0 | 0 |
| E5 | C | 100 | 100 | 100 | 100 | 100 | 100 | 100 | 100 | 100 | 100 |
| | N | 0 | 0 | 0 | 0 | 0 | 0 | 0 | 0 | 0 | 0 |
| [4]AVG | C | 100 | 95 | 90 | 100 | 96.25 | 100 | 90 | 85 | 100 | 93.75 |
| | N | 0 | 0 | 0 | 10 | 2.5 | 0 | 5 | 5 | 10 | 5 |

[1]E stands for Examiner;
[2]C represents "correct matching",
[3]N represents "NO-confidence", and
[4]AVG means average.

Further, in another evaluation example, the outputs of the vein uncovering algorithm according to various embodiments were compared the preliminary uncovering algorithm. All the experiments were performed on a personal computer (PC) with the same configuration. The term, the vein uncovering algorithm and preliminary uncovering algorithm refer respectively to the vein uncovering algorithm with and without the two schemes reported in Example 2.

The database contained 300 color images and 300 NIR images from 150 different forearms. The images were collected on two separate occasions, at an interval of about two weeks. In total, each subject in each session provided one color image and one NIR image. The vein uncovering algorithm according to various embodiments and the preliminary uncovering method according to various embodiments were applied to the color images. Vein patterns were extracted from distribution maps of $d^{der}$. Cumulative match curves generated from the matching outputs were used as a performance indicator.

To verify the proposed uncovering algorithm, two sets of studies were performed. One hundred fifty vein patterns uncovered from color images were matched with vein patterns from the rest of color images and with vein patterns from another one hundred fifty NIR images. The preliminary vein uncovering method according to various embodiments and vein patterns from the red channel were employed for comparison. For preliminary vein uncovering method, the same illuminant was used to uncover all the vein patterns. The red channel was included in the experiments because it was close to NIR channel. For preliminary vein uncovering method and the algorithm in accordance with various embodiments, vein patterns were extracted from the distribution maps of $d^{der}$.

Figure 38A:
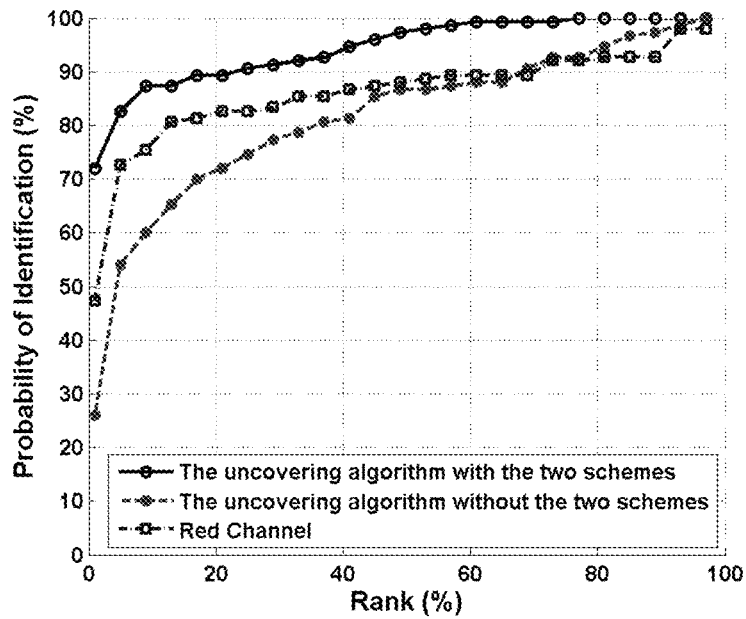
FIG. 38 shows a graph illustrating outputs of matching vein patterns for (a) colour image to colour image matching; and (b) colour image to NIR image matching, in accordance to various embodiments.

FIG. 38(a) shows the outputs of matching vein patterns from two sets of colour images. The rank-one identification accuracy of the algorithm according to various embodiments was about 72%, while those of the preliminary vein uncovering method and the red channel were only about 25% and about 47%, respectively. The rank-10% identification accuracy of the method according to various embodiments was about 87%, while those of the preliminary vein uncovering method and the red channel were about 60% and about 76%, respectively.

Figure 38B:
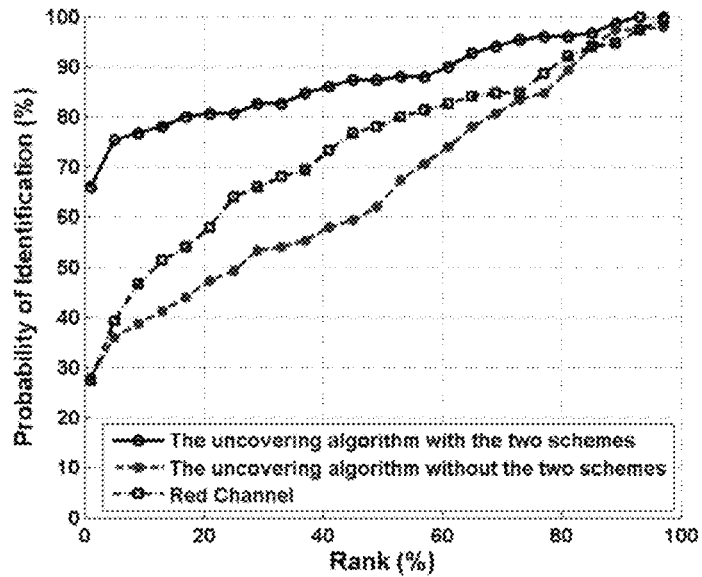

FIG. 38(b) shows the outputs of matching vein patterns from color images with those from NIR images. As with the results in FIG. 38(a), the algorithm in accordance with various embodiments appeared to still provide the best or most distinct vein uncovering. The rank-one identification accuracy of the algorithm in accordance with various embodiments was about 66% and the rank-10% identification accuracy was about 76.6%.

Comparing with the results in FIG. 38(a), the performances of red channel dropped significantly. The rank-one identification accuracy dropped to about 27%, which was even worse than the rank-one identification accuracy of about 28% from the preliminary vein uncovering method. However, the red channel still performed better in other regions or aspects. The rank-10% identification accuracy of the algorithm in accordance with various embodiments was about 76.6%, which was about 29.9% higher than that of the red channel and about 38% higher than that of preliminary vein uncovering method.

The outputs in FIGS. 38(a) and 38(b) demonstrated that (i) vein patterns may be uncovered from colour images for automatic criminal and victim identification; (ii) the two schemes according to various embodiments to address the preliminary algorithm were effective; (iii) red channel contained vein information; and (iv) matching vein patterns from the same images type (e.g. colour vs. colour) performed better than matching vein patterns from different types (e.g. colour vs. NIR). However, it was difficult to conclude that the preliminary method was not as good as the red channel, because it assumed that illuminant may be accurately estimated. Manually adjusting the illuminant for the preliminary method may be very time-consuming and impractical for large databases. Thus, the intensity adjustment scheme in accordance with various embodiments was vital in automatic criminal and victim identification based on veins.

Vein Uncovering Algorithm using IR Images and Colour Images

Figure 39:
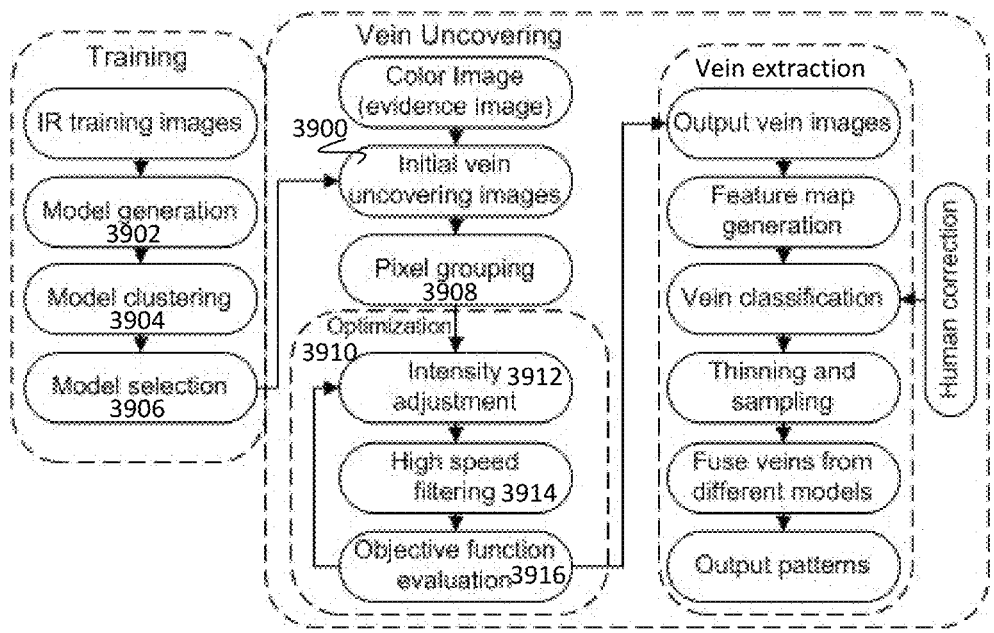
FIG. 39 shows a schematic block diagram of vein extraction for digital images, in accordance to various embodiments.

In one example, the vein uncovering algorithm 3900 may be applied to digital images as shown in FIG. 39 illustrating an overall schematic representation of various modules in accordance to various embodiments. For easy reference, the digital images in this example was referred to as colour images.

Model Generation 3902:

Let $I_{IR}$ be an IR image and $I_c$ be a colour image, capturing by a multi-spectral camera. The IR and colour images were captured simultaneously. Thus, a function $f$ with a set of control parameters (e.g. a neural network) may be trained to predicate the intensity of the IR image without image registration. Mathematically, $$\min_{v}\|I_{IR} - f(I_c, v)\|,$$

where v is a parametric vector, was performed. Given different image pairs ($I_{IRj}$ and $I_{cj}$), this minimization provided different parameter vectors $v_j$. Pixels with same colour may have different corresponding IR intensities. Using image pairs, $I_{IRj}$ and $I_{cj}$, where j=1 . . . n, a function pool containing $f(\bullet, v_1), \ldots, f(\bullet, v_n)$ may be established. Each $f(\bullet, v_j)$ may be a function for predicating IR images from colour images. Different functions were used to generate this pool to increase diversity.

Model clustering 3904 and Selection 3906:

Once the model pool was constructed, the nearly duplicated models may be removed. Let $\check{I}_{c1}, \ldots, \check{I}_{ck}$ be k different colour images and $R_j = [\hat{I}_{IR1j}^T, \ldots, \hat{I}_{IRkj}^T]^T$, where $\hat{I}_{IRij} = f(I_{c1}, v_j)$ and T represents transpose. $\hat{I}_{IRij}$ may be a column vector. If the models were nearly duplicated, the corresponding $R_j$ may be very similar. Thus, by clustering $R_j$, representative models may be identified.

Given a colour skin image $I_E$ from a crime scene, the representative models from training were firstly used to estimate the corresponding IR images, $\hat{I}_{IREj} = f(I_E, v_{rj})$, where $v_{rj}$ represents a parametric vector from a selected model.

In this example, before inputting $\hat{I}_{IREj}$ into the optimization loop, its pixels may be grouped 3908 to reduce the searching space. Pixels in $I_{IREj}$ from the pixels in $I_E$ with the same colour were assigned to the same group. Some groups with only several pixels may be merged according to colour distance.

The optimization loop 3910 has three components namely the intensity adjustment component 3912, the high speed filtering component 3914 and the objective evaluation component 3916 shown in FIG. 39. These components are described in further details in subsequent Example 3.

An exemplary preliminary optimization algorithm is as listed below:—

---

Compute the feature maps and $R_{s,\theta}$
Obtain a score $s_0$ from an objective function
Set $R_{s,\theta+} = R_{s,\theta-} = R_{s,\theta}$
For 1 to max number of iteration
  For group 1 to group N
    For each pixel in the group j //($x_0$, $y_0$) is the pixel position
      For all scale and orientation
        For (x, y) such that ($x_0$-x, $y_0$-y) in the support of $g_{s\theta}$
          $R_{s,\theta+}(x,y) = R_{s,\theta+}(x,y) + c \times g_{s\theta}(x_0-x, y_0-y)$
          $R_{s,\theta-}(x,y) = R_{s,\theta-}(x,y) - c \times g_{s\theta}(x_0-x, y_0-y)$
        End
      End
    End
    Compute the feature maps from $R_{s,\theta+}$ and $R_{s,\theta-}$
    Compute a score s+ from the objective function based on $R_{s,\theta+}$.
    Compute a score s− from the objective function based on $R_{s,\theta-}$.
    If ($s_+ > s_-$ and $s_+ > s_0$)
      Set $R_{s,\theta-} = R_{s,\theta+}$ and $R_{s,\theta} = R_{s,\theta+}$
    Else if ($s_- > s_+$ and $s_- > s_0$)
      Set $R_{s,\theta+} = R_{s,\theta-}$ and $R_{s,\theta} = R_{s,\theta-}$
    Else
      Set $R_{s,\theta+} = R_{s,\theta}$ and $R_{s,\theta-} = R_{s,\theta}$
    End
  End
End
Use the final $R_{s,\theta}$ to generate the feature maps.

---

The most time consuming components in the optimization loop 3910 may be the filtering 3914, because of the number of directional filters and the number of colour groups. One skin images may have more than one thousand colour groups. Although Fast Fourier Transform may be used to alleviate this problem, it may still not adequately resolve the problem. The exemplary preliminary algorithm uses an adaptive approach to address this problem.

EXAMPLE 3

Vein Extraction Algorithm

A vein extraction algorithm may be applied to both IR images and the distribution maps (or uncovered vein patterns) obtained from the vein uncovering algorithm in accordance with various embodiments of the invention and of Example 2.

Figure 40:
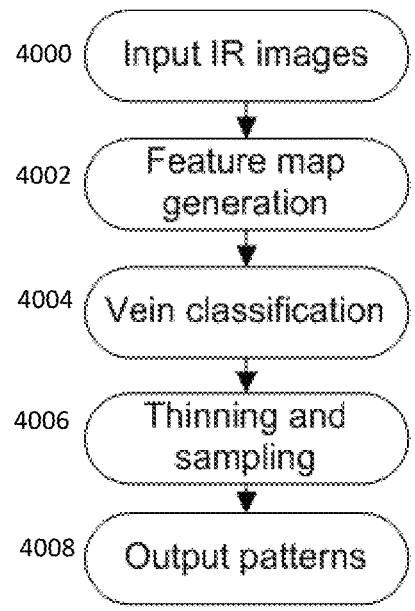
FIG. 40 shows a schematic block diagram of vein extract for IR images, in accordance to various embodiments.

Vein Extraction Algorithm Involving Response Map, Orientation Map, and Scale Map In an example, a schematic diagram of the vein extraction algorithm as shown in FIG. 40 was provided.

The vein extraction algorithm was applied to IR images 4000, which were captured in a controlled environment. IR has good penetration capability and users are able to cooperate with a full body scanner. The IR images showed relatively clear vein patterns. First, a set of multi-scale and directional filters was applied to the IR images. A zero-DC (direct current) Gabor filter made a good and suitable choice, because its feature extraction capability was demonstrated in many recognition systems, for example, in iris and palmprint identification systems and because its properties were well studied.

A 2D Gabor filter in spatial domain may generally be defined as:

$$g(x,y) = \exp\{-\pi[x'^2 a^2 + y'^2 b^2]\} \times \exp\{-2\pi i [u_0 x' + v_0 y']\}, \quad (40)$$

where $x' = (x - x_0)\cos\alpha + (y - y_0)\sin\alpha$ and $y' = (x - x_0)\sin\alpha + (y - y_0)\cos\alpha$.

Generally, there are seven degrees of freedom in 2D Gabor filters: ($x_0$, $y_0$) is the center of the filter in spatial domain, $\omega_0 = \sqrt{u_0^2 + v_0^2}$ is the spatial frequency, $\tan^{-1}(v_0/u_0)$ is the relative orientation between the complex wave and the Gaussian function, a and b control the shape of the Gaussian function and α is the orientation of the Gaussian function.

In this example, the real part of Gabor filter was enough for extracting vein patterns. Originally, this filter was not a zero DC filter. The DC component was to be removed. Let $g_{\Omega\theta}$ be a real part of a zero DC Gabor filter with orientation of θ and scale of Ω; I be an IR image and $R_{\Omega,\theta}(x, y) = I(x, y) * g_{\Omega\theta}(x, y)$, where * represents an operator of convolution. $g_{\Omega\theta}$ is normalized i.e., $\|g_{\Omega\theta}\| = 1$.

Using a Gabor filter bank with different scales and orientations, three feature maps namely orientation map, response map and scale map may be generated 4002. The response map may be defined as:

$$E(x, y) = \min_{\Omega, \theta} R_{\Omega, \theta}(x, y); \quad (41)$$

the orientation map may be defined as:

$$O(x, y) = \underset{\theta}{\operatorname{argmin}} R_{\Omega, \theta}(x, y) \quad (42)$$

and the scale map may be defined as:

$$S(x, y) = \underset{\Omega}{\arg\min} R_{\Omega,\theta}(x, y). \qquad (43)$$

Once three feature maps 4002 were generated. The orientation map and scale map were used to group the pixels. If connected pixels had the same scale and orientation, the connected pixels were put into the same group. Then, prior knowledge was employed to link different groups. For example, the prior knowledge may be as earlier described herein. If the spatial distance between two groups were less than a threshold and the orientation difference these between two groups may also be less than another threshold, these two groups may be linked.

Features (e.g. average E(x,y) in a group and group size) may be computed from the linked groups and input into a classifier 4004. The features obtained from manually labelled vein patterns and pure skin regions in the IR images may be used in training. For example, off-the-shelf classifiers may also be used to perform this classification task. In addition to classification 4004, the feature distributions of pure skin from different images and persons may be studied. Because the feature dimension may be low, it may be possible to model these distributions relatively accurately. If an accurate model may be derived, a Bayesian approach may be used to perform the classification. The study of these distributions may also be useful for classifying veins from colour images. Since the features may be extracted from a group, all pixels in same group may be assigned the same class label. This group-based approach may enhance the classification 4004 performance compared to pixel-based approaches as more information (e.g. veins having a larger group size), which may not be captured in pixel-based approaches, may be used. The classification output may form a black and white image. The white pixels represented veins and the black pixels represented pure skin. A thinning algorithm 4006 may be applied to this image and finally the skeleton of veins may be obtained. This skeleton may be the output patterns 4008. E(x,y) and skeleton 4008 formed may also be used in unified representation such as graphic representation.

Figure 41:
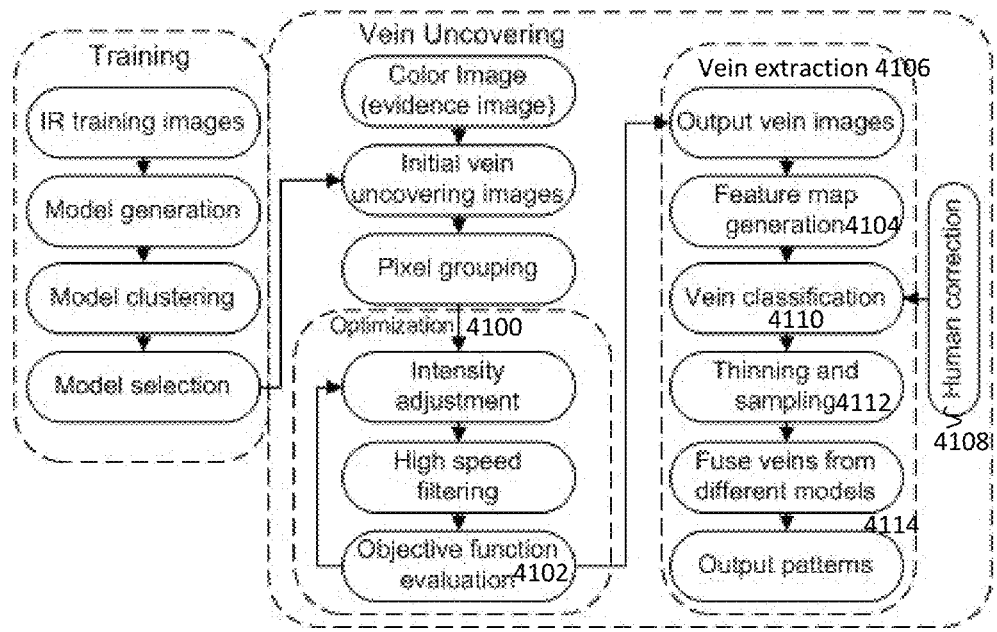
FIG. 41 shows a schematic block diagram of vein extraction for colour images, in accordance to various embodiments.

The study of these distributions may also be useful for classifying veins from digital images, for example, colour images. The vein extraction algorithm may be applied to digital images, for example, evidence images or colour images as illustrated in the schematic diagram of FIG. 41. In this example, the vein uncovering algorithm and the training of this algorithm involving model generation, model clustering and model selection may be as described in Example 2 with reference to FIG. 39. In FIG. 41, the optimization 4100 (similar to the optimization 3910 in FIG. 39) further comprised the use of the feature maps discussed above (in the case of vein pattern extracting applicable to IR images) to construct an objective function 4102 (similar to the objective function 3916 in FIG. 39). The contrast from E(x,y), complexity of the vein patterns and the group size may be taken into consideration to design the objective function 4102.

Before the first iteration, a Gabor filter bank may be applied to the input images. Let the filtered outputs be $R_{\Omega,\theta}(x, y) = I(x, y) * g_{\Omega\theta}(x, y)$. Then, the feature maps may be generated as the case for the vein extraction algorithm applied to IR images. Since Gabor filters were symmetric, convolution and spatial filtering was the same, i.e., $$R_{\Omega,\theta}(x,y) = \Sigma_p \Sigma_q I(x+p,y+q) \times g_{\Omega\theta}(x+p,y+q). \qquad (44)$$

Let $I_{new}(x_0,y_0) = I(x_0,y_0)+c$, $c \in R$ and $I_{new}(x, y) = I(x, y)$, $\forall(x, y) \neq (x_0, y_0)$. It may be shown that $R_{\Omega,\theta+}(x,y) = \Sigma_p \Sigma_q I_{new}(x+p, y+q) \times g_{\Omega\theta}(x+p, y+q)$ may be computed from $R_{\Omega,\theta}(x, y) = R_{\Omega,\theta}(x, y) + c(x+p, y+q) \times g_{\Omega\theta}(x_0-x, y_0-y)$. In the implementation, $g_{\Omega\theta}$ had a finite support. Thus, the summation was only performed over a finite region. Comparing with the direct approach, this adaptive approach provided extremely high speed filtering. Once the feature maps were obtained from the final $R_{\Omega,\theta}$ via the respective feature map generation 4104, 4002, the extraction of veins in color images 4106 and in IR images (as described with reference with FIG. 40) were nearly the same, except that manual or human correction 4108 may be allowed for digital images or colour images, for example when classifying the veins 4110. Along similar rationales, automatic fingerprint identification systems also provided a correction function as human experts are still regarded as being better than minutiae detection algorithms.

A thinning and sampling algorithm 4112 may be applied after vein classification 4110.

In the final stage, the vein patterns from different selected models obtained from IR images may be combined 4114. By doing so, the diversity of the models may be advantageously exploited and the drawbacks of the current existing model may be overcome.

An exemplary vein extraction scheme is provided to further illustrate and re-iterate the above example.

The vein extraction scheme may be divided into four parts: preprocessing, local information estimation, enhancement and representation. The aim of preprocessing is to alleviate problems from uneven illumination. To estimate the local directional information of veins, a Gabor filter bank was used to generate two information maps. Then, structural information of veins was captured from these information maps for vein pattern enhancement. Finally, the structural information of veins were represented by a set of points for matching.

Preprocessing and Local Information Estimation:

First, the contrasts of images were normalized by the contrast-limited adaptive histogram equalization (CLAHE) method (K. Zuiderveld, "Contrast Limited Adaptive Histograph Equalization", Graphic Gems IV, San Diego: Academic Press Professional, pp. 474-485, 1994). This method divided an image into small regions and stretches the histogram of each region into a desired distribution. In the algorithm in accordance to various embodiments of the invention, each image was divided into 8×8 blocks and uniform distribution was used as an objective histogram.

Figure 42A:
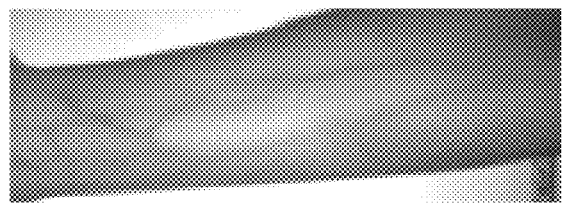
FIG. 42 shows preprocessing images of (a) an original NIR image; and (b) an output of CLAHE, in accordance to various embodiments.
Figure 42B:
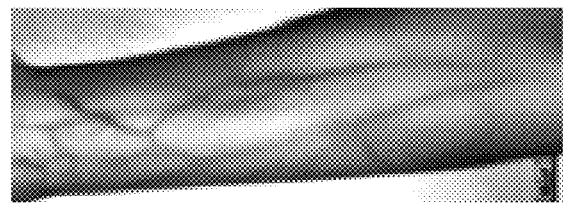

FIG. 42 shows preprocessing images of (a) an original NIR image; and (b) an output of CLAHE.

Gabor filters have been proved to be a powerful tool to capture local information. The algorithm in accordance with various embodiments applied a filter bank constituted by real parts of 16 Gabor filters with different scales and orientations to NIR images and distribution maps of $d^{der}$ to capture the respective local information.

Only the real parts of the Gabor filters were used because veins were dark ridges in NIR images and distribution maps. A real part of a Gabor filter in the spatial domain may be defined as $$G(x, y, \lambda_{mk}, \theta_k, \sigma_m, \gamma) = \frac{\gamma}{2\pi\sigma_m^2} \exp\left\{-\frac{x'^2 + \gamma^2 y'^2}{2\sigma_m^2}\right\} \cos\left(2\pi \frac{x'}{\lambda_{mk}}\right) \qquad (47)$$

where $x' = x \cos\theta_k + y \sin\theta_k$ and $y' = x \sin\theta_k + y \cos\theta_k$ are the rotated coordinates with orientation $$\theta_k = \frac{k\pi}{8};$$

$\lambda_{mk}$ represents the wavelength of the sinusoidal component; $\sigma_m$ is the standard deviation of the elliptical Gaussian window along x' direction; $\gamma$ is the spatial aspect ratio; $m \in \{1,2\}$ is the scale index and $k \in \{1, 2, \ldots, 8\}$ is the orientation index. The DC component in Eq. 47 was removed so that the filter may be robust against brightness variation and the power of the filer was normalized such that $\|G\|=1$.

Let img(x, y) denote a NIR image or a distribution map of $d^{der}$ and $F_{\lambda_{mk},\theta_k,\sigma_m,\gamma}(x, y)$ denote a filtered img(x, y), which may be obtained by $$F_{\lambda_{mk},\theta_k,\sigma_m,\gamma}(x,y) = -G(x,y,\lambda_{mk},\theta_k,\sigma_m,\gamma) * img(x,y) \quad (48)$$

where * represents an operation of a two-dimensional convolution.

Thus, for an input image, 16 filtered images were generated by the filter bank. Each filter was sensitive to veins with a particular direction, frequency and scale and therefore, the orientation and scale from the filter giving maximum response may be used to represent the orientation and scale of the vein, respectively. Although the DC of the filters was removed, filter response still depended on image contrast, which was highly influenced by poses and illumination conditions.

Thus $F_{\lambda_{mk},\theta_k,\sigma_m,\gamma}(x, y)/P_m(x, y)$, where $P_m$ is a local image power around the point (x, y), serves as the local information estimator. Note that $P_m$ depended on the size of the filters. The orientation of veins may be obtained from $$O(x, y) = \underset{\theta_k\ m,k}{\operatorname{argmax}} F_{\lambda_{mk},\theta_k,\sigma_m,\gamma}(x, y) / P_m(x, y) \quad (49)$$

which is called orientation map.

In addition, $$E(x, y) = \max_{m,k} F_{\lambda_{mk},\theta_k,\sigma_m,\gamma}(x, y) / P_m(x, y) \quad (50)$$

which is called energy map indicates the quality of local information.

FIG. 43 illustrates the Gabor filter outputs. Vein patterns from the energy and orientation maps may be observed.

Figure 43A:
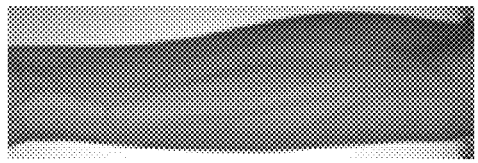
FIG. 43 shows (a) an original NIR image; (b) the distribution map of $d^{der}$ uncovered from the corresponding color image; (c) the energy map of (a); (e) the orientation map of (a); (d) the energy map of (b); and (f) the orientation map of (b), in accordance to various embodiments.
Figure 43B:
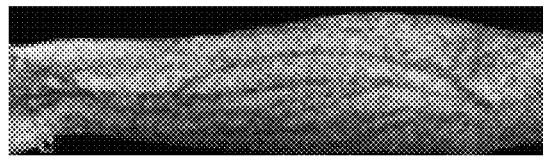
Figure 43C:
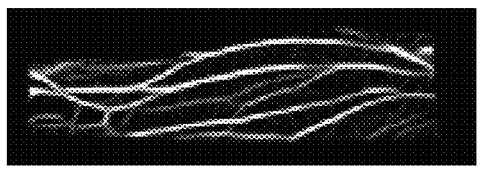
Figure 43D:
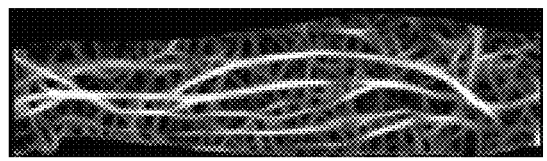
Figure 43E:
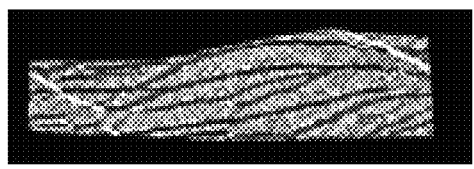
Figure 43F:
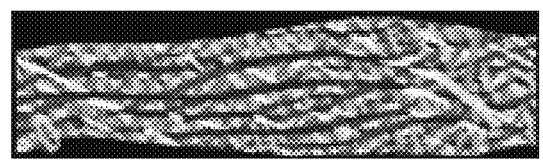

FIG. 43(a) shows an original NIR image and FIG. 43(b) shows the distribution map of $d^{der}$ uncovered from the corresponding color image. FIG. 43(c) and FIG. 43(e) show respectively the energy and orientation maps of FIG. 43(a). FIG. 43(d) and FIG. 43(f) show respectively the energy and orientation maps of FIG. 43(b).

Figure 44A:
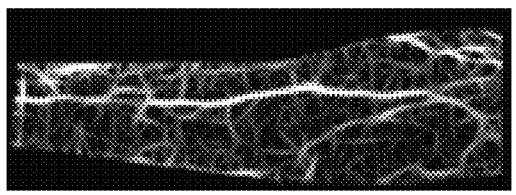
FIG. 44 shows images of vein enhancement of (a) an original energy map; (b) the potential vein components; (c) the map of grouped vein components (colour image); and (d) the enhanced energy map, in accordance to various embodiments.

Enhancement and Representation:

Energy maps, especially the ones generated from the distribution maps of $d^{der}$, were considerably noisy because of low image quality (e.g. FIG. 44(a)). Vein patterns in these energy maps should be enhanced and noise should be suppressed.

Structural information of veins in the orientation maps was used to enhance the energy maps. In orientation maps, short lines and small pixel groups were likely to be hairs or other noise, while long lines and large pixel groups provided more confidence of being veins. These characteristics were used to design our enhancement scheme.

Figure 44B:
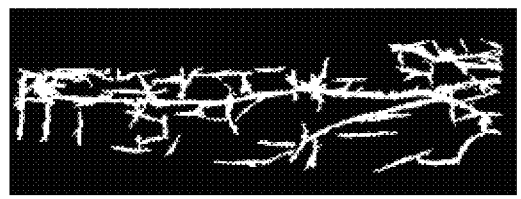

First the connected component labeling method (R. Haralick and L. Shapiro, "Computer and Robot Vision", Volume I, Addison-Wesley, pp. 28-48, 1992) was used to group pixels based on their orientations and generated a labeled map L(x, y)$\in\{1, \ldots, n\}$ with the same size as E(x, y). Pixels with the same label i (i=1, \ldots, n) were referred to as a component and denoted as c(i)=\{(x, y)|L(x, y)=i\}. All pixels in the same component c(i) were connected and had the same orientation O(i). If E(x, y) was higher than a threshold, this pixel was classified as a potential vein pixel and the corresponding component was then denoted as a potential vein component (see FIG. 44(b)). The potential vein components set V was defined as $$V = \{i | \exists (x,y) \in c(i), s.t.\ E(x,y) > \text{threshold}\}, \quad (51)$$

where the threshold is defined by the order statistics.

In the study, the 95 percentile was used. Potential vein components in V were further connected based on orientation difference and spatial distances between each pair of two groups. For every component pair in V, e.g. c(i) and c(j), where i, j$\in$V, if the respective angular distance was smaller than $\pi/8$ and the respective minimum distance, which may be defined as $$\Gamma(c(i), c(j)) = \min_{p,q}\left\{\sqrt{(x_{ip} - x_{jq})^2 + (y_{ip} - y_{jq})^2}\right\} \quad (52)$$

where $(x_{ip}, y_{ip}) \in c(i)$ and $(x_{jq}, y_{jq}) \in c(j)$, was smaller than a threshold $\zeta$, these were connected.

The set of connected components pairs are denoted as $$\Lambda = \left\{(i, j) \mid \forall\, i, j \in V,\ \Omega(O(i), O(j)) \leq \frac{\pi}{8},\ \Gamma(c(i), c(j)) < \zeta\right\} \quad (53)$$

where $\Omega$ represents angular distance.

The threshold was determined by trials. A large $\zeta$ linked more components together and performed better in restoring broken veins, while a small $\zeta$ linked fewer components and was more resistant to noise (e.g. hair). There was a trade-off in the setting of this threshold.

Figure 44C:

All the component pairs were iteratively searched through and the same labels were assigned to connected vein components in $\Lambda$ and a map of grouped labels $\Psi$ were generated (see FIG. 44(c)). g(i)=\{(x, y)|$\Psi$(x, y)=i\} represented pixels with the same label i (i=0, \ldots, m) and |g(i)| represented its size in term of number of pixels. The label zero was reserved for pixels that did not connect to any components in V. A weighting function W(x, y) based on the size of the groups may be defined as $$W(x,y) = \kappa \cdot [1 + \exp(-|g(i)|/\mu)]^{-1} \quad (54)$$

where (x, y)$\in$g(i).

The parameter $\mu$ controlled suppression and enhancement regions and the parameter $\kappa$ was a magnification factor. This weighting function was applied to E(x, y) point-wisely, i.e., W(x, y)×E(x, y).

Figure 44D:
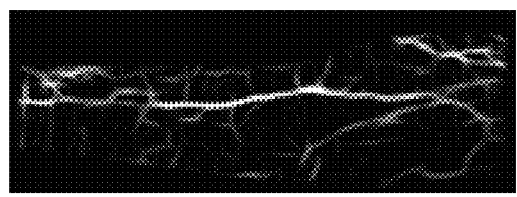
Figure 45A:
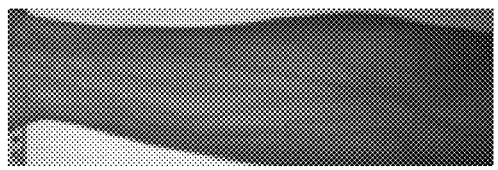
FIG. 45 shows (a) an original NIR image; (b) the enhanced energy map of (a); (c) the sampled points from the boundary.
Figure 45B:
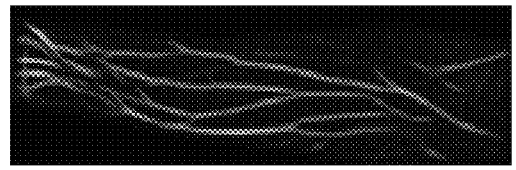
Figure 45C:
Figure 45D:
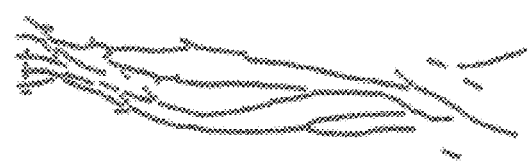

FIG. 44(d) shows the enhanced vein patterns. The enhanced vein patterns were binarized using Otsu's method and then skeletonized. Finally, the vein patterns were uniformly sampled and represented by a set of points. The boundaries of body parts were also sampled and represented in the same way. An example of sampled vein patterns and boundaries is shown in FIG. 45. FIG. 45(a) shows an original NIR image, FIG. 45(b) shows the enhanced energy map of FIG. 45(a), FIG. 45(c) shows the sampled points from the boundary and FIG. 45(d) shows the sampled points from the vein patterns.

Figure 47A:
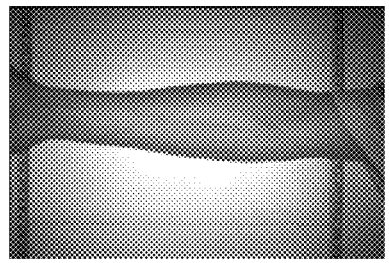
Figure 47B:
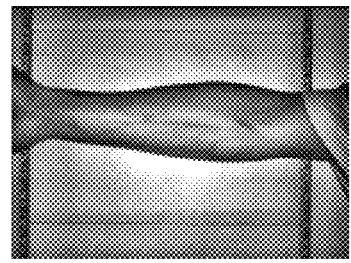

In yet another example, a schematic diagram of the vein extraction algorithm as shown in FIG. 46 was provided. The algorithm 4600 contained seven main computational components. First of all, an adaptive histogram equalization 4602 was applied to increase image contrast of IR images or distribution maps obtained from any vein uncovering algorithm 4604, for example, the vein uncovering algorithm in accordance to various embodiments of the invention (reference also to Example 2). FIG. 47(a) shows the image contrast of an example of an original image captured by an IR camera and FIG. 47(b) shows the image contrast of an example of an output from adaptive histogram equalization 4602.

Figure 48A:
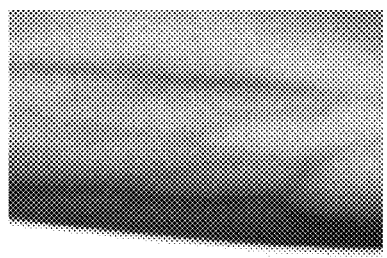
Figure 48B:
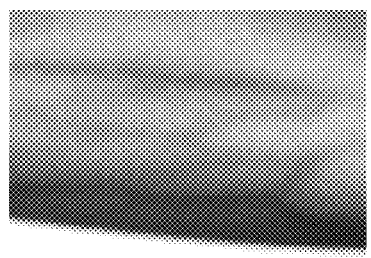
Figure 49A:
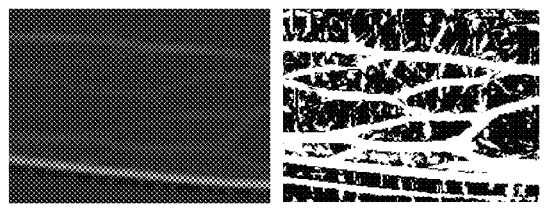
Figure 49B:
Figure 49C:
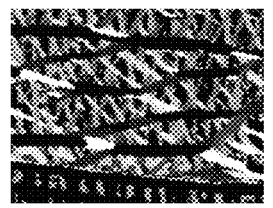
Figure 49D:
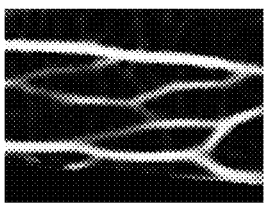

Then, a Gaussian filter 4606 was used to remove the high frequency noise. FIG. 48(a) shows an output from the adaptive histogram equalization 4602 and FIG. 48(b) shows the low-pass output after going through the Gaussian filter 4606.

A multiscale Gabor filter bank 4608 was employed to compute scale, magnitude and orientation maps of vein patterns. An example of the Gabor filter bank 4608 may be comprised in the feature map generation 4104 of the vein extraction 4106 of FIG. 41.

Let $G_{\Omega\theta}$ a be a Gabor filter with a scale $\Omega$ and a direction (or orientation) $\theta$, where $0 \leq \Omega \leq S$ and $0 \leq \theta \leq D$ where S and D were the maximum scale and the maximum orientation D. Mathematically, the scale map $\Omega$ and the orientation map $\theta$ may be obtained by:

$$[\Omega(x, y), \theta(x, y)] = \underset{\Omega,\theta}{\mathrm{argmax}}(Mag(G_{\Omega\theta}(x, y) * I)), \quad (55)$$

where * represents a convolution operator, and the magnitude map $\Pi$ may be defined as:

$$\left[\prod(x, y), \theta(x, y)\right] = \underset{\Omega,\theta}{\max}(Mag(G_{\Omega\theta}(x, y) * I)), \quad (56)$$

FIG. 49 shows output examples from the Gabor filter 4608 wherein (a) being a magnitude map, (b) being a scale map, and (c) being an orientation map. To estimate the likelihood of a pixel belonging to a vein or not, the magnitude of the pixel and the magnitudes of its neighborhood were formed as a feature vector and were inputted into a neural network classifier 4610. FIG. 49(d) shows an output example of the neural network classifier 4610. An example of the neural network classifier 4610 may be the vein classification 4110 of the vein extraction 4106 of FIG. 41.

A multi-stage thresholding scheme 4612 may be used to determine the vein pattern from the output of the neural network classifier 4610. Firstly, a global threshold g where g is obtained from the Otsu's method (Nobuyuki Otsu (1979), "A threshold selection method from gray-level histograms", *IEEE Trans. Sys., Man., Cyber,* 9 (1): 62-66, doi:10.1109/TSMC.1979.4310076, and M. Sezgin and B. Sankur (2003), "Survey over image thresholding techniques and quantitative performance evaluation", *Journal of Electronic Imaging* 13 (1): 146-165, doi:10.1117/1.1631315) was used to binarize the neural network output as shown in FIG. 50(a). This threshold was computed from the skin area only, which was to say that the background of the image did not affect the threshold. Then, a lower threshold g/2.5 was then applied to the regions around the vein pattern detected by the first threshold as shown in FIG. 50(b). The detected veins were elongated based on the information from the scale and orientation maps. FIG. 51 shows a schematic diagram of an elongation process. For every pixel in the neural network output, its orientation and scale were obtained and the pixels in a rectangular box, for example, rectangular box 5100 in FIG. 51 were analyzed. The size and orientation of the rectangular box 5100 having the pixel 5102 at its center were controlled by the scale and orientation of the pixel, respectively. If there exist detected vein pixels 5104 having the same orientation as the testing pixel 5102 and the response of the testing pixel 5102 in the neural network output was greater than g/2.5, it may be considered as a vein pixel 5106. If there was no vein pixel in the rectangular box, the testing pixel 5102 may not be considered as a vein pixel 5108.

To further elongate the veins, this elongation process was applied again with the threshold g/2.5 replaced by a local threshold h/2, where h is an Otsu's threshold computed from a local region as illustrated by the threshold scheme of FIG. 50(c). Finally, morphologic operators were applied to refine the vein pattern as seen in FIG. 50(d).

Figure 52A:
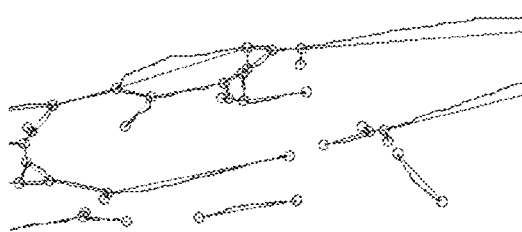
Figure 52B:
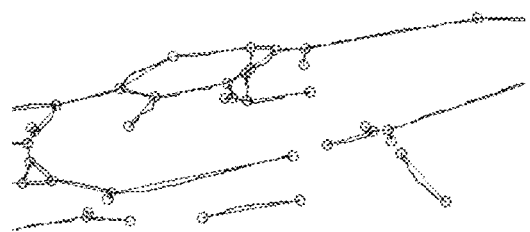
Figure 52C:
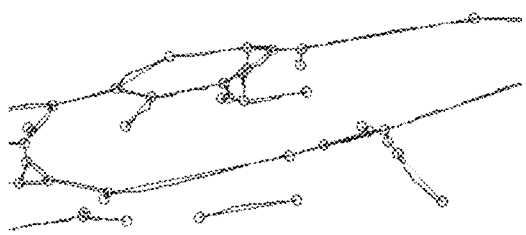
Figure 52D:
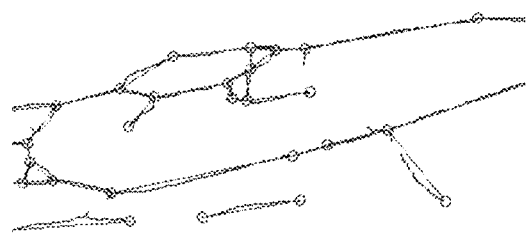

A thinning algorithm 4614 to the binary outputs from the multi-stage thresholding scheme 4612 to obtain the structure of the vein pattern. An example of the thinning algorithm 4614 may be the thinning and sampling 4112 of the vein extraction 4106 of FIG. 41. The final stage of vein extraction was to represent the vein pattern as a graph 4616. Then, intersection and end points were detected and regarded as nodes of the graph. Straight lines were used to link the nodes that were directly connected by veins as shown in FIG. 52(a). An additional node may be inserted if the curvature of a vein segment was larger than a threshold as shown in FIG. 52(b). Then, broken veins were connected as illustrated in FIG. 52(c) and finally, short veins were removed as shown in FIG. 52(d). This final graph may be used for vein matching.

In the context of various embodiments, the term "about" or "approximately" as applied to a numeric value encompasses the exact value and a variance of +/−5% of the value.

The phrase "at least substantially" may include "exactly" and a variance of +/−5% thereof. As an example and not limitation, the phrase "A is at least substantially the same as B" may encompass embodiments where A is exactly the same as B, or where A may be within a variance of +/−5%, for example of a value, of B, or vice versa.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A method of determining vein patterns from a colour image for personal identification, the method comprising:
    forming a counterpart of the colour image by applying a functional relationship obtained from optimization on the colour image, wherein the counterpart of the colour image comprises the vein patterns,
    wherein the functional relationship is formulated using a model modelling colour image and a counterpart of the modelling colour image, wherein the counterpart of the modelling colour image comprises modelling vein patterns.

2. The method as claimed in claim 1, wherein in forming the counterpart of the colour image, applying the functional relationship on the colour image is applying a neural network on the colour image.

3. The method as claimed in claim 2, wherein forming the counterpart of the colour image further comprises training the neural network by back-propagation.

4. The method as claimed in claim 1, wherein forming the counterpart of the colour image further comprises selecting the functional relationship from a plurality of functional relationships between modelling colour images and counterparts of the modelling colour images.

5. The method as claimed in claim 4, further comprising grouping parts of the counterpart of the colour image.

6. The method as claimed in claim 5, wherein grouping parts of the counterpart of the colour image comprises assigning pixels in the IR image having substantially the same colour to a same group.

7. The method as claimed in claim 1, wherein the counterpart of the modelling colour image comprises an infrared (IR) image or a near-infrared (NIR) image.

8. The method as claimed in claim 7, wherein the functional relationship comprises a plurality of functional relationships between colour images and IR images wherein each colour image and the respective IR image thereof forms an image pair; and wherein for at least one of the image pairs, the colour image and the respective IR image are captured simultaneously.

9. The method as claimed in claim 8, wherein forming the counterpart of the colour image further comprises training with a set of image pairs formed by the modelling colour images and the IR images thereof.

10. The method as claimed in claim 7, wherein the functional relationship comprises a parametric vector for predicating the IR image from the colour image.

11. The method as claimed in claim 1, further comprising removing blocking artifacts in the colour image, wherein the colour image is a compressed colour image.

12. The method as claimed in claim 11, wherein removing blocking artifacts comprises using a knowledge-based approach or a one-pass algorithm.

13. The method as claimed in claim 1, further comprising extracting vein patterns from an image, wherein the image comprises a plurality of pixels.

14. The method as claimed in claim 1, wherein the colour image is a true colour image.

15. A method of determining vein patterns from a colour image for personal identification, the method comprising:
   forming a counterpart of the colour image by applying a functional relationship obtained from optimization on the colour image, wherein the counterpart of the colour image comprises the vein patterns,
   wherein the functional relationship obtained from optimization is formulated using an approximate regression comprising a least-squares-error energy function with an optimal weight.

16. A method of determining vein patterns from a colour image for personal identification, the method comprising:
   forming a counterpart of the colour image by applying a functional relationship obtained from optimization on the colour image, wherein the counterpart of the colour image comprises the vein patterns,
   wherein the colour image comprises colour components;
   wherein the counterpart of the colour image comprises skin-characterizing variables; and
   wherein forming a counterpart of the colour image comprises determining distributions of the skin-characterizing variables to form the vein patterns.

17. The method as claimed in claim 16, wherein determining distributions of the skin-characterizing variables comprises applying an inverse of the functional relationship on the colour components obtained from the colour image.

18. The method as claimed in claim 17, wherein the colour components comprise a red (R) component, a green (G) component, and a blue (B) component.

19. An apparatus for determining vein patterns from a colour image for personal identification, the apparatus comprising:
   a determining unit configured to form a counterpart of the colour image by applying a functional relationship obtained from optimization on the colour image, wherein the counterpart of the colour image comprises the vein patterns,
   wherein the functional relationship is formulated using a modelling colour image and a counterpart of the modelling colour image, wherein the counterpart of the modelling colour image comprises modelling vein patterns.

20. The apparatus as claimed in claim 19, wherein the colour image is a true colour image.

* * * * *